United States Patent
Alig et al.

(10) Patent No.: US 9,936,700 B2
(45) Date of Patent: Apr. 10, 2018

(54) SUBSTITUTED QUINOXALINE DERIVATIVES AS PEST CONTROL AGENT

(71) Applicant: BAYER CROPSCIENCE AKTIENGESELLSCHAFT, Monheim am Rhein (DE)

(72) Inventors: Bernd Alig, Koenigswinter (DE); Joerg Greul, Leverkusen (DE); Ruediger Fischer, Pulheim (DE); Hans-Georg Schwarz, Dorsten (DE); Niklas Tim Bretschneider, Lohmar (DE); Uta Bretschneider, Lohmar (DE); Reiner Fischer, Monheim (DE); Daniela Portz, Vettweiss (DE); Olga Malsam, Roesrath (DE); Peter Loesel, Leverkusen (DE); Kerstin Ilg, Cologne (DE); Angela Becker, Duesseldorf (DE); Ulrich Goergens, Ratingen (DE); Stefan Herrmann, Langenfeld (DE); Claudia Welz, Duesseldorf (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/029,533

(22) PCT Filed: Oct. 20, 2014

(86) PCT No.: PCT/EP2014/072432
§ 371 (c)(1),
(2) Date: Apr. 14, 2016

(87) PCT Pub. No.: WO2015/059088
PCT Pub. Date: Apr. 30, 2015

(65) Prior Publication Data
US 2016/0227779 A1    Aug. 11, 2016

(30) Foreign Application Priority Data
Oct. 23, 2013    (EP) .................... 13189894

(51) Int. Cl.
| | |
|---|---|
| *A01N 43/60* | (2006.01) |
| *C07D 401/04* | (2006.01) |
| *C07D 403/04* | (2006.01) |
| *C07D 409/04* | (2006.01) |
| *C07D 241/40* | (2006.01) |
| *C07D 491/04* | (2006.01) |
| *A01N 43/90* | (2006.01) |
| *C07D 213/50* | (2006.01) |
| *C07D 491/056* | (2006.01) |

(52) U.S. Cl.
CPC .............. *A01N 43/60* (2013.01); *A01N 43/90* (2013.01); *C07D 213/50* (2013.01); *C07D 241/40* (2013.01); *C07D 401/04* (2013.01); *C07D 403/04* (2013.01); *C07D 409/04* (2013.01); *C07D 491/04* (2013.01); *C07D 491/056* (2013.01)

(58) Field of Classification Search
None
See application file for complete search history.

(56) References Cited

U.S. PATENT DOCUMENTS

| | | | |
|---|---|---|---|
| 5,480,883 A | 1/1996 | Spada et al. | |
| 5,527,911 A | 6/1996 | Guglielmetti et al. | |
| 6,541,633 B1 | 4/2003 | Tan et al. | |

(Continued)

FOREIGN PATENT DOCUMENTS

| | | |
|---|---|---|
| DE | 258 165 A1 | 7/1988 |
| DE | 262 790 A1 | 12/1988 |
| JP | 2013 246249 A | 12/2013 |

(Continued)

OTHER PUBLICATIONS

Tsubata et al., Journal of Organic Chemistry (1992), 57(25), 6749-55.*
Shilu Fan et al. "PD-Catalyzed Direct Cross-Coupling of Electron-Deficient Polyfluoroarenes With Heteroaromatic Tosylates", Organic Letters, vol. 13, No. 16, (2011) XP055153413.
Pierre Koch et al. "Pyridinylquionoxalines and Pyridinylpyridopyrazines as Lead Compounds for Novel p38[alpha]Mitogen-Activated Protein Kinase Inhibitors", Journal of Medicinal Chemistry, vol. 53, No. 3. (2010) XP055153418.

(Continued)

*Primary Examiner* — Karl J Puttlitz
(74) *Attorney, Agent, or Firm* — McBee Moore Woodward & Vanik IP, LLC

(57) ABSTRACT

The invention relates to novel compounds of the formula (I)

(I)

in which $R^1$, $R^2$, $R^3$, $R^4$, $R^5$, $R^6$, $Y^1$ and $Y^2$ have the meanings given above,
to a plurality of processes and intermediates for their preparation and to their use as acaricides and/or insecticides for controlling animal pests. The compounds of the formula (I) are also suitable as nematicides for plant-damaging pests and/or anthelminthics for endoparasites in humans and animals.

11 Claims, No Drawings

(56) References Cited

U.S. PATENT DOCUMENTS

| | | | |
|---|---|---|---|
| 6,548,499 B1 * | 4/2003 | Carson | C07D 231/12 514/249 |
| 9,260,436 B2 | 2/2016 | Takahashi et al. | |

FOREIGN PATENT DOCUMENTS

| | | |
|---|---|---|
| WO | 99/42463 A1 | 8/1999 |
| WO | 2008/148867 A2 | 12/2008 |
| WO | 2009/021083 A1 | 2/2009 |
| WO | 2012/045196 A1 | 4/2012 |
| WO | 2013/191112 A1 | 12/2013 |

OTHER PUBLICATIONS

Iftikhar Ali "Regioselecive Suzuki-Miyaura Cross-Coupling Reactions of 2,6-Dichloroquinoxaline", Synthesis (2012) vol. 44 pp. 1637-1646, XP055092174.

Laetitia J. Martin et al. "Safe and Reliable Synthesis of Diazokethones and Quinoxalines in a Continous Flow Reactor", Organic Letters (2011) vol. 13, No. 2, 320-323. XP055092180.

M. Loriga "2-Phenyl-6(7)-R-Substituted Quinoxalines N-Oxides. Synthesis, Structure Elucidation and Antimicrobial Activity", Eur J. Med. Chem (1990) vol. 25 pp. 527-532, XP055092183.

F.B Mallory et al. "Furazan Oxides. IV. Extensions of the Scope of the Haloalkoxy Substitute Reaction", J. Org. Chem, vol. 25 (1964) pp. 2605-2609, XP055092208.

* cited by examiner

SUBSTITUTED QUINOXALINE DERIVATIVES AS PEST CONTROL AGENT

CROSS REFERENCE TO RELATED APPLICATIONS

This application is a § 371 National Stage Application of PCT/EP2014/072432, filed Oct. 20, 2014, which claims priority to European 13189894.2 filed Oct. 23, 2013.

BACKGROUND

Field of the Invention

The present invention relates to novel substituted 2-(het)arylquinoxaline derivatives of the formula (I), to their use as acaricides and/or insecticides for controlling animal pests and to processes and intermediates for their preparation. The compounds of the formula (I) are also suitable as nematicides for plant-damaging pests and/or anthelminthics for endoparasites in humans and animals.

Description of Related Art

DD 262790 discloses the use of 2-aryl- and 2-hetarylquinoxalines as acaricides. The Japanese patent application JP 2004346016 discloses trifluoromethyl-substituted quinoxalines as pesticides.

DD 258165 discloses the use of 2-hetarylquinoxalines as algicides and herbicides.

WO 2013/19112 discloses heterocyclic compounds and their insecticidal action.

The active compounds already known from the publications mentioned above have, on application, only insufficient acaricidal activity against animal pests, in particular at relatively low application rates.

SUMMARY

Accordingly, it is an object of the present invention to provide corresponding substituted 2-(het)arylquinoxaline derivatives which can be employed as insecticides and/or acaricides with satisfactory insecticidal and/or acaricidal activity against animal pests, in particular at relatively low application rates, with high selectivity and improved compatibility in crops of useful plants. It is another object of the present invention to provide appropriate substituted 2-(het) arylquinoxaline derivatives which can be used as nematicides and/or anthelminthics.

Surprisingly, we have now found novel compounds of the formula (I)

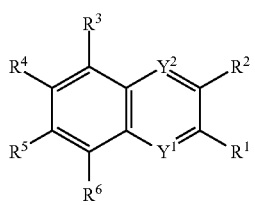

(I)

in which
$Y^1$ and $Y^2$ independently of one another represent N or $N^+\!\!-\!\!O^-$,
$R^1$ represents aryl or hetaryl, each of which is optionally mono- or polysubstituted by identical or different substituents, where (in the case of hetaryl) at least one carbonyl group may optionally be present and/or where possible substituents in each case are as follows: cyano, carboxyl, halogen, nitro, acetyl, hydroxyl, amino, SCN, $SF_5$, tri-$(C_1\text{-}C_6)$-alkylsilyl, $(C_1\text{-}C_6)$-alkyl, $(C_1\text{-}C_6)$-haloalkyl, $(C_1\text{-}C_6)$-cyanoalkyl, $(C_1\text{-}C_6)$-hydroxyalkyl, hydroxycarbonyl-$(C_1\text{-}C_4)$-alkoxy, $(C_1\text{-}C_6)$-alkoxycarbonyl-$(C_1\text{-}C_4)$-alkyl, $(C_1\text{-}C_6)$-alkoxy-$(C_1\text{-}C_6)$-alkyl, $(C_2\text{-}C_6)$-alkenyl, $(C_2\text{-}C_6)$-haloalkenyl, $(C_2\text{-}C_6)$-cyanoalkenyl, $(C_2\text{-}C_6)$-alkynyl, $(C_2\text{-}C_6)$-haloalkynyl, $(C_2\text{-}C_6)$-cyanoalkynyl, $(C_1\text{-}C_6)$-alkoxy, $(C_1\text{-}C_6)$-haloalkoxy, $(C_1\text{-}C_6)$-cyanoalkoxy, $(C_1\text{-}C_7)$-alkoxycarbonyl-$(C_1\text{-}C_6)$-alkoxy, $(C_1\text{-}C_6)$-alkoxy-$(C_1\text{-}C_6)$-alkoxy, $(C_1\text{-}C_7)$-alkylhydroxyimino, $(C_1\text{-}C_7)$-alkoxyimino, $(C_1\text{-}C_6)$-alkyl-$(C_1\text{-}C_7)$-alkoxyimino, $(C_1\text{-}C_6)$-haloalkyl-$(C_1\text{-}C_7)$-alkoxyimino, $(C_1\text{-}C_6)$-alkylthio, $(C_1\text{-}C_6)$-haloalkylthio, $(C_1\text{-}C_6)$-alkoxy-$(C_1\text{-}C_6)$-alkylthio, $(C_1\text{-}C_6)$-alkylthio-$(C_1\text{-}C_6)$-alkyl, $(C_1\text{-}C_6)$-alkylsulfinyl, $(C_1\text{-}C_6)$-haloalkylsulfinyl, $(C_1\text{-}C_6)$-alkoxy-$(C_1\text{-}C_6)$-alkylsulfinyl, $(C_1\text{-}C_6)$-alkylsulfinyl-$(C_1\text{-}C_6)$-alkyl, $(C_1\text{-}C_6)$-alkylsulfonyl, $(C_1\text{-}C_6)$-haloalkylsulfonyl, $(C_1\text{-}C_6)$-alkoxy-$(C_1\text{-}C_6)$-alkylsulfonyl, $(C_1\text{-}C_6)$-alkylsulfonyl-$(C_1\text{-}C_6)$-alkyl, $(C_1\text{-}C_6)$-alkylsulfonyloxy, $(C_1\text{-}C_7)$-alkylcarbonyl, $(C_1\text{-}C_7)$-haloalkylcarbonyl, $(C_1\text{-}C_7)$-alkylcarbonyloxy, $(C_1\text{-}C_7)$-alkoxycarbonyl, $(C_1\text{-}C_7)$-haloalkoxycarbonyl, aminocarbonyl, $(C_1\text{-}C_7)$-alkylaminocarbonyl, di-$(C_1\text{-}C_7)$-alkylaminocarbonyl, $(C_2\text{-}C_7)$-alkenylaminocarbonyl, di-$(C_2\text{-}C_7)$-alkenylaminocarbonyl, $(C_3\text{-}C_8)$-cycloalkylaminocarbonyl, $(C_1\text{-}C_6)$-alkylsulfonylamino, $(C_1\text{-}C_6)$-alkylamino, aminosulfonyl, $(C_1\text{-}C_6)$-alkylaminosulfonyl, di-$(C_1\text{-}C_6)$-alkylaminosulfonyl, $(C_1\text{-}C_6)$-alkylsulfoximino, aminothiocarbonyl, $(C_1\text{-}C_6)$-alkylaminothiocarbonyl, di-$(C_1\text{-}C_6)$-alkylaminothiocarbonyl, $(C_3\text{-}C_8)$-cycloalkylamino, $(C_1\text{-}C_6)$-alkylsulfonylamino, represents phenyl, pyridyl or phenoxy, each of which is optionally substituted by halogen, $(C_1\text{-}C_6)$-alkyl, $(C_1\text{-}C_6)$-haloalkyl, $(C_1\text{-}C_6)$-alkylthio, $(C_1\text{-}C_6)$-alkoxy or $(C_1\text{-}C_6)$-haloalkoxy, $R^2$ represents hydrogen, cyano, halogen, nitro, acetyl, hydroxy, amino, SCN, tri-$(C_1\text{-}C_6)$-alkylsilyl, cyclo-$(C_3\text{-}C_8)$-alkyl, $(C_1\text{-}C_6)$-alkyl, $(C_1\text{-}C_6)$-haloalkyl, $(C_1\text{-}C_6)$-cyanoalkyl, $(C_1\text{-}C_6)$-hydroxyalkyl, hydroxycarbonyl-$(C_1\text{-}C_4)$-alkoxy, $(C_1\text{-}C_6)$-alkoxycarbonyl-$(C_1\text{-}C_4)$-alkyl, $(C_1\text{-}C_6)$-alkoxy-$(C_1\text{-}C_6)$-alkyl, $(C_2\text{-}C_6)$-alkenyl, $(C_2\text{-}C_6)$-haloalkenyl, $(C_2\text{-}C_6)$-cyanoalkenyl, $(C_2\text{-}C_6)$-alkynyl, $(C_2\text{-}C_6)$-haloalkynyl, $(C_2\text{-}C_6)$-cyanoalkynyl, $(C_1\text{-}C_6)$-alkoxy, $(C_1\text{-}C_6)$-haloalkoxy, $(C_1\text{-}C_6)$-cyanoalkoxy, $(C_1\text{-}C_7)$-alkoxycarbonyl-$(C_1\text{-}C_6)$-alkoxy, $(C_1\text{-}C_6)$-alkoxy-$(C_1\text{-}C_6)$-alkoxy, $(C_1\text{-}C_7)$-alkylhydroxyimino, $(C_1\text{-}C_7)$-alkoxyimino, $(C_1\text{-}C_6)$-alkyl-$(C_1\text{-}C_7)$-alkoxyimino, $(C_1\text{-}C_6)$-haloalkyl-$(C_1\text{-}C_7)$-alkoxyimino, $(C_1\text{-}C_6)$-alkylthio, $(C_1\text{-}C_6)$-haloalkylthio, $(C_1\text{-}C_6)$-alkoxy-$(C_1\text{-}C_6)$-alkylthio, $(C_1\text{-}C_6)$-alkylthio-$(C_1\text{-}C_6)$-alkyl, $(C_1\text{-}C_6)$-alkylsulfinyl, $(C_1\text{-}C_6)$-haloalkylsulfinyl, $(C_1\text{-}C_6)$-alkoxy-$(C_1\text{-}C_6)$-alkylsulfinyl, $(C_1\text{-}C_6)$-alkylsulfinyl-$(C_1\text{-}C_6)$-alkyl, $(C_1\text{-}C_6)$-alkylsulfonyl, $(C_1\text{-}C_6)$-haloalkylsulfonyl, $(C_1\text{-}C_6)$-alkoxy-$(C_1\text{-}C_6)$-alkylsulfonyl, $(C_1\text{-}C_6)$-alkylsulfonyl-$(C_1\text{-}C_6)$-alkyl, $(C_1\text{-}C_6)$-alkylsulfonyloxy, $(C_1\text{-}C_7)$-alkylcarbonyl, $(C_1\text{-}C_7)$-haloalkylcarbonyl, $(C_1\text{-}C_7)$-alkylcarbonyloxy, $(C_1\text{-}C_7)$-alkoxycarbonyl, $(C_1\text{-}C_7)$-haloalkoxycarbonyl, aminocarbonyl, $(C_1\text{-}C_7)$-alkylaminocarbonyl, di-$(C_1\text{-}C_7)$-alkyl-aminocarbonyl, $(C_2\text{-}C_7)$-alkenylaminocarbonyl, di-$(C_2\text{-}C_7)$-alkenylaminocarbonyl, $(C_3\text{-}C_8)$-cycloalkylaminocarbonyl, $(C_1\text{-}C_6)$-alkylsulfonylamino, $(C_1\text{-}C_6)$-alkylamino, aminosulfonyl, $(C_1\text{-}C_6)$-alkylaminosulfonyl, di-$(C_1\text{-}C_6)$-alkylaminosulfonyl, $(C_1\text{-}C_6)$-alkylsulfoximino, aminothiocarbonyl, $(C_1\text{-}C_6)$-alkylaminothiocarbonyl, di-$(C_1\text{-}C_6)$-alkylaminothiocarbonyl, $(C_3\text{-}C_8)$-cycloalkylamino, $(C_1\text{-}C_6)$-alkylsulfonylamino, represents aryl or hetaryl, each of which is optionally mono- or polysubstituted by identical or different substituents, where (in the case of hetaryl) at least one carbonyl group may optionally be present and/or where possible substituents are in each case as follows: cyano, carboxyl, halogen, nitro, acetyl, hydroxyl, amino, SCN, tri-($C_1$-$C_6$)-alkylsilyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_4$)-alkoxy, ($C_1$-$C_6$)-alkoxycarbonyl-($C_1$-$C_4$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_7$)-alkoxycarbonyl-($C_1$-$C_6$)-alkoxy, ($C_1$-$C_6$)-alkoxy-($C_1$-$C_6$)-alkoxy, ($C_1$-$C_7$)-alkylhydroxyimino, ($C_1$-$C_7$)-alkoxyimino, ($C_1$-$C_6$)-alkyl-($C_1$-$C_7$)-alkoxyimino, ($C_1$-$C_6$)-haloalkyl-($C_1$-$C_7$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_7$)-alkylcarbonyl, ($C_1$-$C_7$)-haloalkylcarbonyl, ($C_1$-$C_7$)-alkylcarbonyloxy, ($C_1$-$C_7$)-alkoxycarbonyl, ($C_1$-$C_7$)-haloalkoxycarbonyl, aminocarbonyl, ($C_1$-$C_7$)-alkylaminocarbonyl, di-($C_1$-$C_7$)-alkylaminocarbonyl, ($C_2$-$C_7$)-alkenylaminocarbonyl, di-($C_2$-$C_7$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylsulfonylamino, represents phenyl, pyridyl or phenoxy, each of which is optionally substituted by halogen, ($C_1$-$C_6$)-alkyl, ($C_1$-$C_6$)-haloalkyl, ($C_1$-$C_6$)-alkylthio, ($C_1$-$C_6$)-alkoxy or ($C_1$-$C_6$)-haloalkoxy, where the attachment of $R^1$ to the quinoxaline derivative can only be via a carbon atom, $R^3$, $R^4$, $R^5$ and $R^6$ independently of one another represent hydrogen, cyano, carboxy, halogen, nitro, acetyl, hydroxy, amino, SCN, tri-($C_1$-$C_6$)-alkylsilyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_4$)-alkoxy, ($C_1$-$C_6$)-alkoxycarbonyl-($C_1$-$C_4$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_7$)-alkoxycarbonyl-($C_1$-$C_6$)-alkoxy, ($C_1$-$C_6$)-alkoxy-($C_1$-$C_6$)-alkoxy, ($C_1$-$C_7$)-alkylhydroxyimino, ($C_1$-$C_7$)-alkoxyimino, ($C_1$-$C_6$)-alkyl-($C_1$-$C_7$)-alkoxyimino, ($C_1$-$C_6$)-haloalkyl-($C_1$-$C_7$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_7$)-alkylcarbonyl, ($C_1$-$C_7$)-haloalkylcarbonyl, ($C_1$-$C_7$)-alkylcarbonyloxy, ($C_1$-$C_7$)-alkoxycarbonyl, ($C_1$-$C_7$)-haloalkoxycarbonyl, aminocarbonyl, ($C_1$-$C_7$)-alkylaminocarbonyl, di-($C_1$-$C_7$)-alkylaminocarbonyl, ($C_2$-$C_7$)-alkenylaminocarbonyl, di-($C_2$-$C_7$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylsulfonylamino, $C(O)NR^8R^9$, $C(S)NR^8R^9$, with the proviso that $R^3$, $R^4$, $R^5$ and $R^6$ do not simultaneously represent hydrogen, or $R^3$ and $R^4$, or $R^4$ and $R^5$, or $R^5$ and $R^6$ together with the atoms to which they are attached form a saturated or unsaturated, optionally ($C_1$-$C_6$)-alkyl- or halogen-substituted 5- to 6-membered ring which may optionally contain one or two heteroatoms from the group consisting of O and S (where the heteroatoms must not be directly adjacent to one another) and/or may optionally contain at least one carbonyl group, $R^8$ and $R^9$ independently of one another represent hydrogen, ($C_1$-$C_6$)-alkyl, ($C_1$-$C_6$)-haloalkyl, ($C_3$-$C_8$)-cycloalkyl, $C_1$-$C_6$)-alkylthio, ($C_1$-$C_6$)-alkylsulfinyl or ($C_1$-$C_6$)-alkylsulfonyl.

DETAILED DESCRIPTION OF A PREFERRED EMBODIMENT

The compounds according to the invention may, depending on the nature of the substituents, be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixtures of these isomers.

In the case that $R^3$ is different from $R^6$ and $R^4$ is different from $R^5$, the compounds of the formula (I) may be present either as mixtures or else in the form of their pure isomers (regioisomers). Mixtures may optionally be separated by physical methods, for example by chromatographic methods.

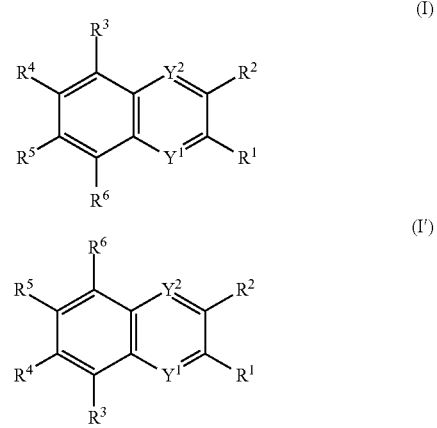

The following text will only mention in each case one of the isomers which are possible, for the sake of clarity. This includes that the compound in question may optionally be present as an isomer mixture or in the respective other isomeric form.

It has additionally been found that the compounds of the formula (I) have very good efficacy as pesticides, preferably as insecticides and/or acaricides, and additionally generally have very good plant compatibility, in particular with respect to crop plants. Moreover, it has been found that the compounds of the formula (I) have very good activity as nematicides and/or anthelmintics.

A general definition of the compounds of the invention is provided by the formula (I). Preferred substituents or ranges of the radicals given in the formulae mentioned above and below are illustrated hereinafter:

$Y^1$ and $Y^2$ independently of one another preferably represent N or $N^+$—$O^-$, $R^1$ preferably represents phenyl or hetaryl from the group Q-1 to Q-69, each of which is optionally mono- or polysubstituted by identical or different substituents:

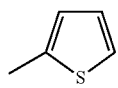
Q-1

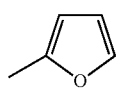
Q-2

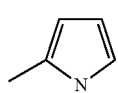
Q-3

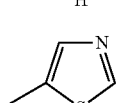
Q-4

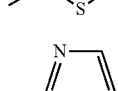
Q-5

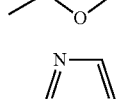
Q-6

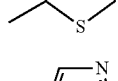
Q-7

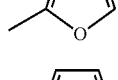
Q-8

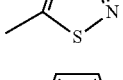
Q-9

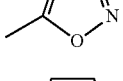
Q-10

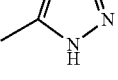
Q-11

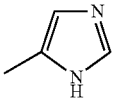
Q-12

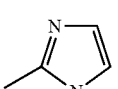

-continued

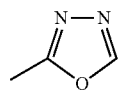
Q-13

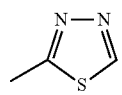
Q-14

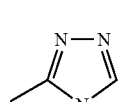
Q-15

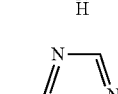
Q-16

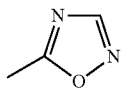
Q-17

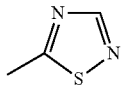
Q-18

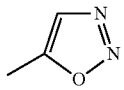
Q-19

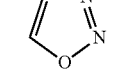
Q-20

Q-21

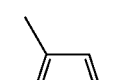
Q-22

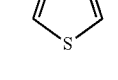
Q-23

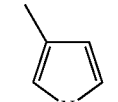
Q-24

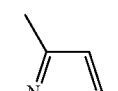
Q-25

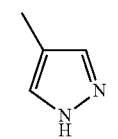

Q-26 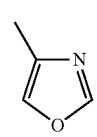
Q-27 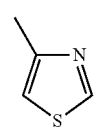
Q-28 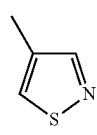
Q-29 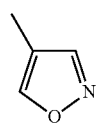
Q-30 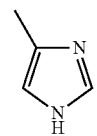
Q-31 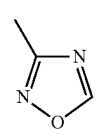
Q-32 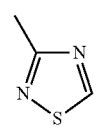
Q-33 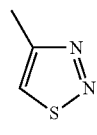
Q-34 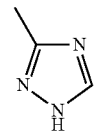
Q-35 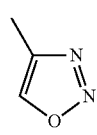
Q-36 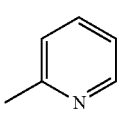
Q-37 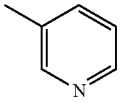
Q-38 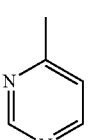
Q-39 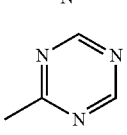
Q-40 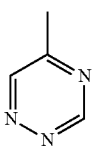
Q-41 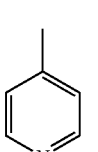
Q-42 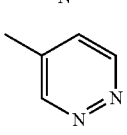
Q-43 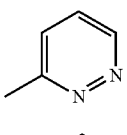
Q-44 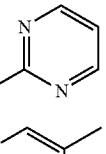
Q-45 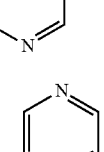
Q-46 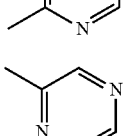
Q-47 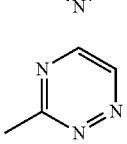
Q-48 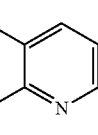
Q-49 
Q-50

-continued

Q-51 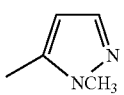

Q-52 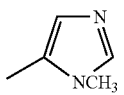

Q-53 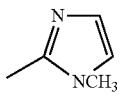

Q-54 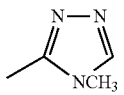

Q-55 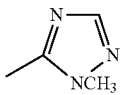

Q-56 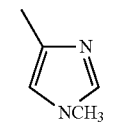

Q-57 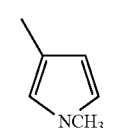

Q-58 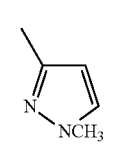

Q-59 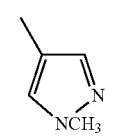

Q-60 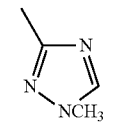

Q-61 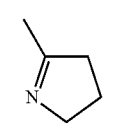

Q-62 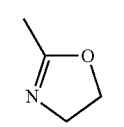

Q-63 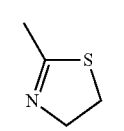

-continued

Q-64 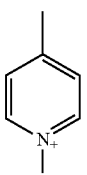

Q-65 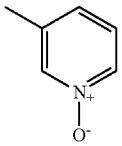

Q-66 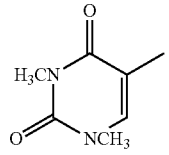

Q-67 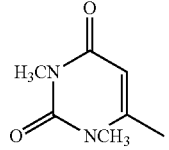

Q-68 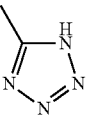

Q-69 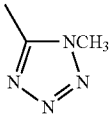

where in each case at least one carbonyl group may optionally be present (does not apply to phenyl) and/or where possible substituents are in each case as follows: cyano, halogen, nitro, acetyl, amino, ($C_1$-$C_3$)-alkyl, ($C_1$-$C_3$)-haloalkyl, ($C_1$-$C_3$)-cyanoalkyl, ($C_1$-$C_3$)-hydroxyalkyl, hydroxycarbonyl-($C_1$-$C_3$)-alkoxy, ($C_1$-$C_3$)-alkoxycarbonyl-($C_1$-$C_3$)-alkyl, ($C_1$-$C_3$)-alkoxy-($C_1$-$C_3$)-alkyl, ($C_2$-$C_3$)-alkenyl, ($C_2$-$C_3$)-haloalkenyl, ($C_2$-$C_3$)-cyanoalkenyl, ($C_2$-$C_3$)-alkynyl, ($C_2$-$C_3$)-haloalkynyl, ($C_2$-$C_3$)-cyanoalkynyl, ($C_1$-$C_3$)-alkoxy, ($C_1$-$C_3$)-haloalkoxy, ($C_1$-$C_3$)-cyanoalkoxy, ($C_1$-$C_3$)-alkoxycarbonyl-($C_1$-$C_3$)-alkoxy, ($C_1$-$C_3$)-alkoxy-($C_1$-$C_3$)-alkoxy, ($C_1$-$C_3$)-alkylhydroxyimino, ($C_1$-$C_3$)-alkoxyimino, ($C_1$-$C_3$)-alkyl-($C_1$-$C_3$)-alkoxyimino, ($C_1$-$C_3$)-haloalkyl-($C_1$-$C_3$)-alkoxyimino, ($C_1$-$C_3$)-alkylthio, ($C_1$-$C_3$)-haloalkylthio, ($C_1$-$C_3$)-alkoxy-($C_1$-$C_3$)-alkylthio, ($C_1$-$C_3$)-alkylthio-($C_1$-$C_3$)-alkyl, ($C_1$-$C_3$)-alkylsulfinyl, ($C_1$-$C_3$)-haloalkylsulfinyl, ($C_1$-$C_3$)-alkoxy-($C_1$-$C_3$)-alkylsulfinyl, ($C_1$-$C_3$)-alkylsulfinyl-($C_1$-$C_3$)-alkyl, ($C_1$-$C_3$)-alkylsulfonyl, ($C_1$-$C_3$)-haloalkylsulfonyl, ($C_1$-$C_3$)-alkoxy-($C_1$-$C_3$)-alkylsulfonyl, ($C_1$-$C_3$)-alkylsulfonyl-($C_1$-$C_3$)-alkyl, ($C_1$-$C_3$)-alkylsulfonyloxy, ($C_1$-$C_3$)-alkylcarbonyl, ($C_1$-$C_3$)-haloalkylcarbonyl, ($C_1$-$C_3$)-alkylcarbonyloxy, ($C_1$-$C_3$)-alkoxycarbonyl, ($C_1$-$C_3$)-haloalkoxycarbonyl, aminocarbonyl, ($C_1$-$C_3$)-alkylaminocarbonyl, di-($C_1$-

$C_3$)-alkylaminocarbonyl, ($C_2$-$C_3$)-alkenylaminocarbonyl, di-($C_2$-$C_3$)-alkenylaminocarbonyl, ($C_3$-$C_6$)-cycloalkylaminocarbonyl, ($C_1$-$C_3$)-alkylsulfonylamino, ($C_1$-$C_3$)-alkylamino, aminosulfonyl, ($C_1$-$C_3$)-alkylaminosulfonyl, di-($C_1$-$C_3$)-alkylaminosulfonyl, ($C_1$-$C_3$)-alkylsulfoximino, aminothiocarbonyl, ($C_1$-$C_3$)-alkylaminothiocarbonyl, di-($C_1$-$C_3$)-alkylaminothiocarbonyl, $R^2$ preferably represents hydrogen, cyano, halogen, nitro, acetyl, amino, tri-($C_1$-$C_3$)-alkylsilyl, cyclo-($C_3$-$C_6$)-alkyl, ($C_1$-$C_3$)-alkyl, ($C_1$-$C_3$)-haloalkyl, ($C_1$-$C_3$)-cyanoalkyl, ($C_1$-$C_3$)-hydroxyalkyl, hydroxycarbonyl-($C_1$-$C_3$)-alkoxy, ($C_1$-$C_3$)-alkoxycarbonyl-($C_1$-$C_3$)-alkyl, ($C_1$-$C_3$)-alkoxy-($C_1$-$C_3$)-alkyl, ($C_2$-$C_3$)-alkenyl, ($C_2$-$C_3$)-haloalkenyl, ($C_2$-$C_3$)-cyanoalkenyl, ($C_2$-$C_3$)-alkynyl, ($C_2$-$C_3$)-haloalkynyl, ($C_2$-$C_3$)-cyanoalkynyl, ($C_1$-$C_3$)-alkoxy, ($C_1$-$C_3$)-haloalkoxy, ($C_1$-$C_3$)-cyanoalkoxy, ($C_1$-$C_3$)-alkoxycarbonyl-($C_1$-$C_3$)-alkoxy, ($C_1$-$C_3$)-alkoxy-($C_1$-$C_3$)-alkoxy, ($C_1$-$C_3$)-alkylhydroxyimino, ($C_1$-$C_3$)-alkoxyimino, ($C_1$-$C_3$)-alkyl-($C_1$-$C_3$)-alkoxyimino, ($C_1$-$C_3$)-haloalkyl-($C_1$-$C_3$)-alkoxyimino, ($C_1$-$C_3$)-alkylthio, ($C_1$-$C_3$)-haloalkylthio, ($C_1$-$C_3$)-alkoxy-($C_1$-$C_3$)-alkylthio, ($C_1$-$C_3$)-alkylthio-($C_1$-$C_3$)-alkyl, ($C_1$-$C_3$)-alkylsulfinyl, ($C_1$-$C_3$)-haloalkylsulfinyl, ($C_1$-$C_3$)-alkoxy-($C_1$-$C_3$)-alkylsulfinyl, ($C_1$-$C_3$)-alkylsulfinyl-($C_1$-$C_3$)-alkyl, ($C_1$-$C_3$)-alkylsulfonyl, ($C_1$-$C_3$)-haloalkylsulfonyl, ($C_1$-$C_3$)-alkoxy-($C_1$-$C_3$)-alkylsulfonyl, ($C_1$-$C_3$)-alkylsulfonyl-($C_1$-$C_3$)-alkyl, ($C_1$-$C_3$)-alkylsulfonyloxy, ($C_1$-$C_3$)-alkylcarbonyl, ($C_1$-$C_3$)-haloalkylcarbonyl, ($C_1$-$C_3$)-alkylcarbonyloxy, ($C_1$-$C_3$)-alkoxycarbonyl, ($C_1$-$C_3$)-haloalkoxycarbonyl, aminocarbonyl, ($C_1$-$C_3$)-alkylaminocarbonyl, di-($C_1$-$C_3$)-alkylaminocarbonyl, ($C_2$-$C_3$)-alkenylaminocarbonyl, di-($C_2$-$C_3$)-alkenylaminocarbonyl, ($C_3$-$C_6$)-cycloalkylaminocarbonyl, ($C_1$-$C_3$)-alkylsulfonylamino, ($C_1$-$C_3$)-alkylamino, aminosulfonyl, ($C_1$-$C_3$)-alkylaminosulfonyl, di-($C_1$-$C_3$)-alkylaminosulfonyl, ($C_1$-$C_3$)-alkylsulfoximino, aminothiocarbonyl, ($C_1$-$C_3$)-alkylaminothiocarbonyl, di-($C_1$-$C_3$)-alkylaminothiocarbonyl, represents phenyl or hetaryl from the group Q-1 to Q-69, each of which is optionally mono- or polysubstituted by identical or different substituents, where at least one carbonyl group may optionally be present (does not apply to phenyl) and/or where possible substituents are in each case as follows: cyano, halogen, amino, ($C_1$-$C_3$)-alkyl, ($C_1$-$C_3$)-haloalkyl, ($C_1$-$C_3$)-cyanoalkyl, ($C_1$-$C_3$)-hydroxyalkyl, hydroxycarbonyl-($C_1$-$C_3$)-alkoxy, ($C_1$-$C_3$)-alkoxycarbonyl-($C_1$-$C_3$)-alkyl, ($C_1$-$C_3$)-alkoxy-($C_1$-$C_3$)-alkyl, ($C_2$-$C_3$)-alkenyl, ($C_2$-$C_3$)-haloalkenyl, ($C_2$-$C_3$)-cyanoalkenyl, ($C_2$-$C_3$)-alkynyl, ($C_2$-$C_3$)-haloalkynyl, ($C_2$-$C_3$)-cyanoalkynyl, ($C_1$-$C_3$)-alkoxy, ($C_1$-$C_3$)-haloalkoxy, ($C_1$-$C_3$)-cyanoalkoxy, ($C_1$-$C_3$)-alkoxycarbonyl-($C_1$-$C_3$)-alkoxy, ($C_1$-$C_3$)-alkoxy-($C_1$-$C_3$)-alkoxy, ($C_1$-$C_3$)-alkylhydroxyimino, ($C_1$-$C_3$)-alkoxyimino, ($C_1$-$C_3$)-alkyl-($C_1$-$C_3$)-alkoxyimino, ($C_1$-$C_3$)-haloalkyl-($C_1$-$C_3$)-alkoxyimino, ($C_1$-$C_3$)-alkylthio, ($C_1$-$C_3$)-haloalkylthio, ($C_1$-$C_3$)-alkoxy-($C_1$-$C_3$)-alkylthio, ($C_1$-$C_3$)-alkylthio-($C_1$-$C_3$)-alkyl, ($C_1$-$C_3$)-alkylsulfinyl, ($C_1$-$C_3$)-haloalkylsulfinyl, ($C_1$-$C_3$)-alkoxy-($C_1$-$C_3$)-alkylsulfinyl, ($C_1$-$C_3$)-alkylsulfinyl-($C_1$-$C_3$)-alkyl, ($C_1$-$C_3$)-alkylsulfonyl, ($C_1$-$C_3$)-haloalkylsulfonyl, ($C_1$-$C_3$)-alkoxy-($C_1$-$C_3$)-alkylsulfonyl, ($C_1$-$C_3$)-alkylsulfonyl-($C_1$-$C_3$)-alkyl, ($C_1$-$C_3$)-alkylsulfonyloxy, ($C_1$-$C_3$)-alkylcarbonyl, ($C_1$-$C_3$)-haloalkylcarbonyl, ($C_1$-$C_3$)-alkylcarbonyloxy, ($C_1$-$C_3$)-alkoxycarbonyl, ($C_1$-$C_3$)-haloalkoxycarbonyl, aminocarbonyl, ($C_1$-$C_3$)-alkylaminocarbonyl, di-($C_1$-$C_3$)-alkylaminocarbonyl, ($C_2$-$C_3$)-alkenylaminocarbonyl, di-($C_2$-$C_3$)-alkenylaminocarbonyl, ($C_3$-$C_6$)-cycloalkylaminocarbonyl, ($C_1$-$C_3$)-alkylsulfonylamino, ($C_1$-$C_3$)-alkylamino, aminosulfonyl, ($C_1$-$C_3$)-alkylaminosulfonyl, di-($C_1$-$C_3$)-alkylaminosulfonyl, ($C_1$-$C_3$)-alkylsulfoximino, aminothiocarbonyl, ($C_1$-$C_3$)-alkylaminothiocarbonyl, di-($C_1$-$C_3$)-alkylaminothiocarbonyl, $R^3$, $R^4$, $R^5$ and $R^6$ independently of one another preferably represent hydrogen, halogen, cyano, ($C_1$-$C_3$)-alkyl, ($C_1$-$C_3$)-haloalkyl, ($C_1$-$C_3$)-cyanoalkyl, ($C_1$-$C_3$)-hydroxyalkyl, hydroxycarbonyl-($C_1$-$C_3$)-alkoxy, ($C_1$-$C_3$)-alkoxycarbonyl-($C_1$-$C_3$)-alkyl, ($C_1$-$C_3$)-alkoxy-($C_1$-$C_3$)-alkyl, ($C_2$-$C_3$)-alkenyl, ($C_2$-$C_3$)-haloalkenyl, ($C_2$-$C_3$)-cyanoalkenyl, ($C_2$-$C_3$)-alkynyl, ($C_2$-$C_3$)-haloalkynyl, ($C_2$-$C_3$)-cyanoalkynyl, ($C_1$-$C_3$)-alkoxy, ($C_1$-$C_3$)-haloalkoxy, ($C_1$-$C_3$)-cyanoalkoxy, ($C_1$-$C_3$)-alkoxycarbonyl-($C_1$-$C_3$)-alkoxy, ($C_1$-$C_3$)-alkoxy-($C_1$-$C_3$)-alkoxy, ($C_1$-$C_3$)-alkylhydroxyimino, ($C_1$-$C_3$)-alkoxyimino, ($C_1$-$C_3$)-alkyl-($C_1$-$C_3$)-alkoxyimino, ($C_1$-$C_3$)-haloalkyl-($C_1$-$C_3$)-alkoxyimino, ($C_1$-$C_3$)-alkylthio, ($C_1$-$C_3$)-haloalkylthio, ($C_1$-$C_3$)-alkoxy-($C_1$-$C_3$)-alkylthio, ($C_1$-$C_3$)-alkylthio-($C_1$-$C_3$)-alkyl, ($C_1$-$C_3$)-alkylsulfinyl, ($C_1$-$C_3$)-haloalkylsulfinyl, ($C_1$-$C_3$)-alkoxy-($C_1$-$C_3$)-alkylsulfinyl, ($C_1$-$C_3$)-alkylsulfinyl-($C_1$-$C_3$)-alkyl, ($C_1$-$C_3$)-alkylsulfonyl, ($C_1$-$C_3$)-haloalkylsulfonyl, ($C_1$-$C_3$)-alkoxy-($C_1$-$C_3$)-alkylsulfonyl, ($C_1$-$C_3$)-alkylsulfonyl-($C_1$-$C_3$)-alkyl, ($C_1$-$C_3$)-alkylsulfonyloxy, ($C_1$-$C_3$)-alkylcarbonyl, ($C_1$-$C_3$)-haloalkylcarbonyl, ($C_1$-$C_3$)-alkylcarbonyloxy, ($C_1$-$C_3$)-alkoxycarbonyl, ($C_1$-$C_3$)-haloalkoxycarbonyl, aminocarbonyl, ($C_1$-$C_3$)-alkylaminocarbonyl, di-($C_1$-$C_3$)-alkylaminocarbonyl, ($C_2$-$C_3$)-alkenylaminocarbonyl, di-($C_2$-$C_3$)-alkenylaminocarbonyl, ($C_3$-$C_6$)-cycloalkylaminocarbonyl, ($C_1$-$C_3$)-alkylsulfonylamino, ($C_1$-$C_3$)-alkylamino, aminosulfonyl, ($C_1$-$C_3$)-alkylaminosulfonyl, di-($C_1$-$C_3$)-alkylaminosulfonyl, ($C_1$-$C_3$)-alkylsulfoximino, aminothiocarbonyl, ($C_1$-$C_3$)-alkylaminothiocarbonyl, di-($C_1$-$C_3$)-alkylaminothiocarbonyl, C(O)NR$^8$R$^9$, C(S)NR$^8$R$^9$, with the proviso that $R^3$, $R^4$, $R^5$ and $R^6$ do not simultaneously represent hydrogen, or $R^3$ and $R^4$, or $R^4$ and $R^5$, or $R^5$ and $R^6$ together with the atoms to which they are attached preferably form a saturated, optionally halogen- or ($C_1$-$C_3$)-alkyl-substituted 5- or 6-membered ring which optionally contains one or two oxygen atoms (where the heteroatoms must not be directly adjacent to one another), $R^8$ and $R^9$ independently of one another preferably represent hydrogen, ($C_1$-$C_3$)-alkyl, ($C_3$-$C_6$)-cycloalkyl, ($C_1$-$C_3$)-haloalkyl, ($C_1$-$C_3$)-alkylsulfinyl or ($C_1$-$C_3$)-alkylsulfonyl.

$Y^1$ and $Y^2$ independently of one another particularly preferably represent N or N$^+$—O$^-$, $R^1$ particularly preferably represents phenyl or hetaryl from the group Q-1, Q-22, Q-36, Q-37, Q-41, Q-44, Q-45, Q-51, Q-64, Q-66, Q-67, each of which is optionally mono- or disubstituted by identical or different substituents, possible substituents being in each case: cyano, halogen, ($C_1$-$C_3$)-alkyl, ($C_1$-$C_3$)-haloalkyl, ($C_2$-$C_3$)-alkenyl, ($C_2$-$C_3$)-haloalkenyl, ($C_1$-$C_3$)-alkoxy, ($C_1$-$C_3$)-haloalkoxy, ($C_1$-$C_3$)-alkylsulfinyl, ($C_1$-$C_3$)-haloalkylsulfinyl, ($C_1$-$C_3$)-alkylsulfonyl, ($C_1$-$C_3$)-haloalkylsulfonyl, ($C_1$-$C_3$)-alkylthio, $R^2$ particularly preferably represents hydrogen, cyano, halogen, ($C_1$-$C_3$)-alkyl, ($C_1$-$C_3$)-haloalkyl, ($C_2$-$C_3$)-alkenyl, ($C_2$-$C_3$)-haloalkenyl, ($C_2$-$C_3$)-alkynyl, ($C_2$-$C_3$)-haloalkynyl, ($C_1$-$C_3$)-alkoxy, ($C_1$-$C_3$)-haloalkoxy, ($C_1$-$C_3$)-alkylsulfinyl, ($C_1$-$C_3$)-haloalkylsulfinyl, ($C_1$-$C_3$)-alkylsulfonyl, ($C_1$-$C_3$)-haloalkylsulfonyl or represents phenyl or hetaryl from the group Q-1, Q-22, Q-36, Q-37, Q-41, Q-44, Q-45, Q-51, Q-64, Q-66, Q-67, each of which is optionally mono- or disubstituted by identical or different substituents, possible substituents being in each case: cyano, halogen, $(C_1-C_3)$-alkyl, $(C_1-C_3)$-haloalkyl, $(C_2-C_3)$-alkenyl, $(C_2-C_3)$-haloalkenyl, $(C_1-C_3)$-alkoxy, $(C_1-C_3)$-haloalkoxy, $(C_1-C_3)$-alkylsulfinyl, $(C_1-C_3)$-haloalkylsulfinyl, $(C_1-C_3)$-alkylsulfonyl, $(C_1-C_3)$-haloalkylsulfonyl, $(C_1-C_3)$-alkylthio, $R^3$, $R^4$, $R^5$ and $R^6$ independently of one another particularly preferably represent hydrogen, cyano, halogen, $(C_1-C_3)$-alkyl, $(C_1-C_3)$-haloalkyl, $(C_2-C_3)$-alkenyl, $(C_2-C_3)$-haloalkenyl, $(C_2-C_3)$-alkynyl, $(C_2-C_3)$-haloalkynyl, $(C_1-C_3)$-alkoxy, $(C_1-C_3)$-haloalkoxy, $(C_1-C_3)$-alkylsulfinyl, $(C_1-C_3)$-haloalkylsulfinyl, $(C_1-C_3)$-alkylsulfonyl, $(C_1-C_3)$-haloalkylsulfonyl, with the proviso that $R^3$, $R^4$, $R^5$ and $R^6$ do not simultaneously represent hydrogen or $R^3$ and $R^4$, or $R^4$ and $R^5$, or $R^5$ and $R^6$ together with the atoms to which they are attached particularly preferably form a saturated, optionally fluorine-, chlorine- or $(C_1-C_3)$-alkyl-substituted 5-membered ring which optionally contains one or two oxygen atoms (where the heteroatoms must not be directly adjacent to one another).

$Y^1$ and $Y^2$ independently of one another very particularly preferably represent N or $N^+-O^-$, $R^1$ very particularly preferably represents phenyl or hetaryl from the group group Q-1, Q-22, Q-36, Q-37, Q-41, Q-45, Q-51, Q-64, each of which is optionally mono- or disubstituted by identical or different substituents, possible substituents being: methyl, ethyl, chlorine, fluorine, cyano, difluoromethyl, trifluoromethyl, $SCH_3$, $SOCH_3$, $SO_2CH_3$, $SC_2H_5$, $SOC_2H_5$, $SO_2C_2H_5$, methoxy, ethoxy, difluoromethoxy, trifluoromethoxy or 2,2,2-trifluoroethoxy, $R^2$ very particularly preferably represents hydrogen, fluorine, chlorine, bromine, methyl, ethyl, difluoromethyl, trifluoromethyl, represents in each case optionally chlorine-substituted phenyl or hetaryl from group Q-41, $R^3$ very particularly preferably represents hydrogen, $R^4$ very particularly preferably represents hydrogen, chlorine, fluorine, cyano, $SO_2CH_3$, $SO_2C_2H_5$, trifluoromethyl, difluoromethyl, difluoromethoxy, trifluoromethoxy or 2,2,2-trifluoroethoxy, $R^5$ very particularly preferably represents hydrogen, chlorine, fluorine, cyano, $SO_2CH_3$, $SO_2C_2H_5$, trifluoromethyl, difluoromethyl, difluoromethoxy, trifluoromethoxy or 2,2,2-trifluoroethoxy, $R^6$ very particularly preferably represents hydrogen, with the proviso that $R^3$, $R^4$, $R^5$ and $R^6$ do not simultaneously represent hydrogen or $R^3$ and $R^4$, or $R^4$ and $R^5$, or $R^5$ and $R^6$ very particularly preferably form the following 5-membered ring

which is optionally mono- or disubstituted by fluorine.

$Y^1$ and $Y^2$ most preferably each represent N, $R^1$ most preferably represents hetaryl from the group Q-1 or Q-22, each of which is optionally monosubstituted by methyl, represents hetaryl from the group Q-36 which is optionally mono- or disubstituted (differently) by methyl, ethyl, chlorine, fluorine, trifluoromethyl, $SCH_3$, $SC_2H_5$, $SOC_2H_5$, $SO_2CH_3$, $SO_2C_2H_5$, represents hetaryl from the group Q-37 which is optionally monosubstituted by ethoxy, represents hetaryl from the group Q-41 which is optionally monosubstituted by methyl, ethyl, chlorine, methoxy, represents hetaryl from the group Q-45 or Q-51, represents phenyl which is optionally mono- or disubstituted (differently) by methyl, ethyl, chlorine, fluorine, trifluoromethyl, $SCH_3$, $SC_2H_5$, $SOC_2H_5$, $SO_2CH_3$, $SO_2C_2H_5$, $R^2$ most preferably represents hydrogen, chlorine, methyl, represents hetaryl from group Q-41 or represents phenyl which is optionally monosubstituted by chlorine, $R^3$ most preferably represents hydrogen, $R^4$ most preferably represents hydrogen, chlorine, cyano or trifluoromethyl, $R^5$ most preferably represents hydrogen, chlorine, trifluoromethyl or $SO_2CH_3$, or $R^4$ and $R^5$ together most preferably represent $-O-CF_2-O-$, $R^6$ most preferably represents hydrogen, with the proviso that $R^3$, $R^4$, $R^5$ and $R^6$ do not simultaneously represent hydrogen.

$Y^1$ also most preferably represents N and $Y^2$ also most preferably represents $N^+-O^-$, $R^1$ also most preferably represents phenyl which is optionally mono- or disubstituted (differently) by trifluoromethyl, fluorine or methyl or represents hetaryl from the group Q-64 which is optionally monosubstituted by methyl, $R^2$ also most preferably represents hydrogen, $R^3$ also most preferably represents hydrogen, $R^4$ also most preferably represents hydrogen or trifluoromethyl, $R^5$ also most preferably represents hydrogen or trifluoromethyl or $R^4$ and $R^5$ together also most preferably represent $-O-CF_2-O-$, $R^6$ also most preferably represents hydrogen, with the proviso that $R^3$, $R^4$, $R^5$ and $R^6$ do not simultaneously represent hydrogen.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Most preferred in accordance with the invention are the compounds of the formula (I) which contain a combination of the meanings listed above as being most preferred.

Particular emphasis is given to compounds of the formula (I) in which $Y^1$ and $Y^2$ each represent N.

In a further preferred embodiment, the invention relates to compounds of the formula (I-A)

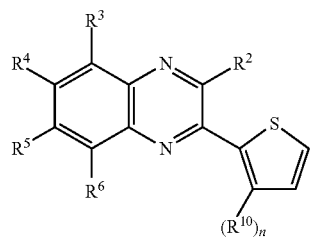

In a further preferred embodiment, the invention relates to compounds of the formula (I-B)

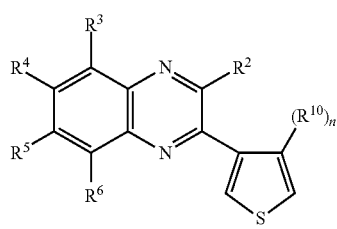

In a further preferred embodiment, the invention relates to compounds of the formula (I-C)

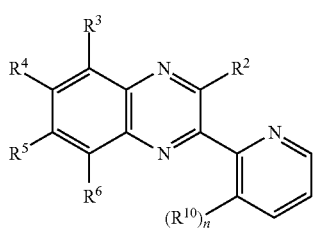

In a further preferred embodiment, the invention relates to compounds of the formula (I-D)

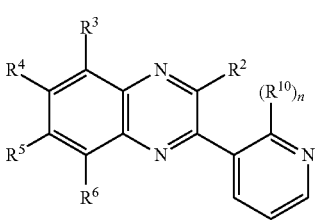

In a further preferred embodiment, the invention relates to compounds of the formula (I-E)

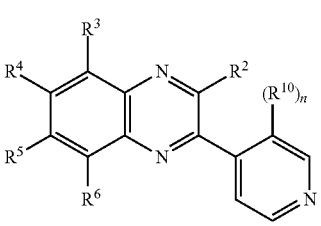

In a further preferred embodiment, the invention relates to compounds of the formula (I-F)

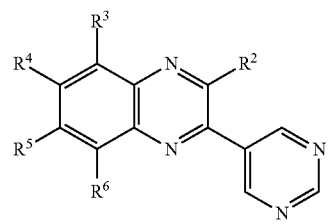

In a further preferred embodiment, the invention relates to compounds of the formula (I-G)

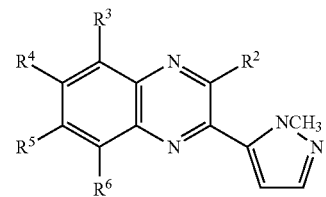

In a further preferred embodiment, the invention relates to compounds of the formula (I-H)

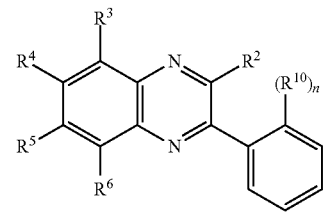

In a further preferred embodiment, the invention relates to compounds of the formula (I-I)

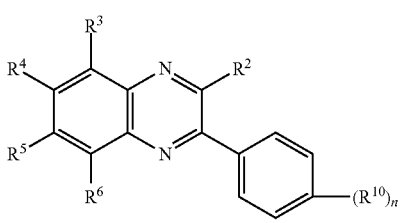

In a further preferred embodiment, the invention relates to compounds of the formula (I-J)

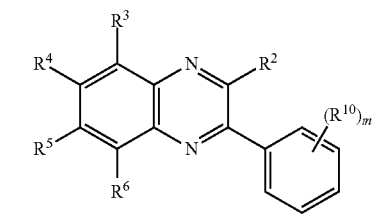

In a further preferred embodiment, the invention relates to compounds of the formula (I-K)

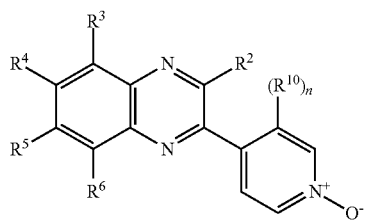

In the formulae (I-A) to (I-K), the radicals $R^2$, $R^3$, $R^4$, $R^5$ and $R^6$ have the meanings given above and $R^{10}$ preferably represents cyano, halogen, nitro, acetyl, amino, ($C_1$-$C_3$)-alkyl, ($C_1$-$C_3$)-haloalkyl, ($C_1$-$C_3$)-cyanoalkyl, ($C_1$-$C_3$)-hydroxyalkyl, hydroxycarbonyl-($C_1$-$C_3$)-alkoxy, ($C_1$-$C_3$)-alkoxycarbonyl-($C_1$-$C_3$)-alkyl, ($C_1$-$C_3$)-alkoxy-($C_1$-$C_3$)-alkyl, ($C_2$-$C_3$)-alkenyl, ($C_2$-$C_3$)-haloalkenyl, ($C_2$-$C_3$)-cyanoalkenyl, ($C_2$-$C_3$)-alkynyl, ($C_2$-$C_3$)-haloalkynyl, ($C_2$-$C_3$)-cyanoalkynyl, ($C_1$-$C_3$)-alkoxy, ($C_1$-$C_3$)-haloalkoxy, ($C_1$-$C_3$)-cyanoalkoxy, ($C_1$-$C_3$)-alkoxycarbonyl-($C_1$-$C_3$)-alkoxy, ($C_1$-$C_3$)-alkoxy-($C_1$-$C_3$)-alkoxy, ($C_1$-$C_3$)-alkylhydroxyimino, ($C_1$-$C_3$)-alkoxyimino, ($C_1$-$C_3$)-alkyl-($C_1$-$C_3$)-alkoxyimino, ($C_1$-$C_3$)-haloalkyl-($C_1$-$C_3$)-alkoxyimino, ($C_1$-$C_3$)-alkylthio, ($C_1$-$C_3$)-haloalkylthio, ($C_1$-$C_3$)-alkoxy-($C_1$-$C_3$)-alkylthio, ($C_1$-$C_3$)-alkylthio-($C_1$-$C_3$)-alkyl, ($C_1$-$C_3$)-alkylsulfinyl, ($C_1$-$C_3$)-haloalkylsulfinyl, ($C_1$-$C_3$)-alkoxy-($C_1$-$C_3$)-alkylsulfinyl, ($C_1$-$C_3$)-alkylsulfinyl-($C_1$-$C_3$)-alkyl, ($C_1$-$C_3$)-alkylsulfonyl, ($C_1$-$C_3$)-haloalkylsulfonyl, ($C_1$-$C_3$)-alkoxy-($C_1$-$C_3$)-alkylsulfonyl, ($C_1$-$C_3$)-alkylsulfonyl-($C_1$-$C_3$)-alkyl, ($C_1$-$C_3$)-alkylsulfonyloxy, ($C_1$-$C_3$)-alkylcarbonyl, ($C_1$-$C_3$)-haloalkylcarbonyl, ($C_1$-$C_3$)-alkylcarbonyloxy, ($C_1$-$C_3$)-alkoxycarbonyl, ($C_1$-$C_3$)-haloalkoxycarbonyl, aminocarbonyl, ($C_1$-$C_3$)-alkylaminocarbonyl, di-($C_1$-$C_3$)-alkylaminocarbonyl, ($C_2$-$C_3$)-alkenylaminocarbonyl, di-($C_2$-$C_3$)-alkenylaminocarbonyl, ($C_3$-$C_6$)-cycloalkylaminocarbonyl, ($C_1$-$C_3$)-alkylsulfonylamino, ($C_1$-$C_3$)-alkylamino, aminosulfonyl, ($C_1$-$C_3$)-alkylaminosulfonyl, di-($C_1$-$C_3$)-alkylaminosulfonyl, ($C_1$-$C_3$)-alkylsulfoximino, aminothiocarbonyl, ($C_1$-$C_3$)-alkylaminothiocarbonyl, di-($C_1$-$C_3$)-alkylaminothiocarbonyl, n represents 0 or 1, m represents 0, 1 or 2, $R^{10}$ particularly preferably represents cyano, halogen, ($C_1$-$C_3$)-alkyl, ($C_1$-$C_3$)-haloalkyl, ($C_2$-$C_3$)-alkenyl, ($C_2$-$C_3$)-haloalkenyl, ($C_1$-$C_3$)-alkoxy, ($C_1$-$C_3$)-haloalkoxy, ($C_1$-$C_3$)-alkylsulfinyl, ($C_1$-$C_3$)-haloalkylsulfinyl, ($C_1$-$C_3$)-alkylsulfonyl, ($C_1$-$C_3$)-haloalkylsulfonyl, ($C_1$-$C_3$)-alkylthio, n represents 0 or 1, m represents 0, 1 or 2, $R^{10}$ very particularly preferably represents methyl, ethyl, chlorine, fluorine, cyano, difluoromethyl, trifluoromethyl, $SCH_3$, $SOCH_3$, $SO_2CH_3$, $SC_2H_5$, $SOC_2H_5$, $SO_2C_2H_5$, methoxy, ethoxy, difluoromethoxy, trifluoromethoxy or 2,2,2-trifluoroethoxy, n represents 0 or 1, m represents 0, 1 or 2, $R^{10}$ most preferably represents methyl, ethyl, chlorine, fluorine, trifluoromethyl, $SCH_3$, $SO_2CH_3$, $SC_2H_5$, $SOC_2H_5$, $SO_2C_2H_5$, methoxy or ethoxy, n represents 0 or 1, m represents 0, 1 or 2.

Emphasis also is given to compounds of the formula (I-L)

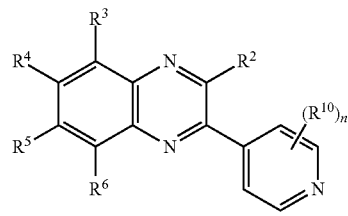

in which $R^2$, $R^3$, $R^4$, $R^5$, $R^6$, $R^{10}$ and n have the following meanings:

$R^2$ preferably represents hydrogen, cyano, halogen, nitro, acetyl, amino, tri-($C_1$-$C_3$)-alkylsilyl, cyclo-($C_3$-$C_6$)-alkyl, ($C_1$-$C_3$)-alkyl, ($C_1$-$C_3$)-haloalkyl, ($C_1$-$C_3$)-cyanoalkyl, ($C_1$-$C_3$)-hydroxyalkyl, hydroxycarbonyl-($C_1$-$C_3$)-alkoxy, ($C_1$-$C_3$)-alkoxycarbonyl-($C_1$-$C_3$)-alkyl, ($C_1$-$C_3$)-alkoxy-($C_1$-$C_3$)-alkyl, ($C_2$-$C_3$)-alkenyl, ($C_2$-$C_3$)-haloalkenyl, ($C_2$-$C_3$)-cyanoalkenyl, ($C_2$-$C_3$)-alkynyl, ($C_2$-$C_3$)-haloalkynyl, ($C_2$-$C_3$)-cyanoalkynyl, ($C_1$-$C_3$)-alkoxy, ($C_1$-$C_3$)-haloalkoxy, ($C_1$-$C_3$)-cyanoalkoxy, ($C_1$-$C_3$)-alkoxycarbonyl-($C_1$-$C_3$)-alkoxy, ($C_1$-$C_3$)-alkoxy-($C_1$-$C_3$)-alkoxy, ($C_1$-$C_3$)-alkylhydroxyimino, ($C_1$-$C_3$)-alkoxyimino, ($C_1$-$C_3$)-alkyl-($C_1$-$C_3$)-alkoxyimino, ($C_1$-$C_3$)-haloalkyl-($C_1$-$C_3$)-alkoxyimino, ($C_1$-$C_3$)-alkylthio, ($C_1$-$C_3$)-haloalkylthio, ($C_1$-$C_3$)-alkoxy-($C_1$-$C_3$)-alkylthio, ($C_1$-$C_3$)-alkylthio-($C_1$-$C_3$)-alkyl, ($C_1$-$C_3$)-alkylsulfinyl, ($C_1$-$C_3$)-haloalkylsulfinyl, ($C_1$-$C_3$)-alkoxy-($C_1$-$C_3$)-alkylsulfinyl, ($C_1$-$C_3$)-alkylsulfinyl-($C_1$-$C_3$)-alkyl, ($C_1$-$C_3$)-alkylsulfonyl, ($C_1$-$C_3$)-haloalkylsulfonyl, ($C_1$-$C_3$)-alkoxy-($C_1$-$C_3$)-alkylsulfonyl, ($C_1$-$C_3$)-alkylsulfonyl-($C_1$-$C_3$)-alkyl, ($C_1$-$C_3$)-alkylsulfonyloxy, ($C_1$-$C_3$)-alkylcarbonyl, ($C_1$-$C_3$)-haloalkylcarbonyl, ($C_1$-$C_3$)-alkylcarbonyloxy, ($C_1$-$C_3$)-alkoxycarbonyl, ($C_1$-$C_3$)-haloalkoxycarbonyl, aminocarbonyl, ($C_1$-$C_3$)-alkylaminocarbonyl, di-($C_1$-$C_3$)-alkylaminocarbonyl, ($C_2$-$C_3$)-alkenylaminocarbonyl, di-($C_2$-$C_3$)-alkenylaminocarbonyl, ($C_3$-$C_6$)-cycloalkylaminocarbonyl, ($C_1$-$C_3$)-alkylsulfonylamino, ($C_1$-$C_3$)-alkylamino, aminosulfonyl, ($C_1$-$C_3$)-alkylaminosulfonyl, di-($C_1$-$C_3$)-alkylaminosulfonyl, ($C_1$-$C_3$)-alkylsulfoximino, aminothiocarbonyl, ($C_1$-$C_3$)-alkylaminothiocarbonyl, di-($C_1$-$C_3$)-alkylaminothiocarbonyl, represents phenyl or hetaryl from the group Q-1 to Q-69, each of which is optionally mono- or polysubstituted by identical or different substituents:

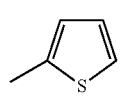 Q-1

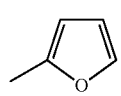 Q-2

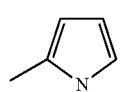 Q-3

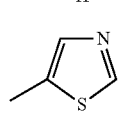 Q-4

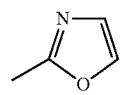 Q-5
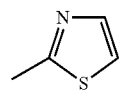 Q-6
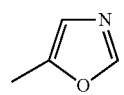 Q-7
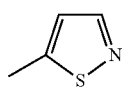 Q-8
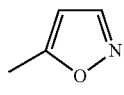 Q-9
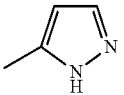 Q-10
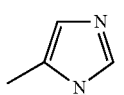 Q-11
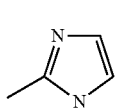 Q-12
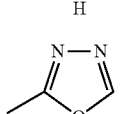 Q-13
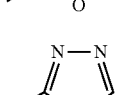 Q-14
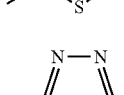 Q-15
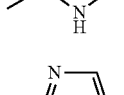 Q-16
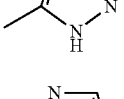 Q-17
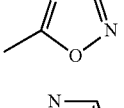 Q-18
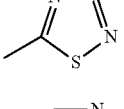 Q-19
 Q-20
 Q-21
 Q-22
 Q-23
 Q-24
 Q-25
 Q-26
 Q-27
 Q-28
 Q-29
 Q-30
 Q-31

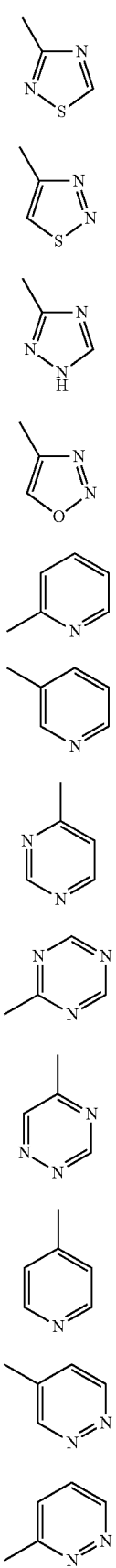
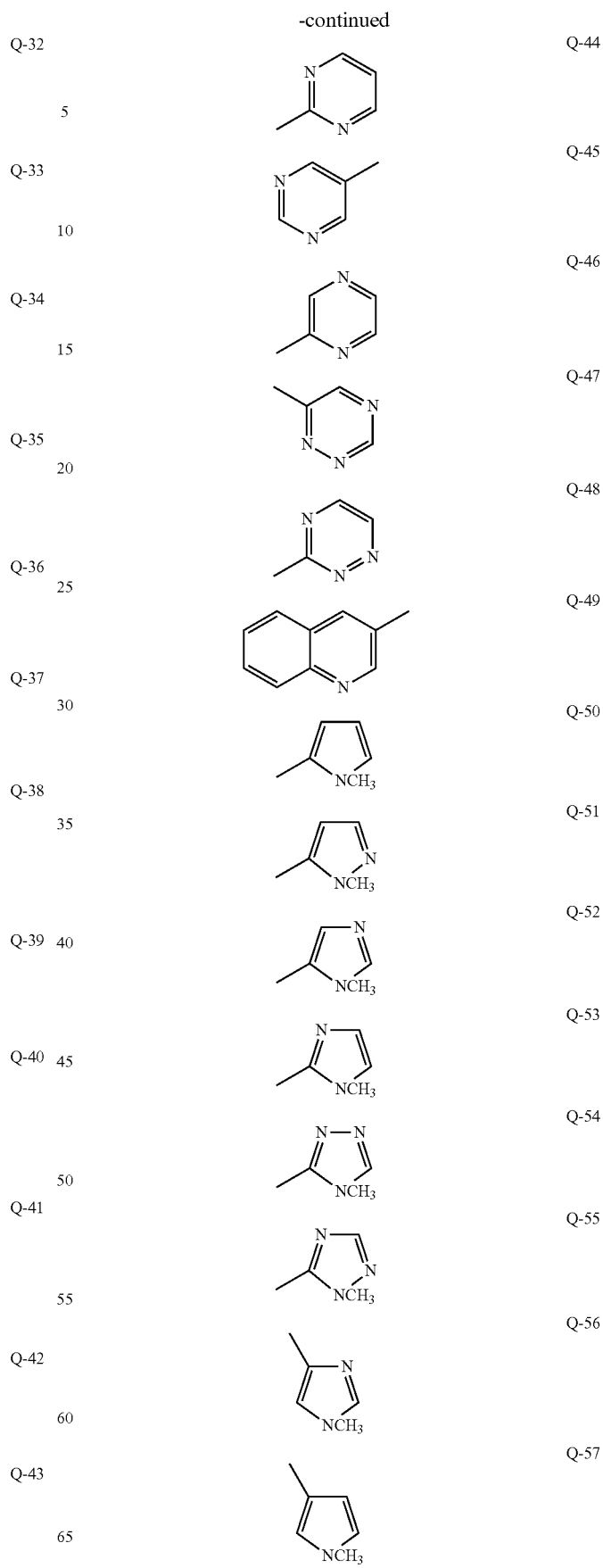

Q-58 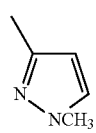

Q-59 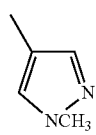

Q-60 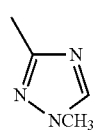

Q-61 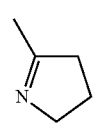

Q-62 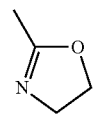

Q-63 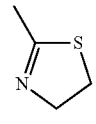

Q-64 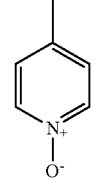

Q-65 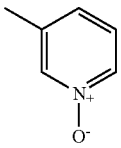

Q-66 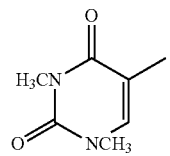

Q-67 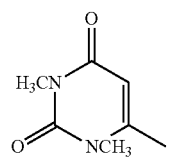

Q-68 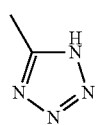

Q-69 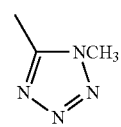

where at least one carbonyl group may optionally be present (does not apply to phenyl) and/or where possible substituents are in each case as follows: cyano, halogen, amino, $(C_1-C_3)$-alkyl, $(C_1-C_3)$-haloalkyl, $(C_1-C_3)$-cyanoalkyl, $(C_1-C_3)$-hydroxyalkyl, hydroxycarbonyl-$(C_1-C_3)$-alkoxy, $(C_1-C_3)$-alkoxycarbonyl-$(C_1-C_3)$-alkyl, $(C_1-C_3)$-alkoxy-$(C_1-C_3)$-alkyl, $(C_2-C_3)$-alkenyl, $(C_2-C_3)$-haloalkenyl, $(C_2-C_3)$-cyanoalkenyl, $(C_2-C_3)$-alkynyl, $(C_2-C_3)$-haloalkynyl, $(C_2-C_3)$-cyanoalkynyl, $(C_1-C_3)$-alkoxy, $(C_1-C_3)$-haloalkoxy, $(C_1-C_3)$-cyanoalkoxy, $(C_1-C_3)$-alkoxycarbonyl-$(C_1-C_3)$-alkoxy, $(C_1-C_3)$-alkoxy-$(C_1-C_3)$-alkoxy, $(C_1-C_3)$-alkylhydroxyimino, $(C_1-C_3)$-alkoxyimino, $(C_1-C_3)$-alkyl-$(C_1-C_3)$-alkoxyimino, $(C_1-C_3)$-haloalkyl-$(C_1-C_3)$-alkoxyimino, $(C_1-C_3)$-alkylthio, $(C_1-C_3)$-haloalkylthio, $(C_1-C_3)$-alkoxy-$(C_1-C_3)$-alkylthio, $(C_1-C_3)$-alkylthio-$(C_1-C_3)$-alkyl, $(C_1-C_3)$-alkylsulfinyl, $(C_1-C_3)$-haloalkylsulfinyl, $(C_1-C_3)$-alkoxy-$(C_1-C_3)$-alkylsulfinyl, $(C_1-C_3)$-alkylsulfinyl-$(C_1-C_3)$-alkyl, $(C_1-C_3)$-alkylsulfonyl, $(C_1-C_3)$-haloalkylsulfonyl, $(C_1-C_3)$-alkoxy-$(C_1-C_3)$-alkylsulfonyl, $(C_1-C_3)$-alkylsulfonyl-$(C_1-C_3)$-alkyl, $(C_1-C_3)$-alkylsulfonyloxy, $(C_1-C_3)$-alkylcarbonyl, $(C_1-C_3)$-haloalkylcarbonyl, $(C_1-C_3)$-alkylcarbonyloxy, $(C_1-C_3)$-alkoxycarbonyl, $(C_1-C_3)$-haloalkoxycarbonyl, aminocarbonyl, $(C_1-C_3)$-alkylaminocarbonyl, di-$(C_1-C_3)$-alkylaminocarbonyl, $(C_2-C_3)$-alkenylaminocarbonyl, di-$(C_2-C_3)$-alkenylaminocarbonyl, $(C_3-C_6)$-cycloalkylaminocarbonyl, $(C_1-C_3)$-alkylsulfonylamino, $(C_1-C_3)$-alkylamino, aminosulfonyl, $(C_1-C_3)$-alkylaminosulfonyl, di-$(C_1-C_3)$-alkylaminosulfonyl, $(C_1-C_3)$-alkylsulfoximino, $(C_1-C_3)$-alkylaminothiocarbonyl, di-$(C_1-C_3)$-alkylaminothiocarbonyl, $R^3$, $R^4$, $R^5$ and $R^6$ independently of one another preferably represent hydrogen, halogen, cyano, $(C_1-C_3)$-alkyl, $(C_1-C_3)$-haloalkyl, $(C_1-C_3)$-cyanoalkyl, $(C_1-C_3)$-hydroxyalkyl, hydroxycarbonyl-$(C_1-C_3)$-alkoxy, $(C_1-C_3)$-alkoxycarbonyl-$(C_1-C_3)$-alkyl, $(C_1-C_3)$-alkoxy-$(C_1-C_3)$-alkyl, $(C_2-C_3)$-alkenyl, $(C_2-C_3)$-haloalkenyl, $(C_2-C_3)$-cyanoalkenyl, $(C_2-C_3)$-alkynyl, $(C_2-C_3)$-haloalkynyl, $(C_2-C_3)$-cyanoalkynyl, $(C_1-C_3)$-alkoxy, $(C_1-C_3)$-haloalkoxy, $(C_1-C_3)$-cyanoalkoxy, $(C_1-C_3)$-alkoxycarbonyl-$(C_1-C_3)$-alkoxy, $(C_1-C_3)$-alkoxy-$(C_1-C_3)$-alkoxy, $(C_1-C_3)$-alkylhydroxyimino, $(C_1-C_3)$-alkoxyimino, $(C_1-C_3)$-alkyl-$(C_1-C_3)$-alkoxyimino, $(C_1-C_3)$-haloalkyl-$(C_1-C_3)$-alkoxyimino, $(C_1-C_3)$-alkylthio, $(C_1-C_3)$-haloalkylthio, $(C_1-C_3)$-alkoxy-$(C_1-C_3)$-alkylthio, $(C_1-C_3)$-alkylthio-$(C_1-C_3)$-alkyl, $(C_1-C_3)$-alkylsulfinyl, $(C_1-C_3)$-haloalkylsulfinyl, $(C_1-C_3)$-alkoxy-$(C_1-C_3)$-alkylsulfinyl, $(C_1-C_3)$-alkylsulfinyl-$(C_1-C_3)$-alkyl, $(C_1-C_3)$-alkylsulfonyl, $(C_1-C_3)$-haloalkylsulfonyl, $(C_1-C_3)$-alkoxy-$(C_1-C_3)$-alkylsulfonyl, $(C_1-C_3)$-alkylsulfonyl-$(C_1-C_3)$-alkyl, $(C_1-C_3)$-alkylsulfonyloxy, $(C_1-C_3)$-alkylcarbonyl, $(C_1-C_3)$-haloalkylcarbonyl, $(C_1-C_3)$-alkylcarbonyloxy, $(C_1-C_3)$-alkoxycarbonyl, $(C_1-C_3)$-haloalkoxycarbonyl, aminocarbonyl, $(C_1-C_3)$-alkylaminocarbonyl, di-$(C_1-C_3)$-alkylaminocarbonyl, $(C_2-C_3)$-alkenylaminocarbonyl, di-$(C_2-C_3)$-alkenylaminocarbonyl, $(C_3-C_6)$-cycloalkylaminocarbonyl, $(C_1-C_3)$-alkylsulfonylamino, $(C_1-C_3)$-alkylamino, aminosulfonyl, $(C_1-C_3)$-alkylaminosulfonyl, di-$(C_1-C_3)$-alkylaminosulfonyl, ($C_1$-$C_3$)-alkylsulfoximino, aminothiocarbonyl, ($C_1$-$C_3$)-alkylaminothiocarbonyl, di-($C_1$-$C_3$)-alkylaminothiocarbonyl, C(O)NR$^8$R$^9$, C(S)NR$^8$R$^9$,
with the proviso that R$^3$, R$^4$, R$^5$ and R$^6$ do not simultaneously represent hydrogen,
or R$^3$ and R$^4$, or R$^4$ and R$^5$, or R$^5$ and R$^6$ together with the atoms to which they are attached preferably form a saturated, optionally halogen- or ($C_1$-$C_3$)-alkyl-substituted 5- or 6-membered ring which optionally contains one or two oxygen atoms (where the heteroatoms must not be directly adjacent to one another),
R$^8$ and R$^9$ independently of one another preferably represent hydrogen, ($C_1$-$C_3$)-alkyl, ($C_3$-$C_6$)-cycloalkyl, ($C_1$-$C_3$)-haloalkyl, ($C_1$-$C_3$)-alkylsulfinyl or ($C_1$-$C_3$)-alkylsulfonyl,
R$^{10}$ preferably represents cyano, halogen, nitro, acetyl, amino, ($C_1$-$C_3$)-alkyl, ($C_1$-$C_3$)-haloalkyl, ($C_1$-$C_3$)-cyanoalkyl, ($C_1$-$C_3$)-hydroxyalkyl, hydroxycarbonyl-($C_1$-$C_3$)-alkoxy, ($C_1$-$C_3$)-alkoxycarbonyl-($C_1$-$C_3$)-alkyl, ($C_1$-$C_3$)-alkoxy-($C_1$-$C_3$)-alkyl, ($C_2$-$C_3$)-alkenyl, ($C_2$-$C_3$)-haloalkenyl, ($C_2$-$C_3$)-cyanoalkenyl, ($C_2$-$C_3$)-alkynyl, ($C_2$-$C_3$)-haloalkynyl, ($C_2$-$C_3$)-cyanoalkynyl, ($C_1$-$C_3$)-alkoxy, ($C_1$-$C_3$)-haloalkoxy, ($C_1$-$C_3$)-cyanoalkoxy, ($C_1$-$C_3$)-alkoxycarbonyl-($C_1$-$C_3$)-alkoxy, ($C_1$-$C_3$)-alkoxy-($C_1$-$C_3$)-alkoxy, ($C_1$-$C_3$)-alkylhydroxyimino, ($C_1$-$C_3$)-alkoxyimino, ($C_1$-$C_3$)-alkyl-($C_1$-$C_3$)-alkoxyimino, ($C_1$-$C_3$)-haloalkyl-($C_1$-$C_3$)-alkoxyimino, ($C_1$-$C_3$)-alkylthio, ($C_1$-$C_3$)-haloalkylthio, ($C_1$-$C_3$)-alkoxy-($C_1$-$C_3$)-alkylthio, ($C_1$-$C_3$)-alkylthio-($C_1$-$C_3$)-alkyl, ($C_1$-$C_3$)-alkylsulfinyl, ($C_1$-$C_3$)-haloalkylsulfinyl, ($C_1$-$C_3$)-alkoxy-($C_1$-$C_3$)-alkylsulfinyl, ($C_1$-$C_3$)-alkylsulfinyl-($C_1$-$C_3$)-alkyl, ($C_1$-$C_3$)-alkylsulfonyl, ($C_1$-$C_3$)-haloalkylsulfonyl, ($C_1$-$C_3$)-alkoxy-($C_1$-$C_3$)-alkylsulfonyl, ($C_1$-$C_3$)-alkylsulfonyl-($C_1$-$C_3$)-alkyl, ($C_1$-$C_3$)-alkylsulfonyloxy, ($C_1$-$C_3$)-alkylcarbonyl, ($C_1$-$C_3$)-haloalkylcarbonyl, ($C_1$-$C_3$)-alkylcarbonyloxy, ($C_1$-$C_3$)-alkoxycarbonyl, ($C_1$-$C_3$)-haloalkoxycarbonyl, aminocarbonyl, ($C_1$-$C_3$)-alkylaminocarbonyl, di-($C_1$-$C_3$)-alkylaminocarbonyl, ($C_2$-$C_3$)-alkenylaminocarbonyl, di-($C_2$-$C_3$)-alkenylaminocarbonyl, ($C_3$-$C_6$)-cycloalkylaminocarbonyl, ($C_1$-$C_3$)-alkylsulfonylamino, ($C_1$-$C_3$)-alkylamino, aminosulfonyl, ($C_1$-$C_3$)-alkylaminosulfonyl, di-($C_1$-$C_3$)-alkylaminosulfonyl, ($C_1$-$C_3$)-alkylsulfoximino, aminothiocarbonyl, ($C_1$-$C_3$)-alkylaminothiocarbonyl, di-($C_1$-$C_3$)-alkylaminothiocarbonyl,
n represents 0 or 1.
R$^2$ particularly preferably represents hydrogen, cyano, halogen, ($C_1$-$C_3$)-alkyl, ($C_1$-$C_3$)-haloalkyl, ($C_2$-$C_3$)-alkenyl, ($C_2$-$C_3$)-haloalkenyl, ($C_2$-$C_3$)-alkynyl, ($C_2$-$C_3$)-haloalkynyl, ($C_1$-$C_3$)-alkoxy, ($C_1$-$C_3$)-haloalkoxy, ($C_1$-$C_3$)-alkylsulfinyl, ($C_1$-$C_3$)-haloalkylsulfinyl, ($C_1$-$C_3$)-alkylsulfonyl, ($C_1$-$C_3$)-haloalkylsulfonyl or
represents phenyl or hetaryl from the group Q-1, Q-22, Q-36, Q-37, Q-41, Q-44, Q-45, Q-51, Q-64, Q-66, Q-67, each of which is optionally mono- or disubstituted by identical or different substituents,
possible substituents being in each case: cyano, halogen, ($C_1$-$C_3$)-alkyl, ($C_1$-$C_3$)-haloalkyl, ($C_2$-$C_3$)-alkenyl, ($C_2$-$C_3$)-haloalkenyl, ($C_1$-$C_3$)-alkoxy, ($C_1$-$C_3$)-haloalkoxy, ($C_1$-$C_3$)-alkylsulfinyl, ($C_1$-$C_3$)-haloalkylsulfinyl, ($C_1$-$C_3$)-alkylsulfonyl, ($C_1$-$C_3$)-haloalkylsulfonyl, ($C_1$-$C_3$)-alkylthio,
R$^3$, R$^4$, R$^5$ and R$^6$ independently of one another particularly preferably represent hydrogen, cyano, halogen, ($C_1$-$C_3$)-alkyl, ($C_1$-$C_3$)-haloalkyl, ($C_2$-$C_3$)-alkenyl, ($C_2$-$C_3$)-haloalkenyl, ($C_2$-$C_3$)-alkynyl, ($C_2$-$C_3$)-haloalkynyl, ($C_1$-$C_3$)-alkoxy, ($C_1$-$C_3$)-haloalkoxy, ($C_1$-$C_3$)-alkylsulfinyl, ($C_1$-$C_3$)-haloalkylsulfinyl, ($C_1$-$C_3$)-alkylsulfonyl, ($C_1$-$C_3$)-haloalkylsulfonyl,
with the proviso that R$^3$, R$^4$, R$^5$ and R$^6$ do not simultaneously represent hydrogen or
R$^3$ and R$^4$, or R$^4$ and R$^5$, or R$^5$ and R$^6$ together with the atoms to which they are attached particularly preferably form a saturated, optionally fluorine-, chlorine- or ($C_1$-$C_3$)-alkyl-substituted 5-membered ring which optionally contains one or two oxygen atoms (where the heteroatoms must not be directly adjacent to one another),
R$^{10}$ particularly preferably represents cyano, halogen, ($C_1$-$C_3$)-alkyl, ($C_1$-$C_3$)-haloalkyl, ($C_2$-$C_3$)-alkenyl, ($C_2$-$C_3$)-haloalkenyl, ($C_1$-$C_3$)-alkoxy, ($C_1$-$C_3$)-haloalkoxy, ($C_1$-$C_3$)-alkylsulfinyl, ($C_1$-$C_3$)-haloalkylsulfinyl, ($C_1$-$C_3$)-alkylsulfonyl, ($C_1$-$C_3$)-haloalkylsulfonyl, ($C_1$-$C_3$)-alkylthio,
n represents 0 or 1.
R$^2$ very particularly preferably represents hydrogen, fluorine, chlorine, bromine, methyl, ethyl, difluoromethyl, trifluoromethyl, represents in each case optionally chlorine-substituted phenyl or hetaryl from group Q-41,
R$^3$ very particularly preferably represents hydrogen,
R$^4$ very particularly preferably represents hydrogen, chlorine, fluorine, cyano, SO$_2$CH$_3$, SO$_2$C$_2$H$_5$, trifluoromethyl, difluoromethyl, difluoromethoxy, trifluoromethoxy or 2,2,2-trifluoroethoxy,
R$^5$ very particularly preferably represents hydrogen, chlorine, fluorine, cyano, SO$_2$CH$_3$, SO$_2$C$_2$H$_5$, trifluoromethyl, difluoromethyl, difluoromethoxy, trifluoromethoxy or 2,2,2-trifluoroethoxy,
R$^6$ very particularly preferably represents hydrogen,
with the proviso that R$^3$, R$^4$, R$^5$ and R$^6$ do not simultaneously represent hydrogen or
R$^3$ and R$^4$, or R$^4$ and R$^5$, or R$^5$ and R$^6$ very particularly preferably form
the following 5-membered ring

which is optionally mono- or disubstituted by fluorine,
R$^{10}$ very particularly preferably represents methyl, ethyl, chlorine, fluorine, cyano, difluoromethyl, trifluoromethyl, SCH$_3$, SOCH$_3$, SO$_2$CH$_3$, SC$_2$H$_5$, SOC$_2$H$_5$, SO$_2$C$_2$H$_5$, methoxy, ethoxy, difluoromethoxy, trifluoromethoxy or 2,2,2-trifluoroethoxy,
n represents 0 or 1.
R$^2$ most preferably represents hydrogen, chlorine, methyl, represents hetaryl from group Q-41 or represents phenyl which is optionally monosubstituted by chlorine,
R$^3$ most preferably represents hydrogen,
R$^4$ most preferably represents hydrogen, fluorine, chlorine, cyano or trifluoromethyl,
R$^5$ most preferably represents hydrogen, fluorine, chlorine, trifluoromethyl or SO$_2$CH$_3$,
or
R$^4$ and R$^5$ together most preferably represent —O—CF$_2$—O—,
R$^6$ most preferably represents hydrogen,
with the proviso that R$^3$, R$^4$, R$^5$ and R$^6$ do not simultaneously represent hydrogen,
R$^{10}$ most preferably represents methyl, ethyl, chlorine, fluorine, trifluoromethyl, SCH$_3$, SO$_2$CH$_3$, SC$_2$H$_5$, SOC$_2$H$_5$, SO$_2$C$_2$H$_5$, methoxy or ethoxy, (with particular emphasis methyl, ethyl, chlorine or methoxy), n represents 0 or 1.

The compounds of the formula (I) according to the invention can be obtained by the processes shown in the following schemes:

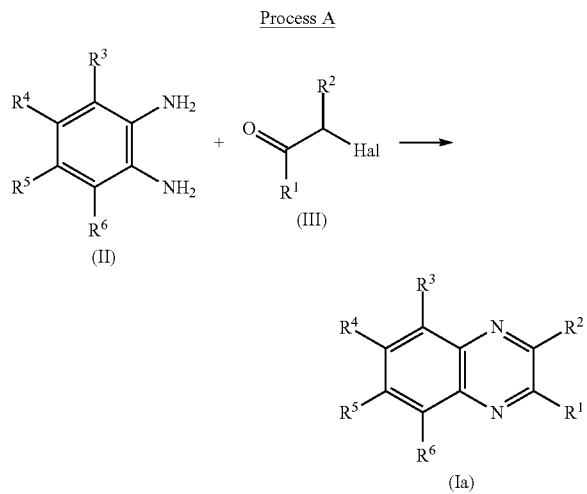

The radicals R$^1$, R$^2$, R$^3$, R$^4$, R$^5$ and R$^6$ have the meanings described above and Hal represents halogen.

The compounds of the formula (Ia) can be prepared analogously to the process described in the patent application DD 0151753 by reacting benzene-1,2-diamines of the formula (II) with 2-halo-1-(het)arylethanones of the formula (III). Further examples of this process are published in *J. Org. Chem.*, 1966, 31 (3), 803-806, *Pharmazie* 40 (1985), 384-387, *Bull. Soc. Chim. Fr.*, (1950) 753-757, *Helv. Chim. Acta*, 1952, 35, 2301-2314, *Tetrahedron*, 2008, 64, 8676-8684, *Tetrahedron Lett.*, 2007, 48, 5371, *Tetrahedron Lett.*, 2011, 52, 2862 or *J. of Chem. and Eng. Data*, 1973, 18(1), 102-104.

Alternatively, *J. Chin. Chem. Soc.* 2009, 56(4), 683-687 realizes a process which describes the use of α-sulfonyloxy-(het)arylketones in PEG-400 as solvent.

If asymmetric benzene-1,2-diamines of the formula (II) are used, a mixture of the regioisomeric quinoxalines of the formula (Ia) may be obtained. These can be separated using the customary chromatographic methods.

Benzene-1,2-diamines of the formula (II) are either commercially available or can be prepared by known methods, for example analogously to *J. Org. Chem.*, 1969, 384 or *J. Med. Chem.* 1981, 24(1), 93-101.

2-Halo-1-(het)arylethanones of the formula (III) are either commercially available or can be prepared by known methods, for example analogously to the processes described in *Helv. Chim. Acta*, 1955, 38, 1289-1291, *Pharmazie* 40 (1985), 384-387, WO 2009/114552 or DD 0151753.

The reaction of the benzene-1,2-diamines of the formula (II) with 2-halo-1-(het)arylethanones of the formula (III) can be carried out neat or in a solvent, preference being given to carrying out the reaction in a solvent selected from customary solvents that are inert under the prevailing reaction conditions.

Preference is given to aliphatic alcohols such as, for example, methanol, ethanol, n-propanol or isopropanol; ethers such as, for example, diisopropyl ether, dioxane, tetrahydrofuran, 1,2-dimethoxyethane; nitriles such as, for example, acetonitrile or propionitrile.

The reaction is preferably carried out in the presence of a base. Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given to sodium acetate, sodium phosphate, potassium phosphate, caesium carbonate, sodium carbonate, potassium carbonate, sodium hydrogencarbonate, potassium hydrogencarbonate.

The reaction can be carried out under reduced pressure, at atmospheric pressure or under elevated pressure and at temperatures of 0 to 180° C.; with preference, the reaction is carried out at atmospheric pressure and temperatures of 20 to 110° C.

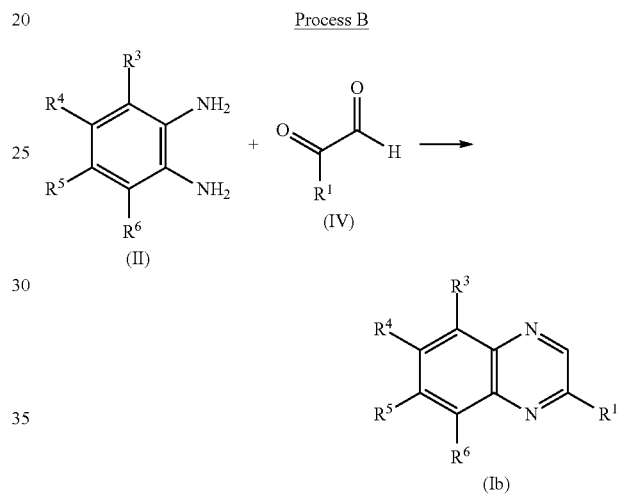

The radicals R$^1$, R$^3$, R$^4$, R$^5$ and R$^6$ have the meanings described above. In one embodiment according to the invention, benzene-1,2-diamines of the formula (II) are reacted with glyoxals of the formula (IV). This is a special case of the general synthesis of quinoxalines in which benzene-1,2-diamines of the formula (II) are reacted with β-dicarbonyl compounds. There is extensive literature about this subject, cited, for example, in *Synth. Commun.* 1995, 25(15), 2319-26, *Tetrahedron Lett.*, 2005, 46, 6345, *Tetrahedron Lett.*, 2005, 46, 7183, *J. Med. Chem.*, 2010, 53, 1128 or *Bull. Korean Chem. Soc.* 2012, 33(8), 2581.

Glyoxals of the formula (IV) are either commercially available or can be prepared by known methods, for example according to the processes described in *Bull. Soc. Chim. Fr.*, (1950) 753-757, *J. Med. Chem.* 1979, 22(6), 687-694, *J. of Chem. and Eng. Data*, 1973, 18(1), 102-104, *Current Chemistry Letters* 2012, 1(3), 139-146 or U.S. Pat. No. 6,649,768.

If asymmetric benzene-1,2-diamines of the formula (II) are used, a mixture of the regioisomeric quinoxalines of the formula (Ib) may be obtained. These can be separated using the customary chromatographic methods.

The process is carried out, for example, analogously to the processes described in *Current Chemistry Letters* 2012, 1(3), 139-146, *Bull. Korean Chem. Soc.* 2011, 32(10), 3720, *J. of Chem. and Eng. Data*, 1973, 18(1), 102-104 or *J. Chem. Research (S)*, 1986, 16-17.

The reaction of the benzene-1,2-diamines of the formula (II) with glyoxals of the formula (IV) can be carried out neat or in a solvent; with preference, the reaction is carried out in a solvent selected from customary solvents that are inert under the prevailing reaction conditions.

Preference is given to aliphatic alcohols such as, for example, methanol, ethanol, n-propanol or isopropanol; ethers such as, for example, diisopropyl ether, dioxane, tetrahydrofuran, 1,2-dimethoxyethane; nitriles such as, for example, acetonitrile or propionitrile; polar aprotic solvents such as N,N-dimethylformamide, dimethyl sulfoxide, N-methylpyrrolidone, and also to mixtures of these solvents.

The reaction can be carried out under reduced pressure, at atmospheric pressure or under elevated pressure and at temperatures of 0 to 180° C.; with preference, the reaction is carried out at atmospheric pressure and temperatures of 20 to 110° C.

G represents hydrogen, $(C_1-C_6)$-alkyl, $(C_2-C_6)$-alkenyl or aryl (preferably hydrogen, $(C_1-C_4)$-alkyl, $(C_2-C_4)$-alkenyl or phenyl; particularly preferably hydrogen) or $B(OG)_2$ together form a 5- or 6-membered cycle (preferably a 5-membered cycle, particularly preferably

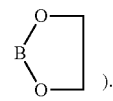
).

Step (a)

In one embodiment according to the invention, benzene-1,2-diamines of the formula (II) are reacted with alkylhy- Process C:

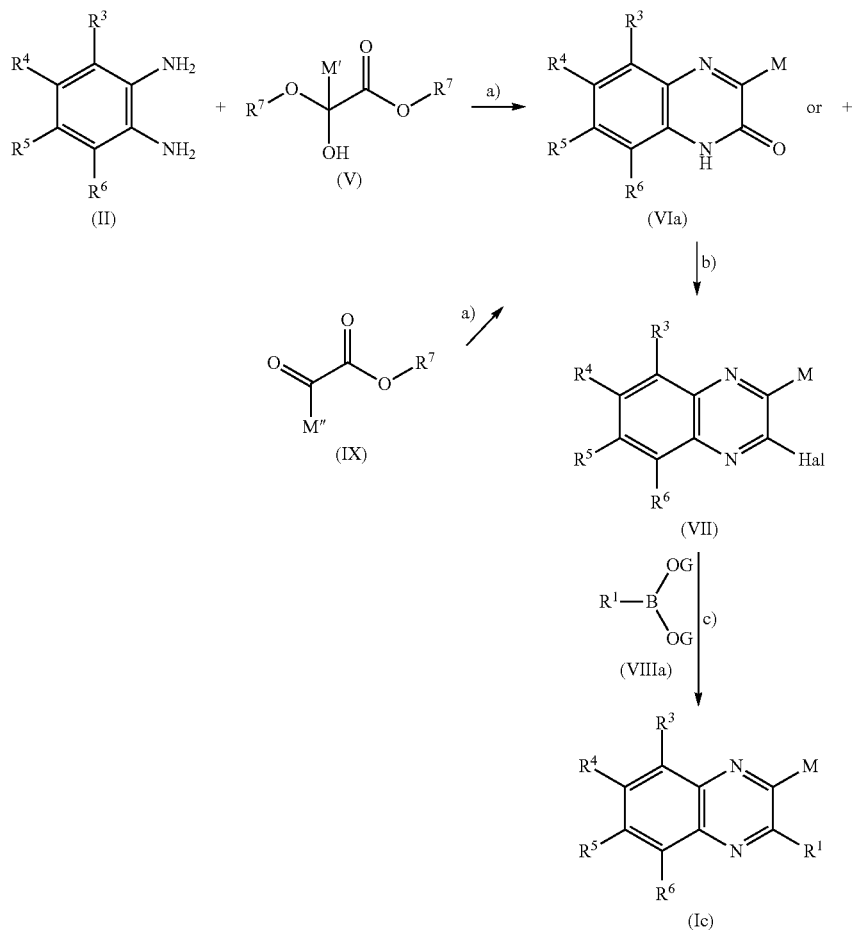

The radicals Hal, $R^1$, $R^3$, $R^4$, $R^5$ and $R^6$ have the meanings described above, $R^7$ represents hydrogen or $(C_1-C_6)$-alkyl (preferably hydrogen or $(C_1-C_4)$-alkyl; particularly preferably hydrogen or methyl), M' represents hydrogen or $(C_1-C_6)$-alkyl (preferably hydrogen or $(C_1-C_4)$-alkyl; particularly preferably hydrogen, methyl or trifluoromethyl), M" represents hydrogen, $(C_1-C_6)$-alkyl or $(C_3-C_8)$-cycloalkyl (preferably hydrogen, $(C_1-C_4)$-alkyl or $(C_3-C_6)$-cycloalkyl; particularly preferably hydrogen or methyl), M represents M' or M", droxy(alkoxy)acetates of the formula (V) to give the quinoxalin-2(1H)-ones of the formula (VIa).

This general synthesis process is cited, for example, in *Chem. Ber.* 87, 1062 (1954) or *Chem. Ber.* 90, 2604 (1957). The use of hydroxyketones instead of the glyoxylic ester semiacetals (V) is described in *Synth. Commun.* 2012, 42, 236-245.

Compounds of the formula (V) are commercially available.

Alternatively, benzene-1,2-diamines of the formula (II) are reacted with carbonyl compounds of the formula (IX) to give the quinoxalin-2(1H)-ones of the formula (VIa).

This general synthesis process is described, for example, in US 2005/0256000, WO 2011/022439, *Tetrahedron Lett.*, 2008, 49, *J. Med. Chem.* 1981, 24(1), 93-101, *J. Heterocycl. Chem.* 24, 1771, (1987), *J. Heterocyclic Chem.* 29, 129, (1992) or in *Helv. Chim. Acta* 2010, 93, 1216-1220.

Carbonyl compounds of the formula (IX) are commercially available.

If asymmetric benzene-1,2-diamines of the formula (II) are used, a mixture of the regioisomeric quinoxalin-2(1H)-ones of the formula (VIa) may be obtained. These can be separated using the customary chromatographic methods.

The reactions of the benzene-1,2-diamines of the formula (II) with alkylhydroxy(alkoxy)acetates of the formula (V) or with carbonyl compounds of the formula (IX) can be carried out neat or in a solvent; with preference, the reaction is carried out in a solvent selected from customary solvents that are inert under the prevailing reaction conditions.

Preference is given to aliphatic alcohols, for example methanol, ethanol or isopropanol; ethers, for example diisopropyl ether, dioxane, tetrahydrofuran, 1,2-dimethoxyethane; nitriles, for example acetonitrile or propionitrile; or amides, for example N,N-dimethylformamide (DMF), N,N-dimethylacetamide or N-methylpyrrolidone; or mixtures of these with water; and pure water or 1,2-dichloroethane.

The reaction can be carried out under reduced pressure, at atmospheric pressure or under elevated pressure and at temperatures of −20 to 180° C.; with preference, the reaction is carried out at atmospheric pressure and temperatures of 30 to 130° C.

Step (b)

According to the invention, the quinoxalin-2(1H)-ones of the formula (VIa) obtained in step (a) are reacted with a halogenating agent to give the quinoxalines of the formula (VII).

Suitable halogenating agents are, for example, $PCl_3$, $POCl_3$, $PCl_5$, $POBr_3$, $PBr_5$, thionyl chloride or N-halosuccinimides or mixtures of these reagents. Preferably, the halogenating agent used is $POCl_3$. These synthesis variants are described in WO 95/42463, WO 2008/141065, WO 2008/148867, WO 2011/022439, *Rec. Trav. Chim. Pays-Bas*, 1972, 91, 850-860, *J. Med. Chem.*, 1981, 24(1), 93-101, *J. Heterocyclic Chem.* 33, 447 (1996) and *Tetrahedron Lett.*, 1999, 40, 7477.

Alternatively, the halogenations were carried out according to step (b) with the aid of tetraalkylammonium iodides, tetraalkylammonium bromides and tetraalkylammonium chlorides in the presence of $P_2O_5$. This method is described in *Tetrahedron Lett.*, 2001, 42, 4849-4851.

Some of the compounds of the formula (VIa) are novel, some are commercially available.

The reaction of the compounds of the formula (VIa) with the halogenating agent can be carried out neat or in a solvent; with preference, the reaction is carried out in a solvent selected from customary solvents that are inert under the prevailing reaction conditions.

Preference is given to aromatic hydrocarbons such as, for example, benzene, toluene, xylene or decalin; halogenated hydrocarbons such as, for example, chlorobenzene, dichlorobenzene, dichloromethane or chloroform.

The reaction is preferably carried out in the presence of a base. Suitable bases are organic and inorganic bases which are typically used in such reactions. Preference is given to using bases selected by way of example from the group consisting of acetates, phosphates, carbonates and hydrogencarbonates of alkali metals or alkaline earth metals. Particular preference is given to sodium acetate, sodium phosphate, potassium phosphate, caesium carbonate, sodium carbonate, potassium carbonate, sodium hydrogencarbonate, potassium hydrogencarbonate. Moreover, preference is given to tertiary amines such as, for example, trimethylamine, triethylamine, tributylamine, triethylamine hydrochloride, N-ethyldiisopropylamine and pyridine.

The reaction can be carried out under reduced pressure, at atmospheric pressure or under elevated pressure and at temperatures of 0 to 180° C.; with preference, the reaction is carried out at atmospheric pressure and temperatures of 30 to 130° C.

Step c)

The quinoxalines of the formula (VII) obtained in step (b) are reacted with a boron compound of the formula (VIIIa). The reaction, preferably in the presence of a catalyst, optionally in the presence of a base in an organic solvent or in a mixture of a solvent with water, at ambient temperature or elevated temperatures leads to the quinoxalines of the formula (Ic) according to the invention.

Numerous examples of the coupling of halogenated quinoxalines with boron derivatives or organotin compounds (Stille coupling) are described in the literature. WO 2008/148867 publishes analogous couplings with (morpholine) arylboronic acids or corresponding aryl-1,3,2-dioxaborolanes in the presence of palladium catalysts. Further examples can be found in WO 2008/141065, WO 2009/073497, WO 2011/028947, WO 2012/045196, WO 2012/119046, *J. Org. Chem.* 1995, 60, 7508-7510, *J. Med. Chem.* 2005, 48(21), 6632-6642 or in *J. Am. Chem. Soc.* 2007, 129(11), 3358-3366.

*Organic Lett.* 2011, 16, 4374-4377 describes quinoxaline tosylates as coupling partners of boronic acids with Pd catalysis.

The use of stable MIDA-boronates for coupling with haloquinoxalines is described in Angew. Chem. Int. Ed., 2012, 51, 2667-2672.

Some of the compounds of the formula (VII) are novel, some are commercially available.

Boron derivatives of the formula (VIIIa) are either commercially available or they can be prepared by known methods cited, for example, in *J. Org. Chem.*, 1995, 60, 7508-7510, WO 2011/143495, WO2011/022439 or WO 2004/01913.

The catalysts used in the reactions of the haloquinoxalines preferably consist of salts or complexes of palladium, copper or nickel.

Suitable palladium catalysts are, for example, palladium (II) acetate, tetrakis(triphenylphosphine)palladium, bis(triphenylphosphine)palladium(II) chloride, tris(dibenzylideneacetone)dipalladium(0) in the presence of ligands, for example 2,2'-bis(diphenylphosphino)-1,1'-binaphthyl, 9,9-dimethyl-4,5-bis(diphenylphosphino)xanthene or 1,1'-bis(diphenylphosphino)ferrocene.

Suitable copper salts are, for example, copper(I) iodide, copper(I) chloride, copper(I) oxide, copper(I) triflate, copper (II) acetate, copper(II) triflate, frequently in the presence of a ligand, for example diamine ligands such as N,N'-dimethylethylenediamine, N,N-dimethylethylenediamine or trans-N,N'-dimethyl-1,2-cyclohexanediamine.

Suitable nickel catalysts are, for example, nickel(II) acetylacetonate alone or in combination with the phosphor ligands mentioned above or nickel(II) acetylacetonate with imidazolium carbene ligands.

The catalyst is usually employed in a substoichiometric amount, preferably of 0.001-0.8 equivalents and particularly preferably of 0.01 to 0.5 equivalents, based on the quinoxalines of the formula (VII) employed.

The reaction of the quinoxalines of the formula (VII) with a boronic acid is preferably carried out in a solvent selected from customary solvents which are inert under the prevailing reaction conditions. Preference is given to ethers such as, for example, dioxane, tetrahydrofuran, diethyl ether or 1,2-dimethoxyethane; aromatic hydrocarbons such as, for example, benzene, toluene or xylene; aliphatic alcohols such as, for example, methanol, ethanol or isopropanol; nitriles such as, for example, acetonitrile or propionitrile; polar aprotic solvents such as N,N-dimethylformamide, dimethyl sulfoxide, N-methylpyrrolidone and also mixtures of these solvents with water.

The reaction is preferably carried out in the presence of a base. Suitable bases are inorganic bases, in particular acetates, phosphates, carbonates and hydrogencarbonates of alkali metals or alkaline earth metals. Particular preference is given to sodium acetate, sodium phosphate, potassium phosphate, caesium carbonate, sodium carbonate, potassium carbonate, sodium hydrogencarbonate, potassium hydrogencarbonate. The inorganic bases can also be employed as aqueous solutions.

The reaction can be carried out under reduced pressure, at atmospheric pressure or under elevated pressure and at temperatures of 0 to 200° C., preference being given to effecting the reaction at atmospheric pressure and temperatures of 40 to 150° C., optionally under inert gas atmosphere.

Instead of the boronic acid, it is also possible to use other boron compounds, for instance potassium trifluoroborates, boronic esters, or else other organometallic compounds, for instance stannanes, silanes or bismuthanes.

Suitable organotin compounds are corresponding trimethylstannyl or tributylstannyl compounds such as, for example, those described in WO 20111/22815 or WO 2011/022439.

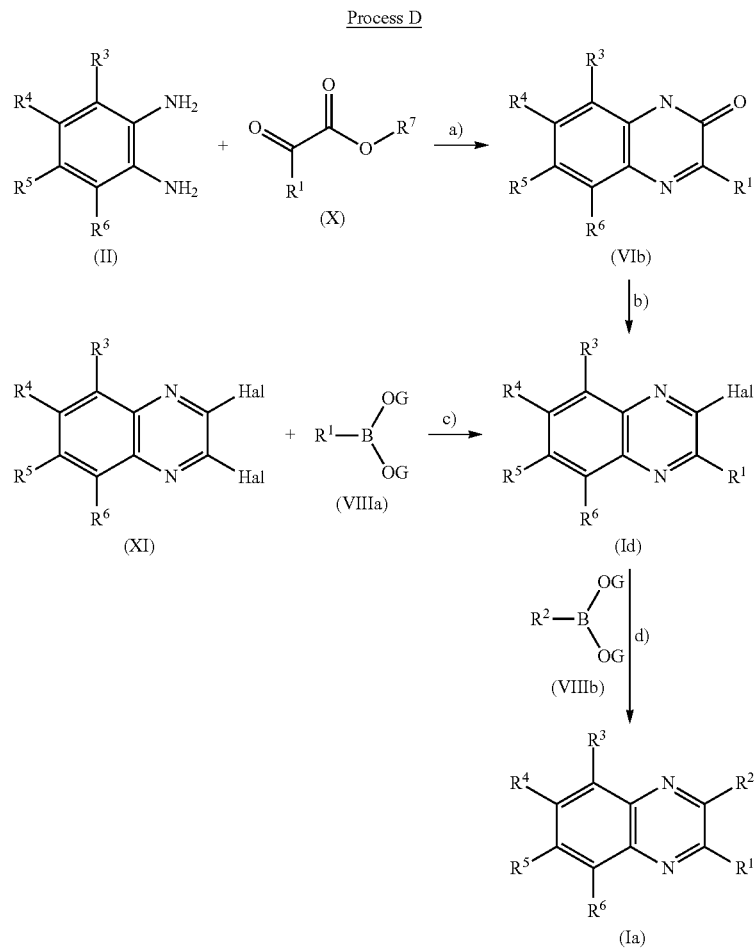

Process D

The radicals $R^1$, $R^2$, $R^3$, $R^4$, $R^5$, $R^6$, $R^7$, Hal, G and $B(OG)_2$ have the meanings described above.

Step a)

In one embodiment according to the invention, benzene-1,2-diamines of the formula (II) are reacted with carbonyl compounds of the formula (X) to give the quinoxalin-2(1H)-ones of the formula (VIb).

The reaction is carried out analogously to the methods used in process C, step a), or as described in *J. Heterocyclic Chem.* 29, 129, (1976), *J. Heterocyclic Chem.* 33, 447, (1996), *Helv. Chim. Acta*, 93, 1216-1220 (2010), *J. Chem. Research (S)*, 1986, 16-17 or US 2005/0256000.

If asymmetric benzene-1,2-diamines (II) are used, a mixture of the regioisomeric quinoxalin-2(1H)-ones of the formula (VIb) may be obtained. These can be separated using the customary chromatographic methods.

Carbonyl compounds of the formula (X) are commercially available or can be prepared by known methods, for example analogously to *Synth. Commun.* 2008, 38 (24), 4434-444, *J. Org. Chem.* 1981, 211, *Tetrahedron Lett.*, 2002, 43, 5361-5365, DE 2824407, JP 52027745 or EP-A-512352.

Step b)

According to the invention, the quinoxalin-2(1H)-ones of the formula (VIb) obtained in step (a) are reacted with a halogenating agent analogously to process C, step b), to give the quinoxalines of the formula (Id).

Some of the compounds of the formula (VIb) are novel, some are commercially available.

Step c)

Alternatively, in a further embodiment according to the invention, quinoxalines of the formula (Id) are obtained from quinoxalines of the formula (XI) and a boron compound of the formula (VIIIa), analogously to the way the reaction is carried out as described in process A, step c).

The 1,2-bishaloquinoxalines of the formula (XI) are prepared analogously to processes from U.S. Pat. No. 5,514,680, *J. Med. Chem.* 1981, 24(1), 93-101 or *J. Heterocycl. Chem.* 2009, 46, 317-319 by reacting 1,4-dihydroquinoxaline-2,3-diones with suitable halogenating agents, for example $POCl_3$ or thionyl chloride.

Some of the compounds of the formula (XI) are novel, some are commercially available.

Step d)

The quinoxalines of the formula (Id) according to the invention obtained in step (b) or step (c) are converted in an embodiment analogous to that described in process A, step c) by reaction with a boron compound of the formula (VIIIb) into the quinoxalines of the formula (Ia).

Boron derivatives of the formula (VIIIb) are either commercially available or can be prepared by known methods, for example as cited in *J. Org. Chem.*, 1995, 60, 7508-7510, WO 2011/143495 or WO 2004/01913.

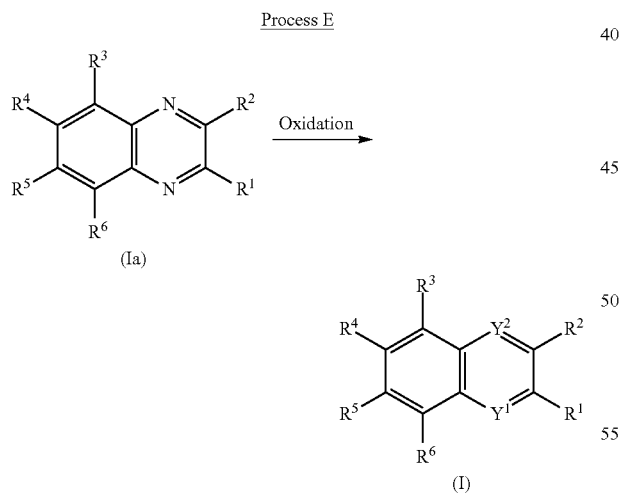

The radicals $Y^1$, $Y^2$, $R^1$, $R^2$, $R^3$, $R^4$, $R^5$ and $R^6$ have the meanings described above.

The quinoxalines of the formula (Ia) obtained in processes A to D can be converted by reaction with oxidizing agents into the corresponding N-oxides of the general structure (I). The reaction is carried out analogously to *J. Chem. Soc.* 479 (1938), *J. of Chem. and Eng. Data*, 1973, 18(1), 102-104, *Synlett* 2001, (1), 73-73, WO 2008/015423, *J. Org. Chem.* 1977, 1869-1871, *Chem. Pharm. Bull.* 1974, 22, 2097-2100 or *J. Chem. Research* (S), 1986, 16-17.

The oxidizing agents used are meta-chloroperbenzoic acid, rhenium salts, e.g. $MeReO_3$ in the presence of $H_2O_2$ and methanol as solvent, $K_2S_2O_8$ in sulfuric acid or 30-70% strength aqueous solutions of hydrogen peroxide, optionally in the presence of molecular sieves or a catalyst, for example $Na_2WO_4$ dihydrate, and optionally in the presence of organic acids, for example in formic acid or acetic acid.

Suitable solvents are dichloromethane, trichloromethane, methanol, formic acid, acetic acid or trifluoroacetic acid.

The oxidizing agent used is preferably a 35% strength aqueous solution of hydrogen peroxide in acetic acid.

The reaction can be carried out at atmospheric pressure or under elevated pressure and at temperatures from 0° C. to 60° C.; preferably, the reaction is carried out at atmospheric pressure and temperatures of from 40 to 50° C.

The compounds of the formulae (Ia), (Ib), (Ic) and (Id) are substructures of the compounds of the formula (I):

Taking into account the meaning $Y^1=Y^2=N$, the following structure is obtained:

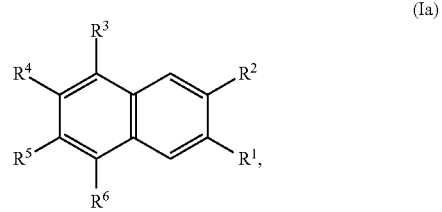

taking into account the meaning $Y^1=Y^2=N$ and $R^2$=hydrogen, the following structure is obtained:

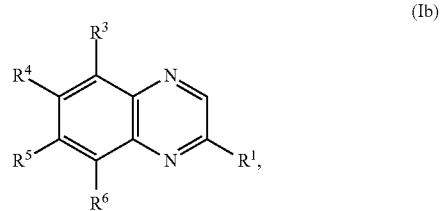

taking into account the meaning $Y^1=Y^2=N$ and $R^2=M$, the following structure is obtained:

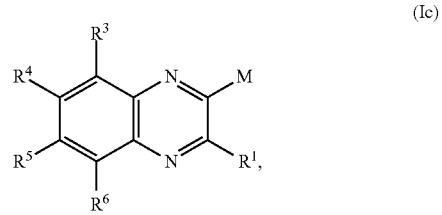

taking into account the meaning $Y^1=Y^2=N$ and $R^2$=Hal, the following structure is obtained:

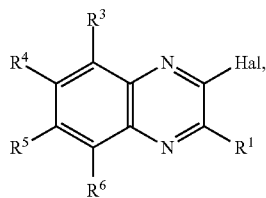

(Id)

in which M, Hal, $R^1$, $R^2$, $R^3$, $R^4$, $R^5$ and $R^6$ have the meanings given above.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always comprises the term "crop protection agent".

The compounds of the formula (I), given good plant tolerance, favorable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are active against normally sensitive and resistant species and also against all or some stages of development. The abovementioned pests include:

pests from the phylum of the Arthropoda, especially from the class of the Arachnida, for example *Acarus* spp., for example *Acarus siro*, *Aceria kuko*, *Aceria sheldoni*, *Aculops* spp., *Aculus* spp., for example *Aculus fockeui*, *Aculus schlechtendali*, *Amblyomma* spp., *Amphitetranychus viennensis*, *Argas* spp., *Boophilus* spp., *Brevipalpus* spp., for example *Brevipalpus phoenicis*, *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., for example *Eotetranychus hicoriae*, *Epitrimerus pyri*, *Eutetranychus* spp., for example *Eutetranychus banksi*, *Eriophyes* spp., for example *Eriophyes pyri*, *Glycyphagus domesticus*, *Halotydeus destructor*, *Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis*, *Nuphersa* spp., *Oligonychus* spp., for example *Oligonychus coniferarum*, *Oligonychus ilicis*, *Oligonychus indicus*, *Oligonychus mangiferus*, *Oligonychus pratensis*, *Oligonychus punicae*, *Oligonychus yothersi*, *Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora*, *Platytetranychus multidigituli*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., for example *Tarsonemus confusus*, *Tarsonemus pallidus*, *Tetranychus* spp., for example *Tetranychus canadensis*, *Tetranychus cinnabarinus*, *Tetranychus turkestani*, *Tetranychus urticae*, *Trombicula alfreddugesi*, *Vaejovis* spp., *Vasates lycopersici*;

from the class of the Chilopoda, for example *Geophilus* spp., *Scutigera* spp.;

from the order or the class of the Collembola, for example *Onychiurus armatus*; *Sminthurus viridis*;

from the class of the Diplopoda, for example *Blaniulus guttulatus*;

from the class of the Insecta, for example from the order of the Blattodea, for example *Blatta orientalis*, *Blattella asahinai*, *Blattella germanica*, *Leucophaea maderae*, *Panchlora* spp., *Parcoblatta* spp., *Periplaneta* spp., for example *Periplaneta americana*, *Periplaneta australasiae*, *Supella longipalpa*; from the order of the Coleoptera, for example *Acalymma vittatum*, *Acanthoscelides obtectus*, *Adoretus* spp., *Agelastica alni*, *Agriotes* spp., for example *Agriotes linneatus*, *Agriotes mancus*, *Alphitobius diaperinus*, *Amphimallon solstitialis*, *Anobium punctatum*, *Anoplophora* spp., *Anthonomus* spp., for example *Anthonomus grandis*, *Anthrenus* spp., *Apion* spp., *Apogonia* spp., *Atomaria* spp., for example *Atomaria linearis*, *Attagenus* spp., *Baris caerulescens*, *Bruchidius obtectus*, *Bruchus* spp., for example *Bruchus pisorum*, *Bruchus rufimanus*, *Cassida* spp., *Cerotoma trifurcata*, *Ceutorrhynchus* spp., for example *Ceutorrhynchus assimilis*, *Ceutorrhynchus quadridens*, *Ceutorrhynchus rapae*, *Chaetocnema* spp., for example *Chaetocnema confinis*, *Chaetocnema denticulata*, *Chaetocnema ectypa*, *Cleonus mendicus*, *Conoderus* spp., *Cosmopolites* spp., for example *Cosmopolites sordidus*, *Costelytra zealandica*, *Ctenicera* spp., *Curculio* spp., for example *Curculio caryae*, *Curculio caryatrypes*, *Curculio obtusus*, *Curculio sayi*, *Cryptolestes ferrugineus*, *Cryptolestes pusillus*, *Cryptorhynchus lapathi*, *Cryptorhynchus mangiferae*, *Cylindrocopturus* spp., *Cylindrocopturus adspersus*, *Cylindrocopturus furnissi*, *Dermestes* spp., *Diabrotica* spp., for example *Diabrotica balteata*, *Diabrotica barberi*, *Diabrotica undecimpunctata howardi*, *Diabrotica undecimpunctata undecimpunctata*, *Diabrotica virgifera virgifera*, *Diabrotica virgifera zeae*, *Dichocrocis* spp., *Dicladispa armigera*, *Diloboderus* spp., *Epilachna* spp., for example *Epilachna borealis*, *Epilachna varivestis*, *Epitrix* spp., for example *Epitrix cucumeris*, *Epitrix fuscula*, *Epitrix hirtipennis*, *Epitrix subcrinita*, *Epitrix tuberis*, *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., for example *Hypothenemus hampei*, *Hypothenemus obscurus*, *Hypothenemus pubescens*, *Lachnosterna consanguinea*, *Lasioderma serricorne*, *Latheticus oryzae*, *Lathridius* spp., *Lema* spp., *Leptinotarsa decemlineata*, *Leucoptera* spp., for example *Leucoptera coffeella*, *Lissorhoptrus oryzophilus*, *Lixus* spp., *Luperomorpha xanthodera*, *Luperodes* spp., *Lyctus* spp., *Megascelis* spp., *Melanotus* spp., for example *Melanotus longulus oregonensis*, *Meligethes aeneus*, *Melolontha* spp., for example *Melolontha melolontha*, *Migdolus* spp., *Monochamus* spp., *Naupactus xanthographus*, *Necrobia* spp.,

*Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicomis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterbomiella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex;* from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inomata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis vibumiphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Cameocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Nephotettix* spp., for example *Nephotettix cincticeps, Nephotettix nigropictus, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus vibumi, Psyllopsis* spp., *Psylla* spp., for example *Psylla buxi, Psylla mali, Psylla pyri, Pteromalus* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example

*Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Monalonion atratum, Nezara* spp., for example *Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Diprion* spp., for example *Diprion similis, Hoplocampa* spp., for example *Hoplocampa cookei, Hoplocampa testudinea, Lasius* spp., *Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Microtermes obesi, Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella,*

*Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella (=Plutella maculipennis), Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Heliothrips* spp., *Hercinothrips*

*femoralis, Rhipiphorothrips cruentatus, Scirtothrips* spp., *Taeniothrips cardamomi, Thrips* spp., for example *Thrips palmi, Thrips tabaci;*
from the order of the Zygentoma (=*Thysanura*), for example *Ctenolepisma* spp., *Lepisma saccharina, Lepismodes inquilinus, Thermobia domestica;*
from the class of the Symphyla, for example *Scutigerella* spp., for example *Scutigerella immaculata;*
pests from the phylum of the Mollusca, in particular from the class of the Bivalvia, for example *Dreissena* spp.;
and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;
animal and human parasites from the phyla of the Platyhelminthes and Nematoda, for example *Aelurostrongylus* spp., *Amidostomum* spp., *Ancylostoma* spp., *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp., *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;
plant pests from the phylum of the Nematoda, i.e. phytoparasitic nematodes, especially *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paraphelenchus* spp., *Paratrichodorus* spp., for example *Paratrichodorus minor, Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., *for example Tylenchorhynchus annulatus, Tylenchulus* spp., for example *Tylenchulus semipenetrans, Xiphinema* spp., for example *Xiphinema index.*

In addition, it is possible to control, from the sub-kingdom of the Protozoa, the order of the Coccidia, for example *Eimeria* spp.

Nematodes

In the present context, the term "nematodes" comprises all species of the phylum Nematoda and here in particular species acting as parasites on plants or fungi (for example species of the order Aphelenchida, Meloidogyne, Tylenchida and others) or else on humans and animals (for example species of the orders Trichinellida, Tylenchida, Rhabditina and Spirurida) or causing damage in or on these living organisms, and also other parasitic helminths.

A nematicide in crop protection, as described herein, is capable of controlling nematodes.

The term "controlling nematodes" means killing the nematodes or preventing or impeding their development or their growth or preventing or impeding their penetration into or their sucking on plant tissue.

Here, the efficacy of the compounds is determined by comparing mortalities, gall formation, cyst formation, nematode density per volume of soil, nematode density per root, number of nematode eggs per volume of soil, mobility of the nematodes between a plant or plant part treated with the compound of the formula (I) or the treated soil and an untreated plant or plant part or the untreated soil (100%). Preferably, the reduction achieved is 25-50% in comparison to an untreated plant, plant part or the untreated soil, more preferably 51-79% and most preferably the complete kill or the complete prevention of development and growth of the nematodes by a reduction of 80 to 100% is achieved. The control of nematodes as described herein also comprises the control of proliferation of the nematodes (development of cysts and/or eggs). Compounds of the formula (I) can also be used to keep the plants or animals healthy, and they can be employed curatively, preventatively or systemically for the control of nematodes.

The person skilled in the art knows methods for determining mortalities, gall formation, cyst formation, nematode density per volume of soil, nematode density per root, number of nematode eggs per volume of soil, mobility of the nematodes.

The use of a compound of the formula (I) may keep the plant healthy and also comprises a reduction of the damage caused by nematodes and an increase of the harvest yield.

In the present context, the term "nematodes" refers to plant nematodes which comprise all nematodes which damage plants. Plant nematodes comprise phytoparasitic nematodes and soil-borne nematodes. The phytoparasitic nematodes include ectoparasites such as *Xiphinema* spp., *Longidorus* spp. and *Trichodorus* spp.; semiparasites such as *Tylenchulus* spp.; migratory endoparasites such as *Pratylenchus* spp., *Radopholus* spp. and *Scutellonema* spp.; non-migratory parasites such as *Heterodera* spp., *Globodera* spp. and *Meloidogyne* spp., and also stem and leaf endoparasites such as *Ditylenchus* spp., *Aphelenchoides* spp. and *Hirschmaniella* spp. Particularly damaging root-parasitic soil nematodes are, for example, cyst-forming nematodes of the genera *Heterodera* or *Globodera*, and/or root gall nematodes of the genus *Meloidogyne*. Damaging species of these genera are, for example, *Meloidogyne incognita*, *Heterodera glycines* (soybean cyst nematode), *Globodera pallida* and *Globodera rostochiensis* (yellow potato cyst nematode), these species being controlled effectively by the compounds described in the present text. However, the use of the compounds described in the present text is by no means restricted to these genera or species, but also extends in the same manner to other nematodes.

The plant nematodes include, for example, *Aglenchus agricola*, *Anguina tritici*, *Aphelenchoides arachidis*, *Aphelenchoides fragaria*, and the stem and leaf endoparasites *Aphelenchoides* spp., *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus* and *Bursaphelenchus* spp., *Cacopaurus pestis*, *Criconemella curvata*, *Criconemella onoensis*, *Criconemella ornata*, *Criconemella rusium*, *Criconemella xenoplax* (=*Mesocriconema xenoplax*) and *Criconemella* spp., *Criconemoides femiae*, *Criconemoides onoense*, *Criconemoides ornatum* and *Criconemoides* spp., *Ditylenchus destructor*, *Ditylenchus dipsaci*, *Ditylenchus myceliophagus* and also the stem and leaf endoparasites *Ditylenchus* spp., *Dolichodorus heterocephalus*, *Globodera pallida* (=*Heterodera pallida*), *Globodera rostochiensis* (yellow potato cyst nematode), *Globodera solanacearum*, *Globodera tabacum*, *Globodera virginia* and the non-migratory cyst-forming parasites *Globodera* spp., *Helicotylenchus digonicus*, *Helicotylenchus dihystera*, *Helicotylenchus erythrine*, *Helicotylenchus multicinctus*, *Helicotylenchus nannus*, *Helicotylenchus pseudorobustus* und *Helicotylenchus* spp., *Hemicriconemoides*, *Hemicycliophora arenaria*, *Hemicycliophora nudata*, *Hemicycliophora parvana*, *Heterodera avenae*, *Heterodera cruciferae*, *Heterodera glycines* (soya bean cyst nematode), *Heterodera oryzae*, *Heterodera schachtii*, *Heterodera zeae* and the non-migratory cyst-forming parasites *Heterodera* spp., *Hirschmaniella gracilis*, *Hirschmaniella oryzae*, *Hirschmaniella spinicaudata* and the stem and leaf endoparasites *Hirschmaniella* spp., *Hoplolaimus aegyptii*, *Hoplolaimus californicus*, *Hoplolaimus columbus*, *Hoplolaimus galeatus*, *Hoplolaimus indicus*, *Hoplolaimus magnistylus*, *Hoplolaimus pararobustus*, *Longidorus africanus*, *Longidorus breviannulatus*, *Longidorus elongatus*, *Longidorus laevicapitatus*, *Longidorus vineacola* and the ectoparasites *Longidorus* spp., *Meloidogyne acronea*, *Meloidogyne africana*, *Meloidogyne arenaria*, *Meloidogyne arenaria thamesi*, *Meloidogyne artiella*, *Meloidogyne chitwoodi*, *Meloidogyne coffeicola*, *Meloidogyne ethiopica*, *Meloidogyne exigua*, *Meloidogyne fallax*, *Meloidogyne graminicola*, *Meloidogyne graminis*, *Meloidogyne hapla*, *Meloidogyne incognita*, *Meloidogyne incognita acrita*, *Meloidogyne javanica*, *Meloidogyne kikuyensis*, *Meloidogyne minor*, *Meloidogyne naasi*, *Meloidogyne paranaensis*, *Meloidogyne thamesi* and the non-migratory parasites *Meloidogyne* spp., *Meloinema* spp., *Nacobbus aberrans*, *Neotylenchus vigissi*, *Paraphelenchus pseudoparietinus*, *Paratrichodorus allius*, *Paratrichodorus lobatus*, *Paratrichodorus minor*, *Paratrichodorus nanus*, *Paratrichodorus porosus*, *Paratrichodorus teres* und *Paratrichodorus* spp., *Paratylenchus hamatus*, *Paratylenchus minutus*, *Paratylenchus projectus* und *Paratylenchus* spp., *Pratylenchus agilis*, *Pratylenchus alleni*, *Pratylenchus andinus*, *Pratylenchus brachyurus*, *Pratylenchus cerealis*, *Pratylenchus coffeae*, *Pratylenchus crenatus*, *Pratylenchus delattrei*, *Pratylenchus giibbicaudatus*, *Pratylenchus goodeyi*, *Pratylenchus hamatus*, *Pratylenchus hexincisus*, *Pratylenchus loosi*, *Pratylenchus neglectus*, *Pratylenchus penetrans*, *Pratylenchus pratensis*, *Pratylenchus scribneri*, *Pratylenchus teres*, *Pratylenchus thomei*, *Pratylenchus vulnus*, *Pratylenchus zeae* and the migratory endoparasites *Pratylenchus* spp., *Pseudohalenchus minutus*, *Psilenchus magnidens*, *Psilenchus tumidus*, *Punctodera chalcoensis*, *Quinisulcius acutus*, *Radopholus citrophilus*, *Radopholus similis*, the migratory endoparasites *Radopholus* spp., *Rotylenchulus borealis*, *Rotylenchulus parvus*, *Rotylenchulus reniformis* and *Rotylenchulus* spp., *Rotylenchus laurentinus*, *Rotylenchus macrodoratus*, *Rotylenchus robustus*, *Rotylenchus uniformis* and *Rotylenchus* spp., *Scutellonema brachyurum*, *Scutellonema bradys*, *Scutellonema clathricaudatum* and the migratory endoparasites *Scutellonema* spp., *Subanguina radiciola*, *Tetylenchus nicotianae*, *Trichodorus cylindricus*, *Trichodorus minor*, *Trichodorus primitivus*, *Trichodorus proximus*, *Trichodorus similis*, *Trichodorus sparsus* and the ectoparasites *Trichodorus* spp., *Tylenchorhynchus agri*, *Tylenchorhynchus brassicae*, *Tylenchorhynchus clarus*, *Tylenchorhynchus claytoni*, *Tylenchorhynchus digitatus*, *Tylenchorhynchus ebriensis*, *Tylenchorhynchus maximus*, *Tylenchorhynchus nudus*, *Tylenchorhynchus vulgaris* and *Tylenchorhynchus* spp., *Tylenchulus semipenetrans* and the semiparasites *Tylenchulus* spp., *Xiphinema americanum*, *Xiphinema brevicolle*, *Xiphinema dimorphicaudatum*, *Xiphinema index* and the ectoparasites *Xiphinema* spp.

Nematodes for the control of which a compound of the formula (I) may be used include nematodes of the genus *Meloidogyne* such as the Southern root-knot nematode (*Meloidogyne incognita*), the Javanese root-knot nematode (*Meloidogyne javanica*), the Northern root-knot nematode (*Meloidogyne hapla*) and the peanut root-knot nematode (*Meloidogyne arenaria*); nematodes of the genus *Ditylenchus* such as the potato rot nematode (*Ditylenchus destructor*) and stem and bulb eelworm (*Ditylenchus dipsaci*); nematodes of the genus *Pratylenchus* such as the cob root-lesion nematode (*Pratylenchus penetrans*), the chrysanthemum root-lesion nematode (*Pratylenchus fallax*), the coffee root nematode (*Pratylenchus coffeae*), the tea root nematode (*Pratylenchus loosi*) and the walnut root-lesion nematode (*Pratylenchus vulnus*); nematodes of the genus *Globodera* such as the yellow potato cyst nematode (*Globodera rostochiensis*) and the white potato cyst nematode (*Globodera pallida*); nematodes of the genus *Heterodera* such as the soybean cyst nematode (*Heterodera glycines*) and the beet cyst eelworm (*Heterodera schachtii*); nematodes of the genus *Aphelenchoides* such as the rice white-tip nematode (*Aphelenchoides besseyi*), the chrysanthemum nematode (*Aphelenchoides ritzemabosi*) and the strawberry nematode (*Aphelenchoides fragariae*); nematodes of the genus *Aphelenchus* such as the fungivorous nematode (*Aphelenchus avenae*); nematodes of the genus *Radopholus*, such as the burrowing nematode (*Radopholus similis*); nematodes of the genus *Tylenchulus* such as the citrus root nematode (*Tylenchulus semipenetrans*); nematodes of the genus *Rotylenchulus* such as the reniform nematode (*Rotylenchulus reniformis*); tree-dwelling nematodes such as the pine wood nematode (*Bursaphelenchus xylophilus*) and the red ring nematode (*Bursaphelenchus cocophilus*) and the like.

Plants for the protection of which a compound of the formula (I) can be used include plants such as cereals (for example rice, barley, wheat, rye, oats, maize and the like), beans (soybean, azuki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, pepper and the like), root crops (carrot, potato, sweet potato, radish, lotus root, turnip and the like), plants for industrial raw materials (cotton, hemp, paper mulberry, mitsumata, rape, beet, hops, sugar cane, sugar beet, olive, rubber, palm trees, coffee, tobacco, tea and the like), cucurbits (pumpkin, cucumber, watermelon, melon and the like), meadow plants (cocksfoot, sorghum, timothy-grass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compounds of the formula (I) are particularly suitable for controlling coffee nematodes, in particular *Pratylenchus brachyurus, Pratylenchus coffeae, Meloidogyne exigua, Meloidogyne incognita, Meloidogyne coffeicola, Helicotylenchus* spp. and also *Meloidogyne paranaensis, Rotylenchus* spp., *Xiphinema* spp., *Tylenchorhynchus* spp. and *Scutellonema* spp.

The compounds of the formula (I) are particularly suitable for controlling potato nematodes, in particular *Pratylenchus brachyurus, Pratylenchus pratensis, Pratylenchus scribneri, Pratylenchus penetrans, Pratylenchus coffeae, Ditylenchus dipsaci* and also *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne fallax, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae* and *Meloinema* spp.

The compounds of the formula (I) are particularly suitable for controlling tomato nematodes, in particular *Meloidogyne arenaria, Meloidogyne hapla, Meloidogyne javanica, Meloidogyne incognita, Pratylenchus penetrans* and also *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus* and *Rotylenchulus reniformis*.

The compounds of the formula (I) are particularly suitable for controlling cucumber plant nematodes, in particular *Meloidogyne arenaria, Meloidogyne hapla, Meloidogyne javanica, Meloidogyne incognita, Rotylenchulus reniformis* and *Pratylenchus thornei*.

The compounds of the formula (I) are particularly suitable for controlling cotton nematodes, in particular *Belonolaimus longicaudatus, Meloidogyne incognita, Hoplolaimus columbus, Hoplolaimus galeatus* and *Rotylenchulus reniformis*.

The compounds of the formula (I) are particularly suitable for controlling maize nematodes, in particular *Belonolaimus longicaudatus, Paratrichodorus minor* and also *Pratylenchus brachyurus, Pratylenchus delattrei, Pratylenchus hexincisus, Pratylenchus penetrans, Pratylenchus zeae, (Belonolaimus gracilis), Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum* and *Subanguina radiciola*.

The compounds of the formula (I) are particularly suitable for controlling soybean nematodes, in particular *Pratylenchus brachyurus, Pratylenchus pratensis, Pratylenchus penetrans, Pratylenchus scribneri, Belonolaimus longicaudatus, Heterodera glycines, Hoplolaimus columbus* and also *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus* and *Rotylenchulus reniformis*.

The compounds of the formula (I) are particularly suitable for controlling tobacco nematodes, in particular *Meloidogyne incognita, Meloidogyne javanica* and also *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp. and *Tetylenchus nicotianae*.

The compounds of the formula (I) are particularly suitable for controlling citrus nematodes, in particular *Pratylenchus coffeae* and also *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella* spp., *Hemicriconemoides, Radopholus similis* and *Radopholus citrophilus, Hemicycliophora arenaria, Hemicycliophora nudata* and *Tylenchulus semipenetrans*.

The compounds of the formula (I) are particularly suitable for controlling banana nematodes, in particular *Pratylenchus coffeae, Radopholus similis* and also *Pratylenchus giibbicaudatus, Pratylenchus loosi, Meloidogyne* spp., *Helicotylenchus multicinctus, Helicotylenchus dihystera* and *Rotylenchulus* spp.

The compounds of the formula (I) are particularly suitable for controlling pineapple nematodes, in particular *Pratylenchus zeae, Pratylenchus pratensis, Pratylenchus brachyurus, Pratylenchus goodeyi., Meloidogyne* spp., *Rotylenchulus reniformis* and also *Longidorus elongatus, Longidorus*

*laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides femiae, Criconemoides onoense* and *Criconemoides ornatum.*

The compounds of the formula (I) are particularly suitable for controlling grapevine nematodes, in particular *Pratylenchus vulnus, Meloidogyne arenaria, Meloidogyne incognita, Meloidogyne javanica, Xiphinema americanum, Xiphinema index* and also *Pratylenchus pratensis, Pratylenchus scribneri, Pratylenchus neglectus, Pratylenchus brachyurus, Pratylenchus thornei* and *Tylenchulus semipenetrans.*

The compounds of the formula (I) are particularly suitable for controlling nematodes in tree crops—pome fruit, in particular *Pratylenchus penetrans* and also *Pratylenchus vulnus, Longidorus elongatus, Meloidogyne incognita* and *Meloidogyne hapla.*

The compounds of the formula (I) are particularly suitable for controlling nematodes in tree crops—stone fruit, in particular *Pratylenchus penetrans, Pratylenchus vulnus, Meloidogyne arenaria, Meloidogyne hapla, Meloidogyne javanica, Meloidogyne incognita, Criconemella xenoplax* and also *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum* and *Hoplolaimus galeatus.*

The compounds of the formula (I) are particularly suitable for controlling nematodes in tree crops, sugar cane and rice, in particular *Trichodorus* spp., *Criconemella* spp. and also *Pratylenchus* spp., *Paratrichodorus* spp., *Meloidogyne* spp., *Helicotylenchus* spp., *Tylenchorhynchus* spp., *Aphelenchoides* spp., *Heterodera* spp., *Xiphinema* spp. and *Cacopaurus pestis.*

In the present context, the term "nematodes" also refers to nematodes damaging humans or animals.

Specific nematode species harmful to humans or to animals are:

Trichinellida, for example: *Trichuris* spp., *Capillaria* spp., *Paracapillaria* spp., *Eucoleus* spp., *Trichomosoides* spp., *Trichinella* spp.

From the order of the Tylenchida, for example: *Micronema* spp., *Strongyloides* spp.

From the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.

Many known nematicides also act against other parasitic helminths and are therefore used for controlling worms—not necessarily belonging to the group Nematoda—which are parasites in humans and animals. The present invention also relates to the use of the compounds of the formula (I) as anthelmintic medicaments. The pathogenic endoparasitic helminths include Platyhelmintha (e.g. Monogenea, cestodes and trematodes), Acanthocephala and Pentastoma. The following helminths may be mentioned as being preferred:

Monogenea: for example: *Gyrodactylus* spp., *Dactylogyrus* spp., *Polystoma* spp.

Cestodes: from the order of the Pseudophyllidea, for example: *Diphyllobothrium* spp., *Spirometra* spp., *Schistocephalus* spp., *Ligula* spp., *Bothridium* spp., *Diplogonoporus* spp.

From the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.

From the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

In the veterinary field and in animal husbandry, the administration of the compounds of the formula (I) is carried out in a known manner, directly or enterally, parenterally, dermally or nasally in the form of suitable use forms. Administration may be prophylactic or therapeutic.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulfoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, corn cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surfactants are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolyzates, lignosulfite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active compounds specified here with their common names are known and are described for example in "The Pesticide Manual", 16th ed., British Crop Protection Council 2012, or can be searched for on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers such as, for example, pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.
(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor.
(5) Allosteric activators of the nicotinergic acetylcholine receptor (nAChR), for example spinosyns, e.g. spinetoram and spinosad.
(6) Chloride channel activators, for example avermectins/milbemycins, e.g. abamectin, emamectin benzoate, lepimectin and milbemectin.
(7) Juvenile hormone imitators, for example, juvenile hormone analogues, e.g. hydroprene, kinoprene and methoprene or fenoxycarb or pyriproxyfen.
(8) Active compounds having unknown or nonspecific mechanisms of action, for example alkyl halides, e.g. methyl bromide and other alkyl halides; or chloropicrine or sulfuryl fluoride or borax or tartar emetic.
(9) Selective antifeedants, e.g. pymetrozine or flonicamid.
(10) Mite growth inhibitors, e.g. clofentezine, hexythiazox and diflovidazin or etoxazole.
(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.
(12) Oxidative phosphorylation inhibitors, ATP disruptors, for example diafenthiuron or organotin compounds, e.g. azocyclotin, cyhexatin and fenbutatin oxide or propargite or tetradifon.
(13) Oxidative phosphorylation decouplers that interrupt the H proton gradient, for example chlorfenapyr, DNOC and sulfluramid.
(14) Nicotinergic acetylcholine receptor antagonists, for example bensultap, cartap hydrochloride, thiocyclam, and thiosultap-sodium.
(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.
(16) Chitin biosynthesis inhibitors, type 1, for example buprofezin.
(17) Molting inhibitors (especially for Diptera, i.e. dipterans), for example cyromazine.
(18) Ecdysone receptor agonists, for example chromafenozide, halofenozide, methoxyfenozide and tebufenozide.
(19) Octopaminergic agonists, for example amitraz.
(20) Complex-III electron transport inhibitors, for example hydramethylnon or acequinocyl or fluacrypyrim.
(21) Complex-I electron transport inhibitors, for example METI acaricides, e.g. fenazaquin, fenpyroximate, pyrimidifen, pyridaben, tebufenpyrad and tolfenpyrad or rotenone (Derris).
(22) Voltage-gated sodium channel blockers, for example indoxacarb or metaflumizone.
(23) Inhibitors of acetyl-CoA carboxylase, for example tetronic and tetramic acid derivatives, e.g. spirodiclofen, spiromesifen and spirotetramat.
(24) Complex-IV electron transport inhibitors, for example phosphines, e.g. aluminum phosphide, calcium phosphide, phosphine and zinc phosphide or cyanide.
(25) Complex-II electron transport inhibitors, for example cyenopyrafen and cyflumetofen.
(28) Ryanodine receptor effectors, for example diamides, e.g. chlorantraniliprole, cyantraniliprole and flubendiamide,
further active compounds, for example afidopyropen, azadirachtin, benclothiaz, benzoximate, bifenazate, bromopropylate, chinomethionat, cryolite,
dicofol, diflovidazin, fluensulfone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; and also preparations based on *Bacillus firmus* (I-1582, BioNeem, Votivo), and also the following compounds: 3-bromo-N-{2-bromo-4-chloro-6-[(1-cyclopropylethyl) carbamoyl]phenyl}-1-(3-chloropyridin-2-yl)-H-pyrazole-5-carboxamide (known from WO2005/077934) and 1-{2-fluoro-4-methyl-5-[(2,2,2-trifluoroethyl)sulfinyl] phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino] ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl] carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl] carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl)sulfonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-H-5,8-epoxyimidazo[1,2-a]azepine (known from WO2010/069266), (2E)-1-[(6-chloropyridin-3-yl)methyl]-N'-nitro-2-pentylidenehydrazinecarboximid-amide (known from WO2010/060231), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides

The active compounds specified herein by their common name are known and described, for example, in "Pesticide Manual" or on the Internet (for example: http://www.alanwood.net/pesticides).

(1) Ergosterol biosynthesis inhibitors, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulfate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors), for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid.

(3) Respiration inhibitors (respiratory chain inhibitors) acting on complex III of the respiratory chain, for example (3.1) ametoctradin, (3.2) amisulbrom, (3.3) azoxystrobin, (3.4) cyazofamid, (3.5) coumethoxystrobin, (3.6) coumoxystrobin, (3.5) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy}imino)methyl]

phenyl}ethanamide, (3.26) (2E)-2-{2-[({[(1E)-1-(3-{[(E)-1-fluoro-2-phenylethenyl]oxy}oxy)phenyl)ethylidene]amino}oxy)methyl]phenyl}-2-(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl [(4-methoxyphenyl)imino]methyl}sulfanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide.

(4) Mitosis and cell division inhibitors, for example (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity such as, for example, (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulfate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copper-oxine, (5.28) propamidine, (5.29) propineb, (5.30) sulfur and sulfur preparations such as, for example, calcium polysulfide, (5.31) thiram, (5.32) tolylfluanid, (5.33) zineb, (5.34) ziram and (5.35) anilazine.

(6) Resistance inducers, for example (6.1) acibenzolar-S-methyl, (6.2) isotianil, (6.3) probenazole, (6.4) tiadinil and (6.5) laminarin.

(7) Amino acid and protein biosynthesis inhibitors, for example (7.1), (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors such as, for example, (8.1) fentin acetate, (8.2) fentin chloride, (8.3) fentin hydroxide and (8.4) silthiofam.

(9) Cell wall synthesis inhibitors, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Lipid and membrane synthesis inhibitors, for example (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluoroethyl {3-methyl-1-[(4-methylbenzoyl)amino]butan-2-yl}carbamate.

(12) Nucleic acid synthesis inhibitors, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors, for example (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers, for example (14.1) binapacryl, (14.2) dinocap, (14.3) ferimzone, (14.4) fluazinam and (14.5) meptyldinocap.

(15) Further compounds, for example (15.1) benthiazole, (15.2) bethoxazine, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat methylsulfate, (15.17) diphenylamine, (15.18) EcoMate, (15.19) fenpyrazamine, (15.20) flumetover, (15.21) fluorimid, (15.22) flusulfamide, (15.23) flutianil, (15.24) fosetyl-aluminum, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulfonyl)pyridine, (15.60) 2,3-dibutyl-6-chlorothieno [2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-

(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl] pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl-(2Z)-3-amino-2-cyano-3-phenyl acrylate, (15.78) N'-(4-{[3-(4-chlorobenzyl)-1,2,4-thiadiazol-5-yl]oxy}-2,5-dimethylphenyl)-N-ethyl-N-methyl-imidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1 S)-1,2,3,4-tetrahydronaphthalen-1-yl]-1,3-thiazole-4-carboxamide, (15.90) pentyl-{6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol, (15.93) quinolin-8-ol sulfate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl] nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl] nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulfonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulfanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel (2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulfanyl)-1-{[rel(2R,3 S)-3-(2-chlorophenyl)-2-(2,4-difluorophenyl)oxiran-2-yl]methyl}-1H-1,2,4-triazole, (15.136) 5-(allylsulfanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4- yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5 S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1 S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazole-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3 S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazole-5-amine. All the mixing components mentioned in classes (1) to (15), as the case may be, may form salts with suitable bases or acids if they are capable of doing so on the basis of their functional groups.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, in particular *B. cereus* strain CNCM 1-1562 or *Bacillus firmus*, strain 1-1582 (Accession number CNCM 1-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM 1-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), Pyrethrum/Pyrethrins, *Quassia amara*, *Quercus*, Quillaja, Regalia, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soybeans, potatoes, sugar beet, sugar cane, tomatoes, peas and other types of vegetable, cotton, tobacco, oilseed rape, and also fruit plants (with the fruits apples, pears, citrus fruits and grapevines). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are increased resistance of the plants against animal and microbial pests, such as insects, arachnids, nematodes, mites, slugs and snails owing, for example, to toxins formed in the plants, in particular those produced in the plants by the genetic material from

*Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulfonylureas, glyphosates or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soybeans, potatoes, sugar beet, sugar cane, tomatoes, peas and other types of vegetable, cotton, tobacco, oilseed rape and also fruit plants (with the fruits apples, pears, citrus fruits and grapevines), particular emphasis being given to maize, soybeans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signaling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in greenhouses, in forests or in horticulture. More particularly, this includes seed of cereals (for example wheat, barley, rye, millet and oats), maize, cotton, soybeans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), corn, soybeans, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate in this case from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. Thus, for example, it is possible to use seed which has been harvested, cleaned and dried down to a moisture content which allows storage. Alternatively, it is also possible to use seed which, after drying, has been treated with, for example, water and then dried again, for example priming.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are produced in a known manner, by mixing compounds of the formula (I) with customary additives, for example customary extenders and solvents or diluents, dyes, wetters, dispersants, emulsifiers, antifoams, preservatives, secondary thickeners, stickers, gibberellins and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical compounds. Preference is given to using alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of active agrochemical compounds. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of active agrochemical compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soybeans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favorable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods Include:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;

from the order of the Heteropterida, for example *Cimex* spp., *Triatoma* spp., *Rhodnius* spp., *Panstrongylus* spp.; and also nuisance and hygiene pests from the order of the Blattarida.

Arthropods Further Include:

from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa Include:

Mastigophora (Flagellata), for example Trypanosomatidae, for example *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, for example Trichomonadidae, for example *Giardia lamblia, G. canis*.

Sarcomastigophora (Rhizopoda) such as Entamoebidae, for example *Entamoeba histolytica*, Hartmanellidae, for example *Acanthamoeba* sp., *Harmanella* sp.

Apicomplexa (Sporozoa) such as Eimeridae, for example, *Eimeria acervulina, E. adenoides, E. alabamensis, E. anatis, E. anserina, E. arloingi, E. ashata, E. aubumensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuemii, Globidium* spec., *Isospora belli, I. canis, I. felis, I. ohioensis, I. rivolta, I.* spec., *I. suis, Cystisospora* spec., *Cryptosporidium* spec., in particular *C. parvum*; such as Toxoplasmadiidae, for example *Toxoplasma gondii, Hammondia heydomii, Neospora caninum, Besnoitia besnoitii*; such as Sarcocystidae, for example *Sarcocystis bovicanis, S. bovihominis, S. ovicanis, S. ovifelis, S. neurona, S.* spec., *S. suihominis*, such as Leucozoidae, for example *Leucozytozoon simondi*, such as Plasmodiidae, for example *Plasmodium berghei, P. falciparum, P. malariae, P. ovale, P. vivax, P.* spec., such as Piroplasmea, for example *Babesia argentina, B. bovis*,

*B. canis*, B. spec., *Theileria parva*, *Theileria* spec., such as Adeleina, for example *Hepatozoon canis*, *H*. spec.

Pathogenic endoparasites which are helminths include Platyhelmintha (e.g. Monogenea, cestodes and trematodes), nematodes, Acanthocephala, and Pentastoma. Further helminths include:

Monogenea: for example: *Gyrodactylus* spp., *Dactylogyrus* spp., *Polystoma* spp.

Cestodes: from the order of the Pseudophyllidea for example: *Diphyllobothrium* spp., *Spirometra* spp., *Schistocephalus* spp., *Ligula* spp., *Bothridium* spp., *Diplogonoporus* spp.

From the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

Nematodes: Trichinellida, for example: *Trichuris* spp., *Capillaria* spp., *Trichomosoides* spp., *Trichinella* spp.

From the order of the Tylenchida, for example: *Micronema* spp., *Strongyloides* spp.

From the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.

From the order of the Echinorhynchida, for example *Acanthocephalus* spp., *Echinorhynchus* spp., *Leptorhynchoides* spp.

Pentastoma: from the order of the Porocephalida, for example, *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in animal houses or in the hygiene sector.

Anthelmintic Mixing Components

The following anthelmintic mixing components may be mentioned by way of example:

anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulfoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, meniclopholan, nitroxynil;

from the class of the piperazinones, for example: praziquantel, epsiprantel;

From various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:
1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular *Onchocerca volvulus*;
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia* duttoni, tick-borne encephalitis, Q fever (*Coxiella burnetii*), babesioses (*Babesia canis canis*).

Examples of vectors in the context of the present invention are insects, such as aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forestry, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signaling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

They are used, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

Preparation Example 1

6-(3-Ethylpyridin-4-yl)-2,2-difluoro[1,3]dioxolo[4,5-g]quinoxaline (I-1)

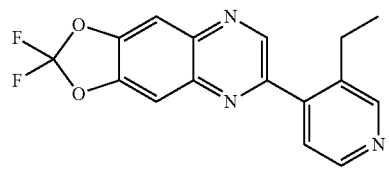 [SMILES: CCc1cnccc1-c1cnc2cc3c(cc2n1)OC(F)(F)O3]

100 mg (0.532 mmol) of 2,2-difluoro-1,3-benzodioxole-5,6-diamine and 180 mg (0.583 mmol) of 4-(bromoacetyl)-3-ethylpyridinium bromide (III-01) in 20 ml of ethanol are stirred under reflux for 18 h and then freed from the solvent under reduced pressure. The residue is made alkaline with conc. ammonia and then extracted with dichloromethane. The combined organic phases are separated off, dried over magnesium sulfate and freed from the solvent under reduced pressure.

Purification by column chromatography on silica gel 60 (Merck) using cyclohexane/ethyl acetate 1:1 v/v as mobile phase gives 21 mg of product as a beige solid (12.5% of theory, purity according to LC/MS 93%).

Preparation of 4-(bromoacetyl)-3-ethylpyridinium bromide (III-01)

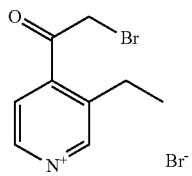

500 mg (3.35 mmol) of 1-(3-ethylpyridin-4-yl)ethanone are dissolved in 15 ml of chloroform and, after addition of 600 mg (3.76 mmol) of bromine, dissolved in 5 ml of chloroform, stirred at room temperature for 18 h. The mixture is then stirred at 40° C. for a further 2 h and freed from the solvent under reduced pressure. 1 g (96.6% of theory, purity according to 1H-NMR about 85%) of product remains as a dark-brown solid.

1H-NMR($D_6$-DMSO) δ ppm: 8.74-8.68(m, 2H), 7.85-7.84(m, 1H), 4.94(s, 2H), 2.73(q, 2H), 1.17(t, 3H)

Preparation Example 2

2-(3-Methylpyridin-4-yl)-6-(trifluoromethyl)quinoxaline (I-2)

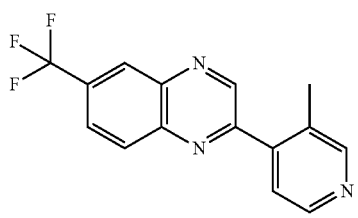 [SMILES: Cc1cnccc1-c1cnc2cc(C(F)(F)F)ccc2n1]

At room temperature, 190 mg (0.82 mmol) of 2-chloro-6-(trifluoromethyl)quinoxaline (VII-01) and 110 mg (0.157 mmol) of bis(triphenylphosphine)palladium(II) dichloride in 30 ml of dioxane are stirred for 3 h.

170 mg (1.24 mmol) of (3-methylpyridin-4-yl)boronic acid and 3.5 ml of 2-molar sodium carbonate solution are then added and the mixture is heated under reflux for 18 h. After cooling, water is added and the reaction mixture is extracted with dichloromethane. The combined organic phases are dried over $MgSO_4$ and freed from the solvent under reduced pressure.

Purification by column chromatography on silica gel 60 (Merck) using cyclohexane/ethyl acetate 1:1 v/v as mobile phase gives 39.2 mg of product as a beige solid (24.2% of theory, purity according to LC/MS 94.6%).

Preparation of 2-chloro-6-(trifluoromethyl)quinoxaline (VII-01)

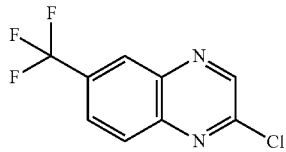 [SMILES: FC(F)(F)c1ccc2nc(Cl)cnc2c1]

8.4 g (54.78 mmol) of phosphoryl chloride are added dropwise to 1.40 g (6.54 mmol) of 6-(trifluoromethyl)quinoxalin-2(1H)-one (VIa-01) and 2.1 g (16.25 mmol) of N-ethyldiisopropylamine in 30 ml of toluene, and the mixture is stirred at 95° C. for a further 18 h. The residue that remains after rotary evaporation is stirred with water, made alkaline with solid potassium carbonate and extracted with dichloromethane. The combined organic phases are separated off, dried over sodium sulfate and freed from the solvent under reduced pressure. This leaves 1.37 g of product (90.1% of theory, purity 90% according to 1H-NMR) as residue.

1H-NMR($D_6$-DMSO) δ ppm: 9.17(s, 1H), 8.57(s, 1H), 8.29-8.28(m, 1H), 8.22-8.20(m, 1H)

Preparation of 6-(trifluoromethyl)quinoxalin-2(1H)-one (VIa-01) and 7-(trifluoromethyl)quinoxalin-2(1H)-one (VIa-02)

(VIa-01)

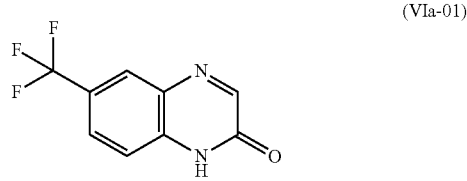

(VIa-02)

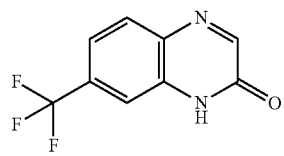

7.30 g (41.4 mmol) of 4-(trifluoromethyl)benzene-1,2-diamine and 5.9 g (64.1 mmol) of glyoxylic acid hydrate are in 100 ml of isopropanol and, after addition of 2 g of acetic acid, stirred at 50° C. for 18 h and then freed from the solvent under reduced pressure. The residue is stirred with water and the solid is filtered off with suction. What remains are 7.8 g (87.9% of theory) of an isomer mixture consisting of 38.9% (VIa-01) and 61.1% (VIa-02). The isomers are separated by preparative HPLC. Injection volume: In each case 1 g of isomer mixture is taken up in 21 ml of acetonitrile/35 ml of water/7 ml of THF and, after filtration, separated on Chromasil 100 C18 7 μm 250*50 mm 32/68 acetonitrile/water isocratic, flow rate: 100 ml/min.

A total of 1.4 g (VIa-01) (15.8% of theory, purity according to HPLC 97.7%) and 3.8 g (VIa-02) (42.8% of theory, purity according to HPLC 97.7%) are isolated.

(VIa-01): 13C-NMR(D$_6$-DMSO) δ ppm: 154.8, 153.5, 134.8, 131.2, 126.9, 125.9, 123.4, 116.9 log P(neutral): 1.71

(VIa-02): 13C-NMR(D$_6$-DMSO) δ ppm: 154.6, 154.5, 133.7, 132.0, 130.1, 130.0, 119.2, 112.7 log P(neutral): 1.65

Preparation Example 3

3-Chloro-2-[2-(ethylsulfanyl)phenyl]-6-(trifluoromethyl)quinoxaline (I-3)

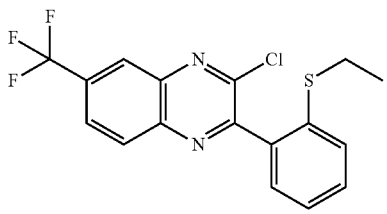 [SMILES: CCSc1ccccc1-c1nc2ccc(C(F)(F)F)cc2nc1Cl]

At room temperature, 100 mg (0.374 mmol) of 2,3-dichloro-6-(trifluoromethyl)quinoxaline and 35 mg (0.05 mmol) of bis(triphenylphosphine)palladium(II) dichloride in 20 ml of dioxane are stirred for 2 h.

75 mg (0.412 mmol) of [2-(ethylsulfanyl)phenyl]boronic acid and 1.7 ml of 2-molar sodium carbonate solution are then added and the mixture is heated under reflux for 18 h. After cooling, water is added and the reaction mixture is extracted with dichloromethane. The combined organic phases are dried over MgSO$_4$ and freed from the solvent under reduced pressure.

Purification by column chromatography on silica gel 60 (Merck) using cyclohexane/ethyl acetate 1:1 v/v as mobile phase gives 7 mg of product (5.1% of theory, purity according to LC/MS 100%).

Preparation Example 4

6-Chloro-7-(4-chlorophenyl)-2,2-difluoro[1,3]dioxolo[4,5-g]quinoxaline (I-4)

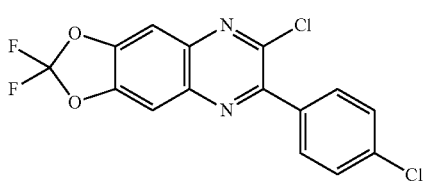 [SMILES: FC1(F)Oc2cc3nc(Cl)c(-c4ccc(Cl)cc4)nc3cc2O1]

1 g (6.52 mmol) of phosphoryl chloride is added dropwise to 220 mg (0.65 mmol) of 7-(4-chlorophenyl)-2,2-difluoro [1,3]dioxolo[4,5-g]quinoxalin-6(5H)-one (VIb-01) and 150 mg (1.09 mmol) of triethylamine hydrochloride, and the mixture is stirred at 95° C. for a further 18 h. The residue that remains after rotary evaporation is stirred with water, made alkaline with solid potassium carbonate and extracted with dichloromethane. The combined organic phases are separated off, dried over sodium sulfate and freed from the solvent under reduced pressure. This leaves 97 mg of product (41.8% of theory, purity 84.6% according to LC/MS) as a brown solid as residue.

Preparation of 7-(4-chlorophenyl)-2,2-difluoro [1,3]dioxolo [4,5-g]quinoxalin-6(5H)-one (VIb-01)

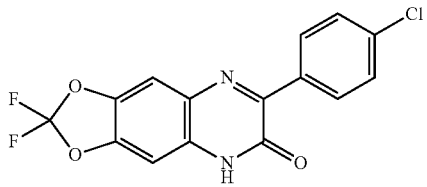 [SMILES: O=c1[nH]c2cc3c(cc2nc1-c1ccc(Cl)cc1)OC(F)(F)O3]

300 mg (1.59 mmol) of 2,2-difluoro-1,3-benzodioxole-5,6-diamine and 300 mg (1.63 mmol) of (4 chlorophenyl)(oxo)acetic acid in a mixture of 20 ml of isopropanol, 5 ml of dimethylformamide and 3 ml of water are stirred at 100° C. for 18 h. After cooling, the solvents are then distilled off under reduced pressure. The residue is stirred with water and the brown solid is filtered off with suction.

What remains are 450 mg of product (83.8% of theory) which is directly reacted further, without purification.
log P(HCOOH): 2.96

Preparation Example 5

2,2-Difluoro-6-[4-(trifluoromethyl)phenyl][1,3]dioxolo [4,5-g]quinoxaline (I-5)

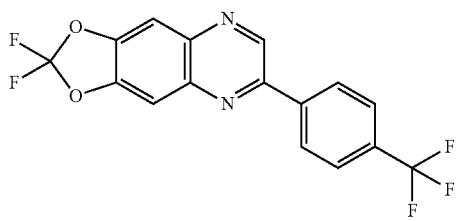 [SMILES: FC1(F)Oc2cc3ncc(-c4ccc(C(F)(F)F)cc4)nc3cc2O1]

200 mg (1.06 mmol) of 2,2-difluoro-1,3-benzodioxole-5,6-diamine and 220 mg (1.09 mmol) of oxo[4-(trifluoromethyl)phenyl]acetaldehyde in a mixture of 5 ml of dimethylformamide and 1 ml of water are stirred at 130° C. for 18 h. After cooling, the solvents are then distilled off under reduced pressure. The residue is stirred with water and the dark-brown solid is filtered off with suction.

This leaves 300 mg of product (79.7% of theory, purity 93.1% according to LC/MS).

Preparation Example 6

2,2-Difluoro-7-[4-(trifluoromethyl)phenyl][1,3]dioxolo [4,5-g]quinoxaline 5-oxide (I-6)

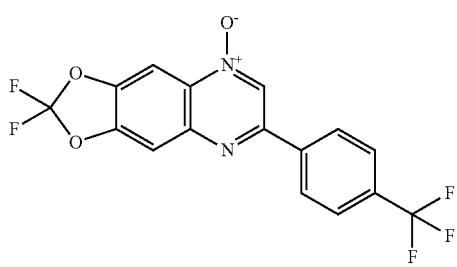 [SMILES: [O-][n+]1cc(-c2ccc(C(F)(F)F)cc2)nc2cc3c(cc21)OC(F)(F)O3]

115 mg (0.33 mmol) of 2,2-difluoro-6-[4-(trifluoromethyl)phenyl][1,3]dioxolo[4,5-g]quinoxaline and 3 g (30.87 mmol) of hydrogen peroxide, 35% strength aqueous solution, are stirred in 7 ml of acetic acid at 50° C. for 18 h.

After cooling, the mixture is stirred with water and the solid obtained is filtered off with suction.

Purification by column chromatography on a 25 g Chromabond flash column using ethyl acetate/cyclohexane (gradient 13-50% ethyl acetate) as mobile phase gives 28 mg of product as a white solid (23.3% of theory, purity according to LC/MS 93.1%).

1H-NMR($D_6$-DMSO): 9.48(s, 1H), 8.49-8.47(m, 2H), 8.42(s, 1H), 8.25(s, 1H), 7.97-7.95(m, 2H)

In analogy to the examples and according to the above-described preparation processes, the following compounds of the formula (I) can be obtained:

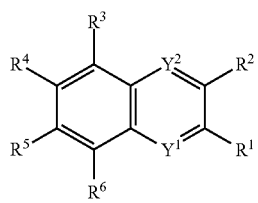

(I)

where $Y^1=Y^2=N$

| Ex. | $R^1$ | $R^2$ | $R^3$ | $R^4$ | $R^5$ | $R^6$ |
|---|---|---|---|---|---|---|
| I-7 | pyridin-4-yl | H | H | $CF_3$ | H | H |
| I-8 | pyridin-3-yl | H | H | $CF_3$ | H | H |
| I-9 | pyridin-4-yl | H | H | H | $CF_3$ | H |
| I-10 | 3-chloropyridin-4-yl | H | H | $CF_3$ | H | H |
| I-11 | 3-methoxypyridin-4-yl | H | H | $CF_3$ | H | H |
| I-12 | pyrimidin-5-yl | H | H | $CF_3$ | H | H |
| I-13 | 3-methylpyridin-4-yl | H | H | H | $-SO_2CH_3$ | H |
| I-14 | 2-(ethylthio)phenyl | H | H | $CF_3$ | H | H |
| I-15 | 2-(ethylsulfinyl)phenyl | H | H | $CF_3$ | H | H |
| I-16 | 2-(methylthio)phenyl | H | H | $CF_3$ | H | H |
| I-17 | 3-methylpyridin-4-yl | H | H | Cl | H | H |
| I-18 | pyridin-2-yl | H | H | $CF_3$ | H | H |
| I-19 | pyrimidin-5-yl | H | H | Cl | H | H |
| I-20 | 2-ethylphenyl | H | H | Cl | H | H |
| I-21 | 2-(trifluoromethyl)phenyl | H | H | Cl | H | H |

| Ex. | R¹ | R² | R³ | R⁴ | R⁵ | R⁶ |
|---|---|---|---|---|---|---|
| I-22 | 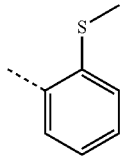 | H | H | Cl | H | H |
| I-23 | 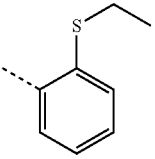 | H | H | Cl | H | H |
| I-24 | 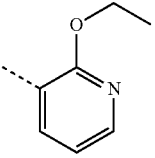 | H | H | CF₃ | H | H |
| I-25 | 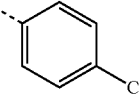 | H | H | CF₃ | H | H |
| I-26 | 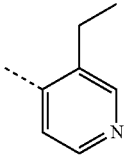 | H | H | CF₃ | H | H |
| I-27 | 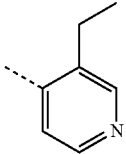 | H | H | H | CF₃ | H |
| I-28 | 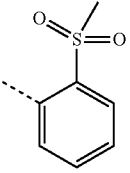 | H | H | Cl | H | H |
| I-29 | 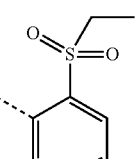 | H | H | Cl | H | H |
| I-30 | 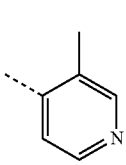 | H | H | H | CF₃ | H |
| I-31 | 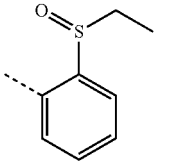 | H | H | Cl | H | H |
| I-32 | 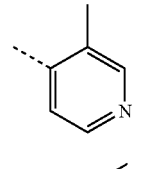 | H | H | —O—CF₂—O— | | H |
| I-33 | 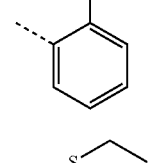 | H | H | CF₃ | H | H |
| I-34 | 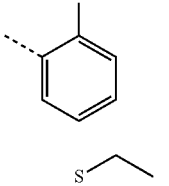 | H | H | —O—CF₂—O— | | H |
| I-35 | 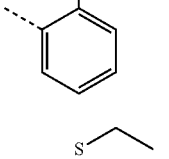 | H | H | H | —SO₂CH₃ | H |
| I-36 | 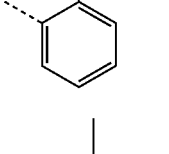 | H | H | H | CF₃ | H |
| I-37 | 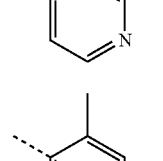 | Cl | H | CF₃ | H | H |
| I-38 | 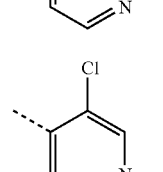 | Cl | H | H | CF₃ | H |
| I-39 | 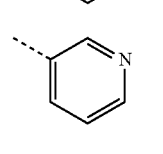 | H | H | Cl | H | H |
| I-40 |  | H | H | Cl | H | H |

-continued
| Ex. | R¹ | R² | R³ | R⁴ | R⁵ | R⁶ |
|---|---|---|---|---|---|---|
| I-41 | 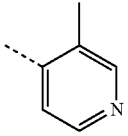 | H | H | Cl | Cl | H |
| I-42 | 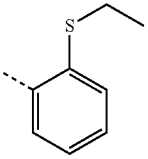 | H | H | Cl | Cl | H |
| I-43 | 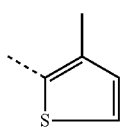 | H | H | H | CF₃ | H |
| I-44 | 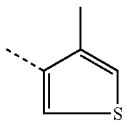 | H | H | H | CF₃ | H |
| I-45 | 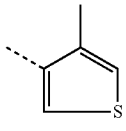 | H | H | CF₃ | H | H |
| I-46 | 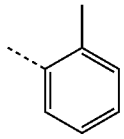 | H | H | CF₃ | H | H |
| I-47 | 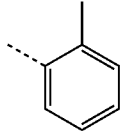 | H | H | H | CF₃ | H |
| I-48 | 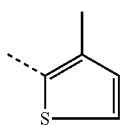 | H | H | CF₃ | H | H |
| I-49 | 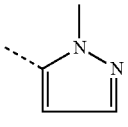 | H | H | CF₃ | H | H |
| I-50 | 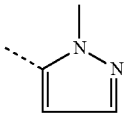 | H | H | H | CF₃ | H |
| I-51 | 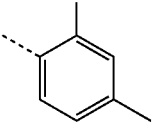 | H | H | H | CF₃ | H |
-continued
| Ex. | R¹ | R² | R³ | R⁴ | R⁵ | R⁶ |
|---|---|---|---|---|---|---|
| I-52 | 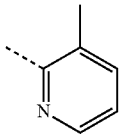 | H | H | CF₃ | H | H |
| I-53 | 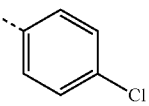 | Cl | H | H | CF₃ | H |
| I-56 | 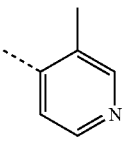 | H | H | CN | H | H |
| I-57 | 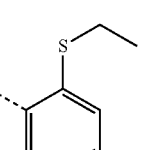 | H | H | CN | H | H |
| I-58 | 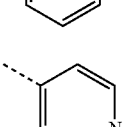 | 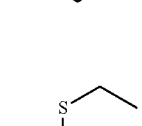 | H | CF₃ | H | H |
| I-59 | 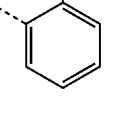 | 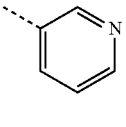 | H | —O—CF₂—O— | | H |
| I-60 | 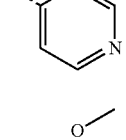 | CH₃ | H | CF₃ | H | H |
| I-61 | 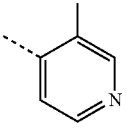 | H | H | CN | H | H |
| I-62 |  | H | H | H | CF₃ | H |
| I-63 |  | H | H | F | F | H |

-continued

| Ex. | R¹ | R² | R³ | R⁴ | R⁵ | R⁶ |
|---|---|---|---|---|---|---|
| I-64 | 3-methylpyridin-4-yl | 4-chlorophenyl | H | CF₃ | H | H |
| I-65 | 3-methylpyridin-4-yl | CH₃ | H | F | F | H |
| I-66 | 3-methylpyridin-4-yl | CH₃ | H | CF₃ | H | H |
| I-67 | 3-methylpyridin-4-yl | CH₃ | H | —O—CF₂—O— | | H |
| I-68 | 3-methylpyridin-4-yl | 4-chlorophenyl | H | H | CF₃ | H |
| I-69 | 2-chloropyridin-4-yl | H | H | Cl | H | H |
| I-70 | 3-chloropyridin-4-yl | H | H | F | F | H |
| I-71 | 3-chloropyridin-4-yl | H | H | Cl | Cl | H |
| I-72 | 3-chloropyridin-4-yl | H | H | —O—CF₂—O— | | H |
| I-73 | pyridin-4-yl | H | H | Cl | Cl | H |
| I-74 | pyridin-4-yl | H | H | —O—CF₂—O— | | H |

Analogously to Example (I-6) and in accordance with the preparation processes described above, the following compounds of the formula (I) can be obtained:

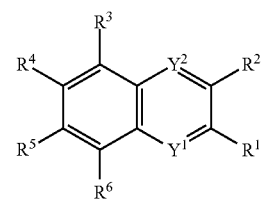

(I)

where $Y^1$=N and $Y^2$=N⁺—O⁻

| Ex. No. | R¹ | R² | R³ | R⁴ | R⁵ | R⁶ |
|---|---|---|---|---|---|---|
| I-54 | 2-fluoro-4-methylphenyl | H | H | H | CF₃ | H |
| I-55 | 3-methylpyridin-4-yl N-oxide | H | H | CF₃ | H | H |

The broken line denotes the bond to the quinoxaline derivative.

NMR data and log P values: log P (HCOOH)=log P[a] log P (neutral)=log P[b]

| Ex. No. | logP [b] | logP [a] | NMR [δ ppm] |
|---|---|---|---|
| I-1 | 3.23 | 2.34 | 1H-NMR (D₆-DMSO): 9.18 (s, 1H), 8.68 (s, 1H), 8.62-8.61 (m, 1H), 8.18 (s, 1H), 8.14 (s, 1H), 7.62-7.61 (m, 1H), 2.84-2.81 (q, 2H), 1.09 (t, 3H) |
| I-2 | 2.89 | 2.14 | 1H-NMR (D₆-DMSO): 9.41 (s, 1H), ), 8.68 (s, 1H), 8.65-8.64 (m, 1H), 8.59 (s, 1H), 8.41-8.39 (m, 1H), 8.22-8.20 (m, 1H), 7.73-7.72 (m, 1H), 2.50 (s, 3H, in the DMSO signal) |
| I-3 | | 5.20 | 1H-NMR (D₆-DMSO): 8.60-8.58 (m, 1H), 8.40-8.35 (m, 1H), 8.26-8.20 (m, 1H), 7.65-7.63 (m, 1H), 7.59-7.53 (m, 2H), 7.46-7.42 (m, 1H), 2.92-2.87 (q, 2H), 1.11 (t, 3H) |

| Ex. No. | logP [b] | logP [a] | NMR [δ ppm] |
| --- | --- | --- | --- |
| I-4 | | 5.27 | 1H-NMR (D$_6$-DMSO): 8.20-8.16 (m, 2H), 7.88-7.86 (m, 2H), 7.66-7.64 (m, 2H) |
| I-5 | | 5.02 | 1H-NMR (D$_6$-DMSO): 9.65 (s, 1H), 8.54-8.52 (m, 2H), 8.15-8.13 (m, 2H), 7.98-7.96 (m, 2H) |
| I-6 | | 4.12 | 13C-NMR (D$_6$-DMSO): 151.8; 146.5; 145.2; 142.8; 138.6; 133.7; 130.6; 128.0; 127.8; 125.9; 124.0; 108.9; 98.7 |
| I-7 | 2.75 | 2.17 | 1H-NMR (D$_6$-DMSO): 9.84 (s, 1H), 8.88-8.86 (m, 2H), 8.58 (s, 1H), 8.45-8.42 (m, 1H), 8.36-8.34 (m, 2H), 8.22-8.20 (m, 1H) |
| I-8 | | 2.46 | 1H-NMR (D$_6$-DMSO): 9.83 (s, 1H), 9.56-9.55 (m, 1H), 8.81-8.72 (m, 2H), 8.57 (s, 1H), 8.40-8.37 (m, 1H), 8.17-8.14 (m, 1H), 7.69-7.66 (m, 1H) |
| I-9 | 2.75 | 2.13 | 1H-NMR (D$_6$-DMSO): 9.84 (s, 1H), 8.87-8.86 (m, 2H), 8.60 (s, 1H), 8.41-8.40 (m, 1H), 8.34-8.33 (m, 2H), 8.20 (m, 1H) |
| I-10 | | 3.27 | 1H-NMR (D$_6$-DMSO): 9.48 (s, 1H), 8.92 (s, 1H), 8.80-8.79 (m, 1H), 8.62 (s, 1H), 8.46-8.43 (m, 1H), 8.27-8.24 (m, 1H), 7.88-7.86 (m, 1H) |
| I-11 | | 2.59 | 1H-NMR (D$_6$-DMSO): 9.55 (s, 1H), 8.70 (s, 1H), 8.56 (s, 1H), 8.48-8.47 (m, 1H), 8.42-8.40 (m, 1H), 8.20-8.18 (m, 1H), 7.86 (m, 1H), 4.05 (s, 3H) |
| I-12 | | 2.33 | 1H-NMR (D$_6$-DMSO): 9.87-9.86 (m, 1H), 9.73-9.72 (m, 2H), 9.41 (m, 1H), 8.60-8.58 (m, 1H), 8.44-8.39 (m, 1H), 8.22-8.18 (m, 1H) |
| I-13 | 1.34 | 0.72 | 1H-NMR (D$_6$-DMSO): 9.44 (s, 1H), 8.71-8.66 (m, 3H), 8.46-8.44 (m, 1H), 8.38-8.36 (m, 1H), 7.75-7.74 (m, 1H), 3.43 (s, 3H), 2.50 (s, 3H, in the DMSO signal) |
| I-14 | 4.78 | 4.80 | 1H-NMR (D$_6$-DMSO): 9.35-9.34 (m, 1H), 8.54-8.51 (m, 1H), 8.39-8.34 (m, 1H), 8.19-8.16 (m, 1H), 7.74-7.56 (m, 3H), 7.47-7.43 (m, 1H), 2.96-2.91 (q, 2H), 1.14 (t, 3H) |
| I-15 | 2.78 | 2.79 | 1H-NMR (D$_6$-DMSO): 9.74 (s, 1H), 8.58-7.79 (m, 7H), 3.64-3.57 (m, 1H), 3.04-2.95 (m, 1H), 1.28 (t, 3H) |
| I-16 | 4.31 | 4.45 | 1H-NMR (D$_6$-DMSO): 9.38 (s, 1H), 8.50 (s, 1H), 8.40-8.37 (m, 1H), 8.19-8.16 (m, 1H), 7.75-7.74 (m, 1H), 7.60-7.58 (m, 2H), 7.43-7.39 (m, 1H), 2.46 (s, 3H) |
| I-17 | 2.58 | 1.69 | 1H-NMR (D$_6$-DMSO): 9.28 (s, 1H), 8.65 (s, 1H), 8.63-8.61 (m, 1H), 8.32-8.29 (m, 1H), 8.22-8.20 (m, 1H), 7.99-7.96 (m, 1H), 7.70-7.68 (m, 1H), 2.46 (s, 3H) |
| I-18 | 3.75 | 3.72 | 1H-NMR (D$_6$-DMSO): 10.03-10.02 (m, 1H), 8.87-8.86 (m, 1H), 8.61-8.55 (m, 2H), 8.42-8.38 (m, 1H), 8.21-8.09 (m, 2H), 7.67-7.63 (m, 1H) |
| I-19 | | 2.01 | 1H-NMR (D$_6$-DMSO): 9.74 (s, 1H), 9.68 (s, 1H), 9.38 (s, 1H), 8.29-8.23 (m, 2H), 7.99-7.96 (m, 1H), 7.65-7.55 (m, 1H) |
| I-20 | | 4.73 | 1H-NMR (D$_6$-DMSO): 9.16 (s, 1H), 8.26 (m, 1H), 8.16-8.14 (m, 1H), 7.96-7.93 (m, 1H), 7.60-7.58 (m, 1H), 7.52-7.38 (m, 3H), 2.79-2.73 (q, 2H), 1.10 (t, 3H) |
| I-21 | | 4.17 | 1H-NMR (CDCl$_3$): 8.99 (s, 1H), 8.19-8.18 (m, 1H), 8.11-8.09 (m, 1H), 7.88-7.86 (m, 1H), 7.79-7.61 (m, 4H) |
| I-22 | | 4.08 | 1H-NMR (D$_6$-DMSO): 9.24 (s, 1H), 8.26-8.25 (m, 1H), 8.16-8.14 (m, 1H), 7.95-7.92 (m, 1H), 7.71-7.69 (m, 1H), 7.57-7.56 (m, 2H), 7.41-7.37 (m, 1H), 2.45 (s, 3H) |
| I-23 | | 4.56 | 1H-NMR (D$_6$-DMSO): 9.21 (s, 1H), 8.25 (m, 1H), 8.17-8.15 (m, 1H), 7.95-7.92 (m, 1H), 7.69-7.53 (m, 3H), 7.44-7.40 (m, 1H), 2.95-2.90 (q, 2H), 1.14 (t, 3H) |
| I-24 | | 4.59 | 1H-NMR (D$_6$-DMSO): 9.63-9.62 (m, 1H), 8.53-8.52 (m, 1H), 8.41-8.34 (m, 3H), 8.18-8.14 (m, 1H), 7.29-7.25 (m, 1H), 4.54-4.48 (q, 2H), 1.39 (t, 3H) |
| I-25 | | 4.99 | 1H-NMR (D$_6$-DMSO): 9.78 (s, 1H), 8.53 (s, 1H), 8.45-8.41 (m, 2H), 8.37-8.35 (m, 1H), 8.14-8.11 (m, 1H), 7.73-7.70 (m, 2H) |
| I-26 | 3.28 | 2.53 | 1H-NMR (D$_6$-DMSO): 9.37 (s, 1H), 8.71 (s, 1H), 8.65-8.64 (m, 1H), 8.60 (s, 1H), 8.40-8.38 (m, 1H), 8.23-8.20 (m, 1H), 7.69-7.67 (m, 1H), 2.84 (q, 2H), 1.12 (t, 3H) |
| I-27 | | | 1H-NMR (CDCl$_3$): 9.11 (s, 1H), 8.72 (s, 1H), 8.66 (m, 1H), 8.51 (s, 1H), 8.29 (m, 1H), 8.04-8.02 (m, 1H), 7.45-7.44 (m, 1H), 2.90-2.84 (q, 2H), 1.22 (t, 3H) |
| I-28 | 2.52 | 2.52 | 1H-NMR (D$_6$-DMSO): 9.15 (s, 1H), 8.32-8.30 (m, 1H), 8.20-8.17 (m, 2H), 7.99-7.82 (m, 4H), 3.47 (s, 3H) |
| I-29 | 2.82 | 2.81 | 1H-NMR (D$_6$-DMSO): 9.14 (s, 1H), 8.30 (m, 1H), 8.19-7.82 (m, 6H), 3.64-3.57 (m, 2H), 1.17 (t, 3H) |
| I-30 | 2.89 | 2.12 | 13C-NMR (D$_6$-DMSO): 153.5; 151.8; 148.0; 147.7; 142.8; 142.0; 140.0; 131.4; 130.9; 127.2; 126.0; 125.9; 123.7; 123.5; 16.6 |
| I-31 | 2.65 | 2.66 | 1H-NMR (D$_6$-DMSO): 9.62 (s, 1H), 8.37-7.76 (m, 7H), 3.63-3.54 (m, 1H), 3.00-2.91 (m, 1H), 1.32 (t, 3H) |
| I-32 | 2.85 | 1.99 | 1H-NMR (D$_6$-DMSO): 9.23 (s, 1H), 8.65 (s, 1H), 8.62-8.61 (m, 1H), 8.18-8.16 (m, 2H), 7.68-7.66 (m, 1H), 2.46 (s, 3H) |
| I-33 | 4.89 | 4.92 | 1H-NMR (D$_6$-DMSO): 9.30-9.29 (m, 1H), 8.51 (s, 1H), 8.41-8.38 (m, 1H), 8.19-8.15 (m, 1H), 7.63-7.62 (m, 1H), 7.54-7.41 (m, 3H), 2.82-2.74 (q, 2H), 1.11 (t, 3H) |
| I-34 | | 4.73 | 1H-NMR (D$_6$-DMS0): 9.15 (s, 1H), 8.13 (s, 1H), 8.10 (s, 1H), 7.66-7.61 (m, 2H), 7.56-7.52 (m, 1H), 7.43-7.41 (m, 1H), 2.95-2.89 (q, 2H), 1.14 (t, 3H) |

-continued

| Ex. No. | logP [b] | logP [a] | NMR [δ ppm] |
|---|---|---|---|
| I-35 | 2.78 | 2.85 | 1H-NMR (D$_6$-DMSO): 9.38 (s, 1H), 8.65-8.64 (m, 1H), 8.42-8.40 (m, 1H), 8.35-8.32 (m, 1H), 7.75-7.73 (m, 1H), 7.67-7.66 (m, 1H), 7.60-7.56 (m, 1H), 7.47-7.43 (m, 1H), 3.43 (s, 3H), 2.97-2.91 (q, 2H), 1.15 (t, 3H) |
| I-36 | | 4.79 | 1H-NMR (D$_6$-DMSO): 9.35 (s, 1H), 8.51 (s, 1H), 8.39-8.37 (m, 1H), 8.19-8.16 (m, 1H), 7.73-7.56 (m, 3H), 7.47-7.43 (m, 1H), 2.96-2.91 (q, 2H), 2.16-2.10 (m, 1H), 1.14 (t, 3H) |
| I-37 | | 2.94 | 13C-NMR (CD$_3$CN): 155.0; 152.6; 148.0; 148.6; 148.3; 144.6; 142.9; 141.6; 133.2; 132.3; 131.8; 127.3; 124.7; 123.9; 16.5 |
| I-38 | | 2.88 | 1H-NMR (D$_6$-DMSO): 8.67 (s, 1H), 8.63-8.61 (m, 2H), 8.40-8.38 (m, 1H), 8.29-8.26 (m, 1H), 7.56-7.55 (m, 1H) 2.19 (s, 3H) |
| I-39 | | 2.99 | 1H-NMR (D$_6$-DMSO): 9.35 (s, 1H), 8.90 (s, 1H), 8.77-8.76 (m, 1H), 8.33-8.32 (m, 1H), 8.25-8.23 (m, 1H), 8.02-7.99 (m, 1H), 7.85-7.84 (m, 1H) |
| I-40 | 2.43 | 2.01 | 1H-NMR (D$_6$-DMSO): 9.70 (s, 1H), 9.51 (m, 1H), 8.78-8.77 (m, 1H), 8.71-8.68 (m, 1H), 8.26-8.20 (m, 2H), 7.96-7.93 (m, 1H), 7.67-7.63 (m, 1H) |
| I-41 | 3.29 | 2.51 | 1H-NMR (D$_6$-DMSO): 9.31 (s, 1H), 8.66 (s, 1H), 8.64-8.62 (m, 1H), 8.55-8.53 (m, 2H), 7.70-7.69 (m, 1H), 2.46 (s, 3H) |
| I-42 | 5.48 | 5.38 | 1H-NMR (D$_6$-DMSO): 9.24 (s, 1H), 8.49 (s, 1H), 8.45 (s, 1H), 7.70-7.63 (m, 2H), 7.59-7.54 (m, 1H), 7.45-7.41 (m, 1H), 2.96-2.90 (q, 2H), 1.14 (t, 3H) |
| I-43 | 4.66 | 4.65 | 1H-NMR (D$_6$-DMSO): 9.43 (s, 1H), 8.42 (s, 1H), 8.32-8.30 (m, 1H), 8.09-8.06 (m, 1H), 7.82-7.81 (m, 1H), 7.17-7.16 (m, 1H), 2.69 (s, 3H) |
| I-44 | | 4.57 | 1H-NMR (D$_6$-DMSO): 9.53 (s, 1H), 8.52 (m, 1H), 8.44 (s, 1H), 8.33-8.31 (m, 1H), 8.10-8.07 (m, 1H), 7.44-7.43 (m, 1H), 2.61 (s, 3H) |
| I-45 | | 4.57 | 1H-NMR (D$_6$-DMSO): 9.52 (s, 1H), 8.54 (m, 1H), 8.47 (m, 1H), 8.30-8.28 (m, 1H), 8.14-8.11 (m, 1H), 7.44-7.43 (m, 1H), 2.61 (d, 3H) |
| I-46 | | 4.48 | 1H-NMR (D$_6$-DMSO): 9.33 (s, 1H), 8.55 (s, 1H), 8.37-8.34 (m, 1H), 8.19-8.16 (m, 1H), 7.70-7.68 (m, 1H), 7.51-7.41 (m, 3H), 2.47 (s, 3H) |
| I-47 | 4.41 | 4.47 | 1H-NMR (D$_6$-DMSO): 9.34 (s, 1H), 8.53 (s, 1H), 8.40-8.37 (m, 1H), 8.17-8.15 (m, 1H), 7.70-7.68 (m, 1H), 7.50-7.41 (m, 3H), 2.47 (s, 3H) |
| I-48 | | 4.67 | 1H-NMR (D$_6$-DMSO): 9.42 (s, 1H), 8.47 (s, 1H), 8.27-8.25 (m, 1H), 8.13-8.10 (m, 1H), 7.84-7.83 (m, 1H), 7.18-7.16 (m, 1H), 2.70 (s, 3H) |
| I-49 | 3.05 | 3.07 | 1H-NMR (D$_6$-DMSO): 9.57 (s, 1H), 8.50 (s, 1H), 8.36-8.34 (m, 1H), 8.18-8.15 (m, 1H), 7.68-7.67 (m, 1H), 7.41 (d, 1H), 4.36 (s, 3H) |
| I-50 | 3.00 | 3.02 | 1H-NMR (D$_6$-DMSO): 9.58 (s, 1H), 8.54 (s, 1H), 8.35-8.33 (m, 1H), 8.14-8.11 (m, 1H), 7.67 (d, 1H), 7.40-7.39 (d, 1H), 4.36 (s, 3H) |
| I-51 | | 4.97 | 1H-NMR (D$_6$-DMSO): 9.46-9.45 (m, 1H), 8.54 (s, 1H), 8.38-8.36 (m, 1H), 8.17-8.14 (m, 1H), 8.04-8.00 (d, 1H), 7.34-7.29 (m, 2H), 2.45 (s, 3H) |
| I-52 | | 3.69 | 1H-NMR (D$_6$-DMSO): 9.64 (s, 1H), 8.69-8.68 (m, 1H), 8.55 (s, 1H), 8.38-8.36 (m, 1H), 8.20-8.18 (m, 1H), 7.92-7.90 (m, 1H), 7.54-7.51 (m, 1H), 2.70 (s, 3H) |
| I-53 | | 5.31 | 1H-NMR (CDCl$_3$): 8.37 (m, 1H), 8.28-8.26 (m, 1H), 8.00 (m, 1H), 7.86-7.85 (m, 2H), 7.55-7.53 (m, 2H) |
| I-54 | 4.00 | 4.04 | 1H-NMR (D$_6$-DMSO): 9.07 (m, 1H), 8.66-8.65 (m, 1H), 8.58 (s, 1H), 8.14-8.11 (m, 1H), 8.05-8.01 (m, 1H), 7.32-7.28 (m, 2H), 2.43 (s, 3H) |
| I-55 | | 1.59 | 13C-NMR (D$_6$-DMSO): 155.5; 155.4; 139.8; 136.8; 135.9; 135.1; 132.2; 131.9; 131.0; 127.8; 127.2; 123.5; 116.6; 17.1 |
| I-56 | 1.81 | 1.17 | 1H-NMR (D$_6$-DMSO): 9.40 (s, 1H), 8.84-8.82 (m, 1H), 8.67-8.64 (m, 2H), 8.37-8.33 (m, 1H), 8.26-8.23 (m, 1H), 7.73-7.71 (m, 1H), 2.47 (s, 3H) |
| I-57 | 3.55 | 3.60 | 1H-NMR (D$_6$-DMSO): 9.33 (s, 1H), 8.75 (m, 1H), 8.33-8.27 (m, 2H), 7.71-7.44 (m, 4H), 2.93 (q, 2H), 1.14 (t, 3H) |
| I-58 | | 2.06 | 1H-NMR (D$_6$-DMSO): 8.65-8.64 (m, 4H), 8.48-8.46 (m, 1H), 8.26-8.24 (m, 1H), 7.84-7.83 (m, 1H), 7.53-7.51 (m, 4H) |
| I-59 | | 6.23 | 1H-NMR (D$_6$-DMSO): 8.17 (s, 1H), 8.14 (m, 1H), 7.52-7.07 (m, 8H), 2.85-2.80 (q, 1H), 1.14 (t, 3H) |
| I-60 | | 2.39 | 1H-NMR (CDCl$_3$): 8.98 (s, 1H), 8.79-8.78 (m, 1H), 8.45 (s, 1H), 8.21-8.19 (m, 1H), 8.07-8.04 (m, 1H), 7.97-7.94 (m, 1H), 7.53-7.52 (m, 1H), 2.87 (s, 3H) |
| I-61 | | 1.19 | 1H-NMR (D$_6$-DMSO): 9.83 (s, 1H), 8.87-8.82 (m, 3H), 8.38-8.31 (m, 3H), 8.26-8.22 (m, 1H) |
| I-62 | | 2.60 | 1H-NMR (CDCl$_3$): 9.54 (s, 1H), 8.56-8.50 (m, 3H), 8.30-8.27 (m, 1H), 7.99-7.97 (m, 1H), 7.92-7.90 (m, 1H), 4.08 (s, 3H) |
| I-63 | | 1.55 | 1H-NMR (CDCl$_3$): 9.01 (s, 1H), 8.66 (broad, 2H), 7.96-7.89 (m, 2H), 7.49-7.47 (m, 1H), 2.49 (s, 3H) |
| I-64 | | 4.03 | 1H-NMR (CDCl$_3$): 8.56-8.52 (m, 2H), 8.30-8.28 (m, 1H), 8.02-7.99 (m, 1H), 7.46-7.44 (m, 2H), 7.33-7.26 (m, 4H), 2.04 (s, 3H) |
| I-65 | | 1.58 | 1H-NMR (CDCl$_3$): 8.65-8.64 (m, 2H), 7.86-7.81 (m, 2H), 7.23-7.21 (m, 1H), 2.54 (s, 3H), 2.15 (s, 3H) |
| I-66 | | 2.15 | 1H-NMR (CDCl$_3$): 8.67 (s, 1H), 8.65-8.63 (m, 1H), 8.42 (m, 1H), 8.23-8.21 (m, 1H), 7.97-7.93 (m, 1H), 7.25-7.23 (m, 1H), 2.60 (s, 3H), 2.17 (s, 3H) |
| I-67 | | 2.02 | 1H-NMR (CDCl$_3$): 8.65 (s, 1H), 8.62 (m, 1H), 7.67-7.66 (m, 2H), 7.22 (m, 1H), 2.54 (s, 3H), 2.15 (s, 3H) |

-continued

| Ex. No. | logP [b] | logP [a] | NMR [δ ppm] |
|---|---|---|---|
| I-68 | | 3.94 | 13C-NMR (CDCl$_3$): 153.3; 152.4; 151.6; 147.4; 145.3; 142.4; 139.4; 136.1; 135.4; 131.8; 130.5; 130.3; 128.5; 126.9; 126.2; 123.5; 123.2; 16.2 |
| I-69 | | 3.52 | 1H-NMR (D$_6$-DMSO): 9.76 (s, 1H), 8.68-8.67 (m, 1H), 8.42 (s, 1H), 8.34-8.25 (m, 3H), 8.01-7.98 (m, 1H) |
| I-70 | | 2.72 | 1H-NMR (D$_6$-DMSO): 9.35 (s, 1H), 8.91 (s, 1H), 8.78-8.77 (m, 1H), 8.36-8.31 (m, 2H), 7.84-7.83 (m, 1H) |
| I-71 | | 3.78 | 1H-NMR (D$_6$-DMSO): 9.38 (s, 1H), 8.91 (s, 1H), 8.79-8.78 (m, 1H), 8.59-8.58 (m, 2H), 7.85-7.84 (m, 1H) |
| I-72 | | 3.24 | 1H-NMR (D$_6$-DMSO): 9.31 (s, 1H), 8.90 (s, 1H), 8.77-8.76 (m, 1H), 8.21 (m, 2H), 7.84-7.83 (m, 1H) |
| I-73 | | 2.53 | 1H-NMR (D$_6$-DMSO): 9.74 (s, 1H), 8.86-8.84 (m, 2H), 8.55-8.53 (m, 2H), 8.30-8.29 (m, 2H) |
| I-74 | | 1.98 | 1H-NMR (D$_6$-DMSO): 9.67 (s, 1H), 8.83-8.82 (m, 2H), 8.29-8.27 (m, 2H), 8.18-8.16 (m, 2H) |

The log P values are determined in accordance with EEC Directive 79/831 Annex V.A8 by HPLC (High Performance Liquid Chromatography) using reversed-phase columns (C 18) by the following methods:

[a] The LC-MS determination in the acidic range is carried out at pH 2.7 with 0.1% aqueous formic acid and acetonitrile (contains 0.1% formic acid) as eluents; linear gradient from 10% acetonitrile to 95% acetonitrile. Called log P (HCOOH) in the table.

[b] LC-MS determination in the neutral range is carried out at pH 7.8 with 0.001 molar aqueous ammonium hydrogencarbonate solution and acetonitrile as eluents; linear gradient from 10% acetonitrile to 95% acetonitrile. Called log P (neutral) in the table.

Calibration is carried out using unbranched alkan-2-ones (having 3 to 16 carbon atoms) with known log P values (log P values determined on the basis of the retention times by linear interpolation between two successive alkanones).

The lambda-max values were determined in the maxima of the chromatographic signals using the UV spectra from 200 nm to 400 nm.

The NMR data of selected examples are stated in classic form (δ values, number of hydrogen atoms, multiplet splitting).

In each case, the solvent in which the NMR spectrum is recorded is stated.

Further Examples of the Preparation of Starting Materials

Preparation of Compounds of the Formula (VIa)

Preparation of 2,2-difluoro[1,3]dioxolo[4,5-g]quinoxalin-6(5H)-one (VIa-03)

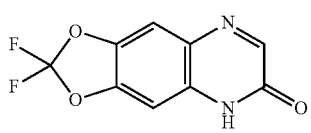 [SMILES: O=c1cnc2cc3c(cc2[nH]1)OC(F)(F)O3]

1.60 g (13.3 mmol) of 2,2-difluoro-1,3-benzodioxole-5,6-diamine and 1.90 g (10.2 mmol) of methyl 2-hydroxy-2-methoxyacetate are dissolved in 100 ml of ethanol and the mixture is stirred at room temperature for 2 h.

The mixture is heated to reflux, 35 ml of a 5.4-molar sodium methoxide solution are then added dropwise and the mixture is then heated under reflux for a further 18 h.

After cooling, the solvent is then removed under reduced pressure, 200 ml of water are added to the residue that remains and the mixture is stirred for 3 h. After acidification with conc. hydrochloric acid, the dark-brown solid is filtered off with suction. This leaves 2.2 g (95.3% of theory, purity according to LC/MS 91.1%).

log P(HCOOH): 1.49; log P(neutral): 1.33; 1H-NMR(D$_6$-DMSO) δ ppm: 12.69(broad, 1H), 8.17(s, 1H), 7.86(s, 1H), 7.28 (s, 1H)

Preparation of 6,7-difluoroquinoxalin-2(1H)-one (VIa-04)

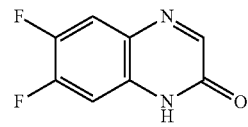

After addition of 1 ml of acetic acid, 3.00 g (21.1 mmol) of 4,5-difluorobenzene-1,2-diamine and 3.00 g (32.5 mmol) of glyokylic acid monohydrate in 100 ml of isopropanol are stirred at 50° C. for 18 h.

After cooling, the solvent is then removed under reduced pressure. The residue is stirred with water and the dark-brown solid is filtered off with suction.

This leaves 3.37 g (87.7% of theory, purity according to 1H-NMR 100%).

1H-NMR(D$_6$-DMSO) δ ppm: 12.54(broad, 1H), 8.19(s, 1H), 7.95-7.90(m, 1H), 7.26-7.21 (m, 1H)

Preparation of 6,7-difluoro-3-methylquinoxalin-2(1H)-one (VIa-05)

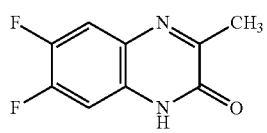

700 mg (4.86 mmol) of 4,5-difluorobenzene-1,2-diamine and 600 mg (6.81 mmol) of 2-oxopropionic acid in a mixture of 5 ml of dimethylformamide and 1 ml of water are stirred under reflux for 18 h.

After cooling, the solvent is then removed under reduced pressure. The residue is stirred with water and the brown solid is filtered off with suction.

This leaves 890 mg (93.4% of theory, purity according to 1H-NMR >95%).

1H-NMR($D_6$-DMSO) δ ppm: 12.42(s, 1H), 7.84-7.79(m, 1H), 7.22-7.17(m, 1H), 2.39(s, 3H)

Preparation of Compounds of the Formula (VII)

Preparation of 6,7-dichloro-2-iodoquinoxaline (VII-02)

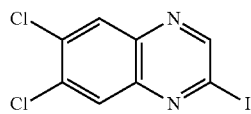 [SMILES: Clc1cc2ncc(I)nc2cc1Cl]

7.20 g (33 mmol) of 5,6-dichloroquinoxalin-2(1H)-one and 12.99 g (35 mmol) of tetrabutylammonium iodide are dissolved in 200 ml of toluene and, after addition of 12.36 g of phosphorus pentoxide (87 mmol), stirred under reflux for 18 h. After cooling, a solid mass forms. Following the addition of 200 ml of water, the toluene/water mixture is stirred for 3 h and filtered. Several times more, the organic phase is stirred with water and extracted. The combined organic phases are dried over sodium sulfate and freed from the solvent under reduced pressure. This leaves 6.1 g (54.1% of theory, purity according to GC/MS 96.4%) of product as a light-yellow solid.

1H-NMR($D_6$-DMSO) δ ppm: 9.15(s, 1H), 8.38(s, 1H), 8.36(s, 1H)

The preparation processes described above can be used to obtain the compounds of the formula (VI), for example the following compounds of the formula (VI):

2,2-Difluoro-7-methyl[1,3]dioxolo [4,5-g]quinoxalin-6(5H)-one (VIa-06)

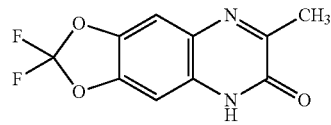 [SMILES: Cc1nc2cc3c(cc2[nH]c1=O)OC(F)(F)O3]

1H-NMR($D_6$-DMSO) δ ppm: 12.50(s, 1H), 7.76(s, 1H), 7.19(s, 1H), 2.39(s, 3H)

The preparation processes described above can be used to obtain the compounds of the formula (VII), for example the following compounds of the formula (VII):

6-Chloro-2-iodoquinoxaline (VII-03)

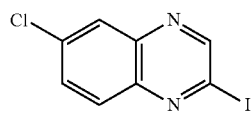 [SMILES: Clc1ccc2nc(I)cnc2c1]

1H-NMR ($D_6$-DMSO) δ ppm: 9.13(s, 1H), 8.16-8.15(m, 1H), 8.08-8.05(m, 1H), 7.90-7.87(m, 1H)

2-Iodo-6-(trifluoromethyl)quinoxaline (VII-04)

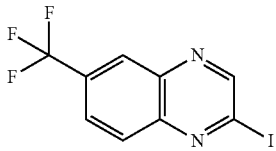 [SMILES: FC(F)(F)c1ccc2nc(I)cnc2c1]

1H-NMR ($D_6$-DMSO) δ ppm: 9.26(s, 1H), 8.45-8.43(m, 1H), 8.31-8.25(m, 1H), 8.14-8.11(m, 1H)

6-Bromo-2-iodoquinoxaline (VII-05)

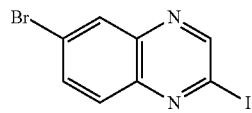

1H-NMR ($D_6$-DMSO) δ ppm: 9.13(s, 1H), 8.31(m, 1H), 7.99(m, 2H)

2-Chloro-3-methyl-6-(trifluoromethyl)quinoxaline and 3-chloro-2-methyl-6-(trifluoromethyl)quinoxaline (VII-06)

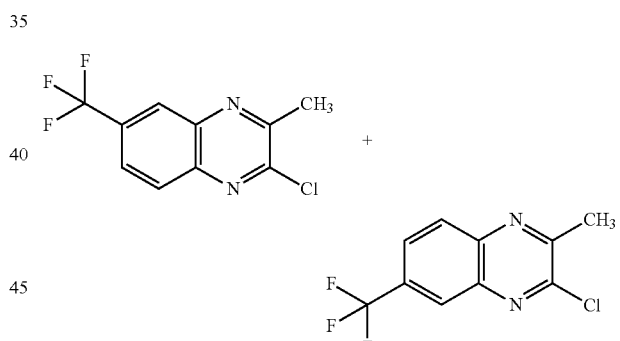

1:1-mixture of the regioisomers:

1H-NMR ($D_6$-DMSO) δ ppm: 8.35-7.90(m, 3H, both regioisomers), 2.89(s, 3H), 2.88(s, 3H)

6-Chloro-2,2-difluoro[1,3]dioxolo[4,5-g]quinoxaline (VII-07)

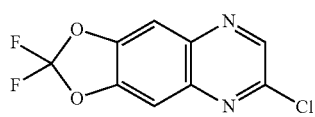 [SMILES: FC1(F)Oc2cc3ncc(Cl)nc3cc2O1]

1H-NMR($D_6$-DMSO) δ ppm: 9.01(s, 1H), 8.17(s, 1H), 8.10(s, 1H)

2-Chloro-6,7-difluoroquinoxaline (VII-08)

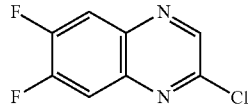

1H-NMR(CDCl$_3$) δ ppm: 8.78(s, 1H), 7.91-7.86(m, 1H), 7.81-7.77(s, 1H)

6-Chloro-2,2-difluoro-7-methyl[1,3]dioxolo[4,5-g]quinoxaline (VII-09)

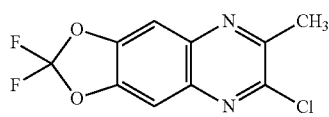 [SMILES: Cc1nc2cc3c(cc2nc1Cl)OC(F)(F)O3]

1H-NMR(D$_6$-DMSO) δ ppm: 8.07(s, 1H), 8.05(s, 1H), 2.76(s, 3H)

2-Chloro-6-(difluoromethoxy)quinoxaline and 2-chloro-7-(difluoromethoxy)quinoxaline (VII-10)

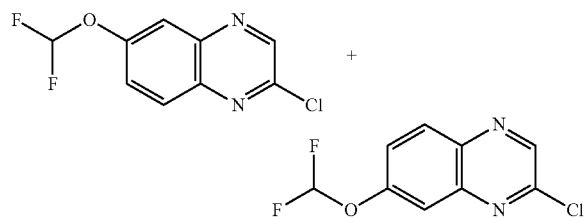

1:5-mixture of the regioisomers:
1H-NMR (CDCl3) δ ppm: 8.80-7.56(m, 4H, both regioisomers), 6.72(t, 1H)

Use examples

*Boophilus microplus* test (BOOPMI injection)
Solvent: dimethyl sulfoxide

To produce a suitable preparation of active compound, 10 mg of active compound are mixed with 0.5 ml of solvent and the concentrate is diluted with solvent to the desired concentration.

The active compound solution is injected into the abdomen (*Boophilus microplus*), and the animals are transferred into dishes and stored in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 80% at an application rate of 20 μg/animal: I-7

In this test, for example, the following compounds from the preparation examples show an efficacy of 85% at an application rate of 20 μg/animal: I-2

In this test, for example, the following compounds from the preparation examples show an efficacy of 90% at an application rate of 20 μg/animal: I-36

*Haemonchus contortus*-test (HAEMCO)
Solvent: dimethyl sulfoxide

To produce a suitable preparation of active compound, 10 mg of active compound are mixed with 0.5 ml of dimethyl sulfoxide and the concentrate is diluted with "Ringer's solution" to the desired concentration.

Vessels containing the active compound preparation of the desired concentration are populated with about 40 larvae of the red stomach worm (*Haemonchus contortus*).

After 5 days, the kill in % is determined. 100% means that all the larvae have been killed; 0% means that none of the larvae have been killed.

In this test, for example, the following compounds from the preparation examples show an efficacy of 80% at an application rate of 20 ppm: I-4, I-32

In this test, for example, the following compounds from the preparation examples show an efficacy of 100% at an application rate of 100 ppm: I-8, I-9

*Cooperia curticei* test (COOPCU)
Solvent: dimethyl sulfoxide

To produce a suitable preparation of active compound, 10 mg of active compound are mixed with 0.5 ml of dimethyl sulfoxide and the concentrate is diluted with "Ringer's solution" to the desired concentration.

Vessels containing the active compound preparation of the desired concentration are populated with about 40 nematode larvae (*Cooperia curticei*).

After 5 days, the kill in % is determined. 100% means that all the larvae have been killed; 0% means that none of the larvae have been killed.

In this test, for example, the following compounds from the preparation examples show an efficacy of 80% at an application rate of 20 ppm: I-32

In this test, for example, the following compounds from the preparation examples show an efficacy of 90% at an application rate of 20 ppm: I-40

In this test, for example, the following compounds from the preparation examples show an efficacy of 100% at an application rate of 100 ppm: I-8, I-9

*Nippostrongylus brasiliensis* test (NIPOBR)
Test method for in vitro experiments with *Nippostrongylus brasiliensis*

Adult *Nippostrongylus brasiliensis* is isolated from the small intestine of female Wistar rats and transferred into buffer solution containing 100 U/ml penicillin, 0.1 mg/ml streptomycin and 2.5 μg/ml amphotericin B.

The incubation of the worms (both sexes) is carried out in 1.0 ml of the medium also used for determining the acetylcholinesterase activity.

The compounds are dissolved in DMSO and added to the incubation medium such that final concentrations of 10 and 1 μg/ml, respectively, are present. The controls contain only DMSO.

Incubation is carried out at 37° C. and 5% CO$_2$.

The enzyme determination is carried out using an aliquot of the medium. The AChE to be measured cleaves the substrate acetylthiocholine iodide (which is present as the iodide salt) into the products acetate and thiocholine.

In the subsequent reaction, thiocholine forms, with dithionitrobenzoic acid (DTNB, Ellman's reagent), a yellow dye (thionitrobenzoate).

The intensity of the color (=activity of AChE) is determined via the optical density (OD) photometrically at 405 nm and compared to the OD of the negative control.

The activity is classified into the categories 84% (60-84% inhibition) and
100% (>84-100% inhibition).

In this test, for example, the following compounds from the preparation examples show an efficacy of 84% at an application rate of 10 ppm: I-8

In this test, for example, the following compounds from the preparation examples show an efficacy of 100% at an application rate of 10 ppm: I-9

*Meloidogyne incognita* test (MELGIN)

Solvent: 125.0 parts by weight of acetone

To produce a suitable preparation of active compound, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples show an efficacy of 90% at an application rate of 20 ppm: I-7, I-74

*Phaedon cochleariae*—spray test (PHAECO)

Solvent: 78.0 parts by weight of acetone
1.5 parts by weight of dimethylformamide
Emulsifier: 0.5 part by weight of alkylaryl polyglycol ether To produce a suitable active compound preparation, 1 part by weight of active compound is mixed with the stated amounts of solvent and emulsifier, and the concentrate is diluted with emulsifier-containing water to the desired concentration.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 83% at an application rate of 500 g/ha: I-15, I-36

In this test, for example, the following compounds from the preparation examples show an efficacy of 100% at an application rate of 500 g/ha: I-7, I-9, I-14, I-34

*Spodoptera frugiperda*—spray test (SPODFR)

Solvent: 78.0 parts by weight of acetone
1.5 parts by weight of dimethylformamide
Emulsifier: 0.5 parts by weight of alkylaryl polyglycol ether To produce a suitable active compound preparation, 1 part by weight of active compound is mixed with the stated amounts of solvent and emulsifier, and the concentrate is diluted with emulsifier-containing water to the desired concentration.

Leaf discs of maize (*Zea mays*) are sprayed with an active compound preparation of the desired concentration and, after drying, populated with caterpillars of the armyworm (*Spodoptera frugiperda*).

After 7 days, the efficacy in % is determined. 100% means that all the caterpillars have been killed; 0% means that no caterpillars have been killed.

In this test, for example, the following compounds from the preparation examples show an efficacy of 83% at an application rate of 500 g/ha: I-29

In this test, for example, the following compounds from the preparation examples show an efficacy of 100% at an application rate of 500 g/ha: I-14, I-15

*Tetranychus urticae*—spray test, OP-resistant (TETRUR)

Solvent: 78.0 parts by weight of acetone
1.5 parts by weight of dimethylformamide
Emulsifier: 0.5 part by weight of alkylaryl polyglycol ether To produce a suitable active compound preparation, 1 part by weight of active compound is mixed with the stated amounts of solvent and emulsifier, and the concentrate is diluted with emulsifier-containing water to the desired concentration.

Discs of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites have been killed; 0% means that no spider mites have been killed.

In this test, for example, the following compounds from the preparation examples show an efficacy of 90% at an application rate of 500 g/ha: I-12, I-18, I-25, I-26, I-27, I-34, I-36, I-43, I-46, I-48, I-66

In this test, for example, the following compounds from the preparation examples show an efficacy of 100% at an application rate of 500 g/ha: I-1, I-14, I-15, I-21, I-24, I-51

*Myzus persicae*—spray test (MYZUPE)

Solvent: 78 parts by weight of acetone
1.5 parts by weight of dimethylformamide
Emulsifier: 0.5 part by weight of alkylaryl polyglycol ether To produce a suitable active compound preparation, 1 part by weight of active compound is mixed with the stated amounts of solvent and emulsifier, and the concentrate is diluted with emulsifier-containing water to the desired concentration.

Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined. 100% means that all the aphids have been killed; 0% means that no aphids have been killed.

In this test, for example, the following compounds from the preparation examples show an efficacy of 90% at an application rate of 100 g/ha: I-62

In this test, for example, the following compounds from the preparation examples show an efficacy of 100% at an application rate of 100 g/ha: I-10

In this test, for example, the following compounds from the preparation examples show an efficacy of 90% at an application rate of 500 g/ha: I-1, I-7, I-9, I-18, I-22, I-31, I-32, I-36, I-63, I-66

In this test, for example, the following compounds from the preparation examples show an efficacy of 90% at an application rate of 750 g/ha: I-2, I-11

*Aphis gossypii*—spray test

Solvent: 7 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Cotton plants (*Gossypium hirsutum*) which are heavily infested by the cotton aphid (*Aphis gossypii*) are sprayed with an active compound preparation of the desired concentration.

After 6 days, the kill in % is determined. 100% means that all the aphids have been killed; 0% means that no aphids have been killed.

In this test, for example, the following compounds from the preparation examples show an efficacy of 85% at an application rate of 20 ppm: I-1, I-10

In this test, for example, the following compounds from the preparation examples show an efficacy of 80% at an application rate of 100 ppm: I-2

In this test, for example, the following compounds from the preparation examples show an efficacy of 85% at an application rate of 100 ppm: I-9

In this test, for example, the following compounds from the preparation examples show an efficacy of 90% at an application rate of 100 ppm: I-32

In this test, for example, the following compounds from the preparation examples show an efficacy of 95% at an application rate of 100 ppm: I-66

In this test, for example, the following compounds from the preparation examples show an efficacy of 97% at an application rate of 100 ppm: I-62

In this test, for example, the following compounds from the preparation examples show an efficacy of 100% at an application rate of 100 ppm: I-11, I-30

Bemisia Tabaci—Spray Test
Solvent: 7 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Cotton plants (*Gossypium hirsutum*) which are infested by larvae of the whitefly (*Bemisia tabaci*) are sprayed with an active compound preparation of the desired concentration.

After 8 days, the efficacy in % is determined. 100% means that all the whiteflies have been killed; 0% means that none of the whiteflies have been killed.

In this test, for example, the following compounds from the preparation examples show an efficacy of 100% at an application rate of 20 ppm: I-2

In this test, for example, the following compounds from the preparation examples show an efficacy of 90% at an application rate of 100 ppm: I-15

In this test, for example, the following compounds from the preparation examples show an efficacy of 96% at an application rate of 100 ppm: I-26

In this test, for example, the following compounds from the preparation examples show an efficacy of 100% at an application rate of 100 ppm: I-7, I-11, I-30

*Nilaparvata lugens*—spray test
Solvent: 7 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Rice plants (*Oryza sativa*) are sprayed with an active compound preparation of the desired concentration and then populated with larvae of the brown planthopper (*Nilaparvata lugens*).

After 7 days, the efficacy in % is determined. 100% means that all of the planthoppers have been killed; 0% means that none of the planthoppers have been killed.

In this test, for example, the following compounds from the preparation examples show an efficacy of 100% at an application rate of 20 ppm: I-1, I-2

In this test, for example, the following compounds from the preparation examples show an efficacy of 80% at an application rate of 100 ppm: I-26, I-30

In this test, for example, the following compounds from the preparation examples show an efficacy of 90% at an application rate of 100 ppm: I-11

*Nilaparvata lugens*—spray test
Solvent: 52.5 parts by weight of acetone
7 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Rice plants (*Oryza sativa*) are sprayed with an active compound preparation of the desired concentration and then populated with larvae of the brown planthopper (*Nilaparvata lugens*).

After 4 days, the efficacy in % is determined. 100% means that all of the planthoppers have been killed; 0% means that none of the planthoppers have been killed.

In this test, for example, the following compounds from the preparation examples show an efficacy of 90% at an application rate of 500 g/ha: I-7

*Nephotettix cincticeps* test (NEPHCI)
Solvent: 7 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water. In the event that addition of ammonium salts or/and penetrants (rapeseed oil methyl ester) is required, these are each pipetted in in a concentration of 1000 ppm after the finished formulation solution has been diluted.

Rice plants (*Oryza sativa*, var. *Balilla*) are treated by spraying with the active compound preparation in the desired concentration and then populated with larvae of the green rice leafhopper (*Nephotettix cincticeps*).

After 14 days, the kill in % is determined. 100% means that all leafhoppers have been killed; 0% means that none of the leafhoppers have been killed.

In this test, for example, the following compound from the preparation examples shows an efficacy of 100% at an application rate of 100 ppm: I-2

The invention claimed is:
1. A compound of formula (I-L)

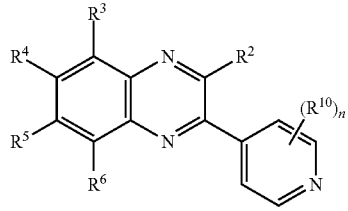

(I-L)

wherein
R² represents hydrogen, methyl, or ethyl, or represents in each case optionally chlorine-substituted phenyl or hetaryl group Q-41

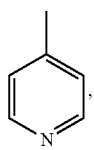

Q-41

R³ represents hydrogen,
R⁴ represents hydrogen, chlorine, fluorine, cyano, SO₂CH₃, SO₂C₂H₅, trifluoromethyl, difluoromethyl, difluoromethoxy, trifluoromethoxy or 2,2,2-trifluoroethoxy,
R⁵ represents hydrogen, chlorine, fluorine, cyano, SO₂CH₃, SO₂C₂H₅, trifluoromethyl, difluoromethyl, difluoromethoxy, trifluoromethoxy or 2,2,2-trifluoroethoxy,
R⁶ represents hydrogen,
with the proviso that R³, R⁴, R⁵ and R⁶ do not simultaneously represent hydrogen,
or R³ and R⁴ together or R⁴ and R⁵ together or R⁵ and R⁶ together are

to form a 5-membered ring which is optionally mono- or disubstituted by fluorine,
R¹⁰ represents methyl, ethyl, chlorine, fluorine, cyano, difluoromethyl, trifluoromethyl, SCH₃, SOCH₃, SO₂CH₃, SC₂H₅, SOC₂H₅, SO₂C₂H₅, methoxy, ethoxy, difluoromethoxy, trifluoromethoxy or 2,2,2-trifluoroethoxy, and
n represents 0 or 1.
2. A compound of formula (I-L) as claimed in claim 1 wherein
R² represents hydrogen, or methyl, or represents hetaryl group Q-41, or represents phenyl which is optionally monosubstituted by chlorine,
R³ represents hydrogen,
R⁴ represents hydrogen, fluorine, chlorine, cyano or trifluoromethyl,
R⁵ represents hydrogen, fluorine, chlorine, trifluoromethyl or SO₂CH₃, or R⁴ and R⁵ together represent —O—CF₂—O—,
R⁶ represents hydrogen,
with the proviso that R³, R⁴, R⁵ and R⁶ do not simultaneously represent hydrogen,
R¹⁰ represents methyl, ethyl, chlorine, fluorine, trifluoromethyl, SCH₃, SO₂CH₃, SC₂H₅, SOC₂H₅, SO₂C₂H₅, methoxy or ethoxy, and
n represents 0 or 1.
3. A composition comprising at least one compound of formula (I) as claimed in claim 1 and one or more customary extenders and/or surfactants.
4. A method for controlling one or more pests comprising applying a compound of formula (I) as claimed in claim 1 to the pests and/or a habitat thereof.
5. A compound of formula (I-L) as claimed in claim 1 wherein
R² represents hydrogen or methyl, or represents in each case optionally chlorine-substituted phenyl or hetaryl group Q-41

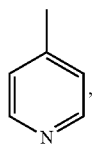

Q-41

R³ represents hydrogen,
R⁴ represents hydrogen, chlorine, fluorine, cyano, or trifluoromethyl,
R⁵ represents hydrogen, chlorine, fluorine, SO₂CH₃, or trifluoromethyl, or
R⁴ and R⁵ together represent —O—CF₂—O—,
R⁶ represents hydrogen,
with the proviso that R³, R⁴, R⁵ and R⁶ do not simultaneously represent hydrogen,
R¹⁰ represents methyl, ethyl, chlorine, SC₂H₅, or methoxy, and
n represents 0 or 1.
6. A compound of formula (I-L) as claimed in claim 1 wherein
R² represents hydrogen or methyl,
R³ represents hydrogen,
R⁴ represents hydrogen, fluorine, or trifluoromethyl,
R⁵ represents hydrogen, fluorine, or trifluoromethyl, or
R⁴ and R⁵ together represent —O—CF₂—O—,
R⁶ represents hydrogen,
with the proviso that R³, R⁴, R⁵ and R⁶ do not simultaneously represent hydrogen,
R¹⁰ represents methyl, ethyl, chlorine, or methoxy, and
n represents 0 or 1.
7. A compound of formula (I-L) as claimed in claim 1 having the formula

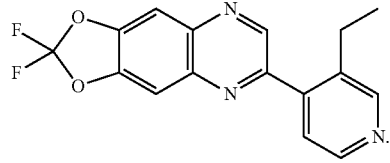 [SMILES: CCc1cnccc1-c1cnc2cc3c(cc2n1)OC(F)(F)O3]

8. A compound of formula (I-L) as claimed in claim 1 having the formula

105
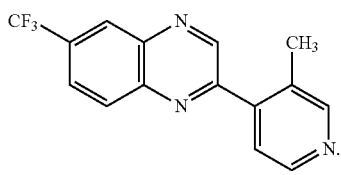 [SMILES: Cc1cnccc1-c1cnc2cc(C(F)(F)F)ccc2n1]
9. A compound of formula (I-L) as claimed in claim 1 having the formula
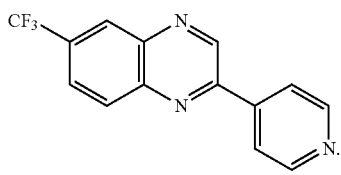 [SMILES: FC(F)(F)c1ccc2nc(-c3ccncc3)cnc2c1]
10. A compound of formula (I-L) as claimed in claim 1 having the formula
106
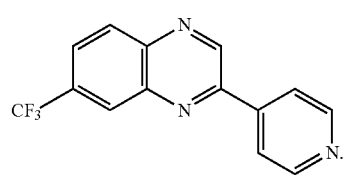 [SMILES: FC(F)(F)c1ccc2ncc(-c3ccncc3)nc2c1]
11. A compound of formula (I-L) as claimed in claim 1 having the formula
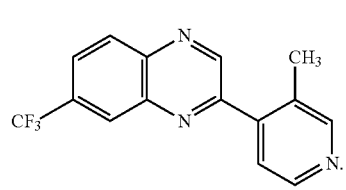 [SMILES: Cc1cnccc1-c1cnc2ccc(C(F)(F)F)cc2n1]
* * * * *